(12) United States Patent
Cuero Rengifo et al.

(10) Patent No.: US 12,129,500 B2
(45) Date of Patent: *Oct. 29, 2024

(54) METHODS FOR PRODUCING A POLYACTIVE CARBOHYDRATE AND APPLICATIONS THEREOF

(71) Applicant: BIOCAPITAL HOLDINGS, LLC, Houston, TX (US)

(72) Inventors: Raul Cuero Rengifo, Cypress, TX (US); Juliana Londono Murillo, Manizales (CO)

(73) Assignee: BIOCAPITAL HOLDINGS, LLC, Houston, TX (US)

( * ) Notice: Subject to any disclaimer, the term of this patent is extended or adjusted under 35 U.S.C. 154(b) by 711 days.

This patent is subject to a terminal disclaimer.

(21) Appl. No.: 17/245,416

(22) Filed: Apr. 30, 2021

(65) Prior Publication Data

US 2021/0261997 A1 Aug. 26, 2021

Related U.S. Application Data

(63) Continuation of application No. 16/646,218, filed as application No. PCT/US2018/050571 on Sep. 12, 2018, now Pat. No. 10,995,353.

(60) Provisional application No. 62/635,005, filed on Feb. 26, 2018, provisional application No. 62/557,339, filed on Sep. 12, 2017.

(51) Int. Cl.

| | |
|---|---|
| *C12P 19/14* | (2006.01) |
| *C12N 9/10* | (2006.01) |
| *C12N 9/16* | (2006.01) |
| *C12N 9/24* | (2006.01) |
| *C12N 9/42* | (2006.01) |
| *C12N 9/80* | (2006.01) |
| *C12N 15/52* | (2006.01) |

(52) U.S. Cl.
CPC ............ *C12P 19/14* (2013.01); *C12N 9/1051* (2013.01); *C12N 9/16* (2013.01); *C12N 9/2434* (2013.01); *C12N 9/80* (2013.01); *C12N 15/52* (2013.01); *C12Y 204/01016* (2013.01); *C12Y 302/01132* (2013.01); *C12Y 305/01041* (2013.01)

(58) Field of Classification Search
None
See application file for complete search history.

(56) References Cited

U.S. PATENT DOCUMENTS

| | | |
|---|---|---|
| 2005/0042735 A1 | 2/2005 | Deng et al. |
| 2013/0337541 A1 | 12/2013 | Brzezinski et al. |
| 2016/0168311 A1 | 6/2016 | Cuero Rengifo et al. |
| 2017/0035600 A1 | 2/2017 | Preciado |
| 2017/0356002 A1 | 12/2017 | Thompson et al. |

FOREIGN PATENT DOCUMENTS

| | | | |
|---|---|---|---|
| CN | 101654690 A | * | 2/2010 |
| CN | 104970989 A | * | 10/2015 |
| KR | 20160037354 A | * | 4/2016 |
| WO | 2000009729 | | 2/2000 |

OTHER PUBLICATIONS

Kim et al., "Enzymatic production and biological activities of chitosan oligosaccharides (COS): A review", Carbohydrate Polymers, vol. 62, pp. 357-368 (Year: 2005).*
Nagahashi et al.; Characterization of Chitin Synthase 2 of *Saccharomyces cerevisiae*; The Journal of Biological Chemistry; vol. 270, No. 23, pp. 13961-13967, published Jun. 9, 1995 (Year: 1995).
Shimosaka et al.; Analysis of Essential Carboxylic Amino Acid Residues for Catalytic Activity of Fungal Chitosanases by Site-Directed Mutagenesis; Journal of Bioscience and Bioengineering; vol. 100, No. 5, pp. 545-550 (2005) (Year: 2005).
Arakane et al. Chitin-Related Enzymes in Agro-Biosciences, Current Drug Targets, 13, 00-00, 2012.
International Search Report and Written Opinion issued for PCT/US2018/050571, mailed Jan. 15, 2019.

* cited by examiner

*Primary Examiner* — Michelle F. Paguio Frising
(74) *Attorney, Agent, or Firm* — Thomas | Horstemeyer, LLP

(57) ABSTRACT

Described herein are biological devices and methods for using the same to produce a polyactive carbohydrate. The biological devices include microbial cells transformed with a DNA construct containing genes for producing a chitin synthase, a chitosanase, and a chitin deacetylase. In some instances, the biological devices also include a gene for lipase. Methods for using the polyactive carbohydrate are also provided herein, including, but not limited to, enhancing the physiological properties of plants; medical applications; applications in the construction, materials science, and home goods industries; personal care, grooming, cosmetics, and oral care compositions containing the polyactive carbohydrate; methods for water decontamination; and the production of polyurethanes.

17 Claims, 13 Drawing Sheets

Specification includes a Sequence Listing.

METHODS FOR PRODUCING A POLYACTIVE CARBOHYDRATE AND APPLICATIONS THEREOF

CROSS REFERENCE TO RELATED APPLICATIONS

This application is a continuation application of U.S. nonprovisional application Ser. No. 16/646,218 filed on Mar. 11, 2020, which is a US national phase application of international application no. PCT/US2018/050571 filed on Sep. 12, 2018, which claims priority upon U.S. provisional application Ser. No. 62/557,339 filed on Sep. 12, 2017 and 62/635,005 filed Feb. 26, 2018. These applications are hereby incorporated by reference in their entirety.

CROSS REFERENCE TO SEQUENCE LISTING

The genetic components described herein are referred to by sequence identifier numbers (SEQ ID NO). The SEQ ID NOs correspond numerically to the sequence identifiers <400>1, <400>2, etc. The sequence listing in written computer readable format (CRF) as a text file named "930201-1071_Sequence_Listing.xml" created on Apr. 30, 2021, and having a size of 68,731 bytes, is incorporated by reference in its entirety.

BACKGROUND

Chitosan is a linear polysaccharide derived from chitin, a polymer found in the shells of shrimp and other crustaceans as well as in some fungal cell walls. Chitosan is composed of D-glucosamine and N-acetyl-D-glucosamine units, which are β-(1→4) linked and randomly distributed.

Chitosan has been employed for a wide variety of commercial uses. However, several drawbacks to the widespread use of chitosan exist. Few facilities worldwide are able to process chitosan, and the separation of chitosan from crustacean shells is laborious. Separation methods are inefficient as the necessary reagents cannot easily access the polymer due to the crystalline nature of chitin. Existing methods for producing chitosan are destructive and wasteful in addition to being expensive, and they employ corrosive chemicals and hazardous solvents. Further, since chitosan is typically extracted from shellfish, individuals with shellfish allergies, vegans and vegetarians, and people with religious prohibitions against consuming shellfish may want to avoid products containing chitosan extracted from shrimp, crabs, and the like.

What is needed is a polyactive carbohydrate and a process for making the same that shares the properties of chitosan. Purification would not require the use of harsh chemicals or solvents, thus reducing materials costs and the production of hazardous waste. Further, the polyactive carbohydrate would be suitable for use in all of the industrial applications traditionally associated with chitosan. The present invention addresses these needs.

SUMMARY

Described herein are biological devices and methods for using the same to produce a polyactive carbohydrate. The biological devices include microbial cells transformed with a DNA construct containing genes for producing a chitin synthase, a chitosanase, and a chitin deacetylase. In some instances, the biological devices also include a gene for lipase. Methods for using the polyactive carbohydrate are also provided herein, including, but not limited to, enhancing the physiological properties of plants; medical applications; applications in the construction, materials science, and home goods industries; personal care, grooming, cosmetics, and oral care compositions containing the polyactive carbohydrate; methods for water decontamination; and the production of polyurethane biofoams.

The advantages to the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 3A shows initial mixing, FIG. 3B shows after heating the treatments for 20 min. at 60° C., FIG. 3C shows after heating the treatments for 40 min. at 60° C., and FIG. 3D shows after heating the treatments for one hour at 60° C. The compositions for each treatment are described in Table 6. In each of FIGS. 3A-D, Treatment "A" is in the jar on the left and treatment "B" is in the jar on the right.

FIG. 4A shows the initial application of a petroleum/extract mixture to Petri dishes, FIG. 4B shows the same Petri dishes after 10 min., and FIG. 4C shows the Petri dishes after 1 hour.

DETAILED DESCRIPTION

Figure 1A:
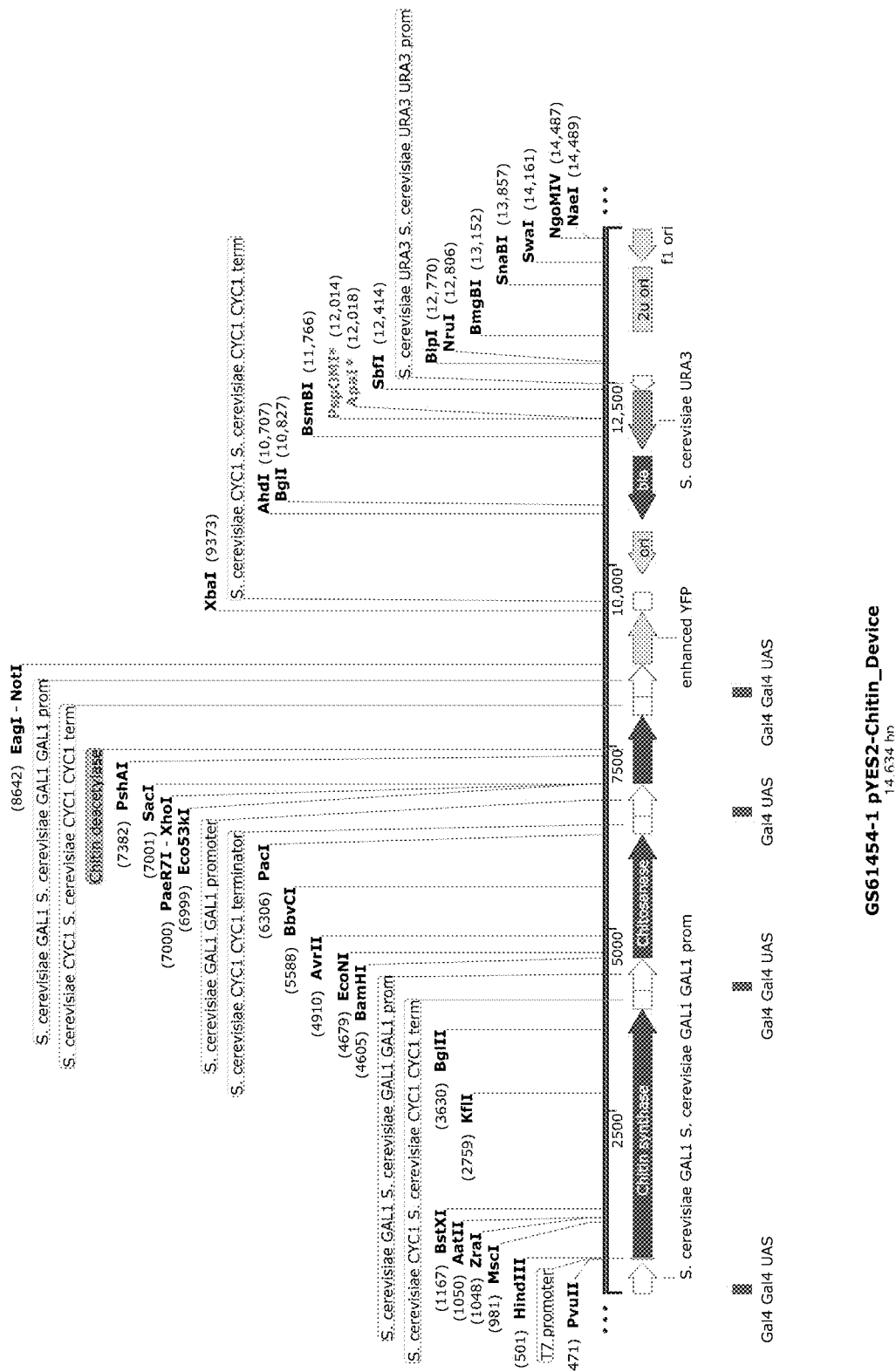
FIGS. 1A and 1B show, respectively, a linear and circular schematic of a constructed pYES2 plasmid showing the direction, placement, and size of genetic parts used of an exemplary DNA device described herein.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a plasmid" includes mixtures of two or more such plasmids, and the like.

"Optional" or "optionally" means that the subsequently described event or circumstance can or cannot occur, and that the description includes instances where the event or circumstance occurs and instances where it does not. For example, the phrase "optionally includes a reporter protein" means that the reporter protein may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Admixing" or "admixture" refers to a combination of two or more components together wherein there is no chemical reaction or physical interaction. The terms "admixing" and "admixture" can also include the chemical reaction or physical interaction between any of the components described herein upon mixing to produce the composition. The components can be admixed alone, in water, in another solvent, or in a combination of solvents.

"Contaminants" include, but are not limited to, microorganisms and their spores, detergents and surfactants, fertilizers, heavy metals and metal salts, laundry soap, oil or petroleum, pharmaceuticals and other organic compounds, pesticides, oils used for cooking or lubricating, biodegradable waste, high levels of acid or alkali, sewage, byproducts of industrial processes, dyes, and the like. "Petroleum contaminants" refers to petroleum and petroleum-derived products and/or lipids as well as hydrocarbons and petroleum hydrocarbons.

"Hydrocarbons" and "petroleum hydrocarbons" are organic compounds consisting of carbon and hydrogen and include, but are not limited to, hexane, benzene, toluene, xylenes, naphthalene, fluorine, and related compounds, as well as constituents of gasoline, jet fuels, mineral oils, kerosene, extractable petroleum hydrocarbons, diesel range organics, and the like. Petroleum hydrocarbons may be aliphatic or aromatic, including polynuclear aromatic hydrocarbons.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference to each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed fro disclosure of A, B, and C; D, E, and F; and the example combination A-D. Likewise, any subset or combination of these is also specifically contemplated and disclosed. Thus, for example, the subgroup of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, a "polyactive carbohydrate" is a compound produced by the biological devices disclosed herein. In one aspect, the polyactive carbohydrate is partially or fully acetylated. In another aspect, an enzymatic or chemical deacetylation process can be used on the polyactive carbohydrate or any precursors to alter the degree of acetylation. In still another aspect, the polyactive carbohydrate can be chemically or enzymatically fully or partially hydrolyzed prior to use in order to fine tune the properties of the polyactive carbohydrate as they relate to molecular weight. Example applications of the polyactive carbohydrate are discussed in detail below.

Described herein is a process for producing polyactive carbohydrates using microbial cells that includes (a) making a DNA construct containing genes for producing chitin synthase, chitosanase, and chitin deacetylase, (b) introducing the DNA construct into host microbial cells via transformation or transfection, and (c) culturing the microbial cells to produce polyactive carbohydrates.

I. DNA Constructs

DNA constructs are provided herein for the production of polyactive carbohydrates. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning two sequences so that the homology is at its highest level. Another way of calculating homology can be performed according to published algorithms (see Zuker, M., *Science,* 244:48-52, 1989; Jaeger et al, *Proc. Natl. Acad. Sci. USA,* 86:7706-7710, 1989; Jaeger et al, *Methods Enzymol.,* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, provided herein is a DNA construct comprising the following genetic components:
a) a gene that expresses chitin synthase;
b) a gene that expresses chitosanase; and
c) a gene that expresses chitin deacetylase.

In another aspect, provided herein is a DNA construct comprising the following genetic components:
a) a gene that expresses chitin synthase;
b) a gene that expresses chitosanase;
c) a gene that expresses chitin deacetylase; and
d) a gene that expresses lipase.

Each component of the DNA construct is described in detail below.

In one aspect, the nucleic acids (e.g., genes that express chitin synthase, chitosanase, and chitin deacetylase) used in the DNA constructs described herein can be amplified using polymerase chain reaction (PCR) prior to being ligated into a plasmid or other vector. Typically, PCR-amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or genes. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

Chitin synthase is a glycosyltransferase enzyme that catalyzes the following reaction:

UDP-N-acetyl-D-glucosamine+[1,4-(N-acetyl-β-D-glucosaminyl)]$_n$→UDP+[1,4-(N-acetyl-β-D-glucosaminyl)]$_{n+1}$ where UDP is uridine diphosphate and N-acetyl-D-glucosamine units are added to the growing chitin chain one residue at a time.

In one aspect, the gene that expresses chitin synthase is isolated from yeast. In a further aspect, the yeast can be *Saccharomyces cerevisiae*. In a still further aspect, the *S. cerevisiae* strain that is the source of chitin synthase can be strain S288c, BSPX042, ySR127, DBVPG6765, YJM1526, YJM972, YJM969, YJM470, YJM248, YJM1478, YJM996, YJM244, YJM1477, YJM1387, YJM993, YJM1332, YJM1242, YJM990, T63, T52, or any other commonly cultured experimental strain of yeast. In another aspect, the *S. cerevisiae* is a wild type strain. In a further aspect, the gene that expresses chitin synthase has SEQ ID NO. 1 or at least 70% homology thereto, at least 75% homology thereto, at least 80% homology thereto, at least 85% homology thereto, at least 90% homology thereto, or at least 95% homology thereto. In one aspect, the gene that expresses chitin synthase is isolated from *Saccharomyces cerevisiae* and can be found in GenBank with GI number NC_001146.8.

Other sequences expressing chitin synthase or related or homologous genes can be identified in a database such as, for example, GenBank. In one aspect, sequences useful herein include those with the GI numbers listed in Table 1.

TABLE 1

Chitin Synthase Genes

| Source Organism | Sequence Description | GI Number |
|---|---|---|
| Saccharomyces cerevisiae | synthetic construct | DQ331902.1 |
| Saccharomyces cerevisiae | chromosome XIV sequence | CP020136.1 |
| Saccharomyces cerevisiae | chromosome XIV sequence | CP014729.1 |
| Saccharomyces cerevisiae | chromosome XIV sequence | CP011560.1 |
| Saccharomyces cerevisiae | chromosome XIV sequence | BK006947.3 |
| Saccharomyces cerevisiae | chitin synthase | NM_001183030.2 |
| Saccharomyces cerevisiae | chromosome XIV sequence | Z71468.1 |
| Saccharomyces cerevisiae | chitin synthase | M14045.1 |
| Saccharomyces cerevisiae | chromosome XIV sequence | CP020170.1 |
| Saccharomyces cerevisiae | chromosome XIV sequence | CP005579.2 |
| Saccharomyces cerevisiae | chromosome XIV sequence | CP005519.2 |
| Saccharomyces cerevisiae | chromosome XIV sequence | CP005518.2 |
| Saccharomyces cerevisiae | chromosome XIV sequence | CP005508.2 |
| Saccharomyces cerevisiae | chromosome XIV sequence | CP005498.2 |
| Saccharomyces cerevisiae | chromosome XIV sequence | CP005577.2 |
| Saccharomyces cerevisiae | chromosome XIV sequence | CP005527.2 |
| Saccharomyces cerevisiae | chromosome XIV sequence | CP005497.2 |
| Saccharomyces cerevisiae | chromosome XIV sequence | CP005576.2 |
| Saccharomyces cerevisiae | chromosome XIV sequence | CP005556.2 |
| Saccharomyces cerevisiae | chromosome XIV sequence | CP005526.2 |
| Saccharomyces cerevisiae | chromosome XIV sequence | CP005545.2 |
| Saccharomyces cerevisiae | chromosome XIV sequence | CP005535.2 |
| Saccharomyces cerevisiae | chromosome XIV sequence | CP005525.2 |
| Saccharomyces cerevisiae | chromosome XIV sequence | CP008334.1 |
| Saccharomyces cerevisiae | chromosome XIV sequence | CP008317.1 |
| Saccharomyces cerevisiae | chromosome XIV sequence | CP008351.1 |
| Saccharomyces cerevisiae | chromosome XIV sequence | CP008470.1 |
| Saccharomyces cerevisiae | chromosome XIV sequence | CP008572.1 |
| Saccharomyces cerevisiae | chromosome XIV sequence | CP008674.1 |
| Saccharomyces cerevisiae | chromosome XIV sequence | CP008657.1 |
| Saccharomyces cerevisiae | chromosome XIV sequence | CP008623.1 |
| Saccharomyces cerevisiae | chromosome XIV sequence | CP008181.1 |
| Saccharomyces cerevisiae | chromosome XIV sequence | CP008147.1 |
| Saccharomyces cerevisiae | chromosome XIV sequence | CP008045.1 |
| Saccharomyces cerevisiae | chromosome XIV sequence | CP008028.1 |
| Saccharomyces cerevisiae | chromosome XIV sequence | CP008011.1 |
| Saccharomyces cerevisiae | chromosome XIV sequence | CP007926.1 |
| Saccharomyces cerevisiae | chromosome XIV sequence | CP007892.1 |
| Saccharomyces cerevisiae | chromosome XIV sequence | CP007875.1 |
| Saccharomyces cerevisiae | chromosome XIV sequence | CP007858.1 |
| Saccharomyces cerevisiae | chromosome XIV sequence | CP007824.1 |
| Saccharomyces cerevisiae | chromosome XIV sequence | CP005494.2 |
| Saccharomyces cerevisiae | chromosome XIV sequence | CP005583.2 |
| Saccharomyces cerevisiae | chromosome XIV sequence | CP005573.2 |
| Saccharomyces cerevisiae | chromosome XIV sequence | CP005533.2 |
| Saccharomyces cerevisiae | chromosome XIV sequence | CP005523.2 |
| Saccharomyces cerevisiae | chromosome XIV sequence | CP005503.2 |
| Saccharomyces cerevisiae | chromosome XIV sequence | CP005552.2 |
| Saccharomyces cerevisiae | chromosome XIV sequence | CP005542.2 |
| Saccharomyces cerevisiae | chromosome XIV sequence | CP005532.2 |
| Saccharomyces cerevisiae | chromosome XIV sequence | CP005522.2 |
| Saccharomyces cerevisiae | chromosome XIV sequence | CP005521.2 |
| Saccharomyces cerevisiae | chromosome XIV sequence | CP005550.2 |
| Saccharomyces cerevisiae | chromosome XIV sequence | CP005520.2 |
| Saccharomyces cerevisiae | chromosome XIV sequence | CP005500.2 |
| Saccharomyces cerevisiae | chromosome XIV sequence | CP005524.1 |
| Saccharomyces cerevisiae | chromosome XIV sequence | CP005516.1 |
| Saccharomyces cerevisiae | chromosome XIV sequence | CP004112.1 |
| Saccharomyces cerevisiae | chromosome XIV sequence | CP008266.1 |
| Saccharomyces cerevisiae | chromosome XIV sequence | CP008453.1 |
| Saccharomyces cerevisiae | chromosome XIV sequence | CP008521.1 |
| Saccharomyces cerevisiae | chromosome XIV sequence | CP008640.1 |
| Saccharomyces cerevisiae | chromosome XIV sequence | CP008079.1 |
| Saccharomyces cerevisiae | chromosome XIV sequence | CP005529.2 |
| Saccharomyces cerevisiae | chromosome XIV sequence | CP005499.2 |
| Saccharomyces cerevisiae | chromosome XIV sequence | CP005548.2 |
| Saccharomyces cerevisiae | chromosome XIV sequence | CP005547.2 |
| Saccharomyces cerevisiae | chromosome XIV sequence | CP005546.2 |
| Saccharomyces cerevisiae | chromosome XIV sequence | CP005536.2 |
| Saccharomyces cerevisiae | chromosome XIV sequence | CP005506.2 |
| Saccharomyces cerevisiae | chromosome XIV sequence | CP008283.1 |
| Saccharomyces cerevisiae | chromosome XIV sequence | CP008232.1 |
| Saccharomyces cerevisiae | chromosome XIV sequence | CP008487.1 |
| Saccharomyces cerevisiae | chromosome XIV sequence | CP008436.1 |
| Saccharomyces cerevisiae | chromosome XIV sequence | CP008589.1 |
| Saccharomyces cerevisiae | chromosome XIV sequence | CP008555.1 |
| Saccharomyces cerevisiae | chromosome XIV sequence | CP008538.1 |
| Saccharomyces cerevisiae | chromosome XIV sequence | CP008606.1 |
| Saccharomyces cerevisiae | chromosome XIV sequence | CP008198.1 |
| Saccharomyces cerevisiae | chromosome XIV sequence | CP008164.1 |
| Saccharomyces cerevisiae | chromosome XIV sequence | CP008691.1 |
| Saccharomyces cerevisiae | chromosome XIV sequence | CP008130.1 |
| Saccharomyces cerevisiae | chromosome XIV sequence | CP008113.1 |
| Saccharomyces cerevisiae | chromosome XIV sequence | CP008096.1 |
| Saccharomyces cerevisiae | chromosome XIV sequence | CP007977.1 |
| Saccharomyces cerevisiae | chromosome XIV sequence | CP007960.1 |
| Saccharomyces cerevisiae | chromosome XIV sequence | CP005564.2 |
| Saccharomyces cerevisiae | chromosome XIV sequence | CP005544.2 |
| Saccharomyces cerevisiae | chromosome XIV sequence | CP005563.2 |
| Saccharomyces cerevisiae | chromosome XIV sequence | CP005581.2 |
| Saccharomyces cerevisiae | chromosome XIV sequence | CP005551.2 |
| Saccharomyces cerevisiae | chromosome XIV sequence | CP005531.2 |
| Saccharomyces cerevisiae | chromosome XIV sequence | CP005580.2 |
| Saccharomyces cerevisiae | chromosome XIV sequence | CP005530.2 |
| Saccharomyces cerevisiae | chromosome XIV sequence | CP005510.2 |
| Saccharomyces cerevisiae | chromosome XIV sequence | FN393086.1 |
| Saccharomyces cerevisiae | chromosome XIV sequence | CP008504.1 |
| Saccharomyces cerevisiae | chromosome XIV sequence | CP007909.1 |
| Saccharomyces cerevisiae | chromosome XIV sequence | CP005549.2 |
| Saccharomyces cerevisiae | chromosome XIV sequence | CP005539.2 |

Chitosanase is any one of a class of enzymes that perform hydrolysis of β-(1→4)-linkages between D-glucosamine residues in a partially acetylated chitosan molecule. The hydrolysis carried out by chitosanase typically occurs in the middle of the chitosan rather than at the ends.

In one aspect, the gene that expresses chitosanase is isolated from yeast. In a further aspect, the yeast can be *Saccharomyces cerevisiae*. In another aspect, the *S. cerevisiae* strain can be S288c, BSPX042, ySR127, YJM683, YJM682, YJM554, YJM541, YJM456, YJM326, YJM1615, YJM1208, YJM1133, NCIM3107, NCIM3186, T52, T63, YJM1573, YJM1402, YJM1401, another commonly cultured experimental strain, or can be a wild type strain. In a further aspect, the gene that expresses chitosanase has SEQ ID NO. 2 or at least 70% homology thereto, at least 75% homology thereto, at least 80% homology thereto, at least 85% homology thereto, at least 90% homology thereto, or at least 95% homology thereto. In one aspect, the gene that expresses chitosanase is isolated from *Saccharomyces cerevisiae* and can be found in GenBank with GI number AAB67331.1.

Other sequences expressing chitosanase or related or homologous genes can be identified in a database such as, for example, GenBank. In one aspect, sequences useful herein include those with the GI numbers listed in Table 2.

TABLE 2

Chitosanase Genes

| Source Organism | Sequence Description | GI Number |
|---|---|---|
| Saccharomyces cerevisiae | chromosome XII sequence | CP020134.1 |
| Saccharomyces cerevisiae | chromosome XII sequence | CP014727.1 |
| Saccharomyces cerevisiae | chromosome XII sequence | CP011558.1 |
| Saccharomyces cerevisiae | chromosome XII sequence | CP006456.1 |
| Saccharomyces cerevisiae | chromosome XII sequence | CP006455.1 |
| Saccharomyces cerevisiae | chromosome XII sequence | CP006451.1 |
| Saccharomyces cerevisiae | chromosome XII sequence | CP006450.1 |
| Saccharomyces cerevisiae | chromosome XII sequence | CP006448.1 |
| Saccharomyces cerevisiae | chromosome XII sequence | CP006443.1 |
| Saccharomyces cerevisiae | chromosome XII sequence | CP006434.1 |

TABLE 2-continued

Chitosanase Genes

| Source Organism | Sequence Description | GI Number |
|---|---|---|
| Saccharomyces cerevisiae | chromosome XII sequence | CP006383.1 |
| Saccharomyces cerevisiae | chromosome XII sequence | CP006379.1 |
| Saccharomyces cerevisiae | chromosome XII sequence | BK006945.2 |
| Saccharomyces cerevisiae | genomic DNA | NM_001182173.1 |
| Saccharomyces cerevisiae | chromosome XII sequence | U1743.1 |
| Saccharomyces cerevisiae | endochitinase | M74070.1 |
| Saccharomyces cerevisiae | chromosome XII sequence | CP009950.1 |
| Saccharomyces cerevisiae | chromosome XII sequence | CP011821.1 |
| Saccharomyces cerevisiae | chromosome XII sequence | CP008196.1 |
| Saccharomyces cerevisiae | chromosome XII sequence | CP008553.1 |
| Saccharomyces cerevisiae | chromosome XII sequence | CP008536.1 |
| Saccharomyces cerevisiae | chromosome XII sequence | CP008519.1 |
| Saccharomyces cerevisiae | chromosome XII sequence | CP008655.1 |
| Saccharomyces cerevisiae | chromosome XII sequence | CP008213.1 |
| Saccharomyces cerevisiae | chromosome XII sequence | CP008315.1 |
| Saccharomyces cerevisiae | chromosome XII sequence | CP008264.1 |
| Saccharomyces cerevisiae | chromosome XII sequence | CP008145.1 |
| Saccharomyces cerevisiae | chromosome XII sequence | CP006431.1 |
| Saccharomyces cerevisiae | chromosome XII sequence | CP006411.1 |
| Saccharomyces cerevisiae | chromosome XII sequence | CP006410.1 |
| Saccharomyces cerevisiae | chromosome XII sequence | CP008247.1 |
| Saccharomyces cerevisiae | chromosome XII sequence | CP008366.1 |
| Saccharomyces cerevisiae | chromosome XII sequence | CP008349.1 |
| Saccharomyces cerevisiae | chromosome XII sequence | CP008485.1 |
| Saccharomyces cerevisiae | chromosome XII sequence | CP008604.1 |
| Saccharomyces cerevisiae | chromosome XII sequence | CP008179.1 |
| Saccharomyces cerevisiae | chromosome XII sequence | CP008162.1 |
| Saccharomyces cerevisiae | chromosome XII sequence | CP008128.1 |
| Saccharomyces cerevisiae | chromosome XII sequence | CP008026.1 |
| Saccharomyces cerevisiae | chromosome XII sequence | CP007975.1 |
| Saccharomyces cerevisiae | chromosome XII sequence | CP007958.1 |
| Saccharomyces cerevisiae | chromosome XII sequence | CP007941.1 |
| Saccharomyces cerevisiae | chromosome XII sequence | CP007873.1 |
| Saccharomyces cerevisiae | chromosome XII sequence | CP007856.1 |
| Saccharomyces cerevisiae | chromosome XII sequence | CP007839.1 |
| Saccharomyces cerevisiae | chromosome XII sequence | CP008400.1 |
| Saccharomyces cerevisiae | chromosome XII sequence | CP020219.1 |
| Saccharomyces cerevisiae | chromosome XII sequence | CP008451.1 |
| Saccharomyces cerevisiae | chromosome XII sequence | CP006417.1 |
| Saccharomyces cerevisiae | chromosome XII sequence | CP006398.1 |
| Saccharomyces cerevisiae | chromosome XII sequence | CP006389.1 |
| Saccharomyces cerevisiae | chromosome XII sequence | CP008332.1 |
| Saccharomyces cerevisiae | chromosome XII sequence | CP008298.1 |
| Saccharomyces cerevisiae | chromosome XII sequence | CP008417.1 |
| Saccharomyces cerevisiae | chromosome XII sequence | CP008434.1 |
| Saccharomyces cerevisiae | chromosome XII sequence | CP008587.1 |
| Saccharomyces cerevisiae | chromosome XII sequence | CP008638.1 |
| Saccharomyces cerevisiae | chromosome XII sequence | CP008689.1 |
| Saccharomyces cerevisiae | chromosome XII sequence | CP008111.1 |
| Saccharomyces cerevisiae | chromosome XII sequence | CP008094.1 |
| Saccharomyces cerevisiae | chromosome XII sequence | CP008077.1 |
| Saccharomyces cerevisiae | chromosome XII sequence | CP008043.1 |
| Saccharomyces cerevisiae | chromosome XII sequence | CP007924.1 |
| Saccharomyces cerevisiae | chromosome XII sequence | CP007907.1 |
| Saccharomyces cerevisiae | chromosome XII sequence | CP007890.1 |
| Saccharomyces cerevisiae | chromosome XII sequence | CP007822.1 |
| Saccharomyces cerevisiae | chromosome XII sequence | CP008281.1 |
| Saccharomyces cerevisiae | chromosome XII sequence | CP006429.1 |
| Saccharomyces cerevisiae | chromosome XII sequence | CP006419.1 |
| Saccharomyces cerevisiae | chromosome XII sequence | CP008230.1 |
| Saccharomyces cerevisiae | chromosome XII sequence | CP008468.1 |
| Saccharomyces cerevisiae | chromosome XII sequence | CP008672.1 |
| Saccharomyces cerevisiae | chromosome XII sequence | CP008502.1 |
| Saccharomyces cerevisiae | chromosome XII sequence | CP006454.1 |
| Saccharomyces cerevisiae | chromosome XII sequence | CP006445.1 |
| Saccharomyces cerevisiae | chromosome XII sequence | CP006427.1 |
| Saccharomyces cerevisiae | chromosome XII sequence | CP006420.1 |
| Saccharomyces cerevisiae | chromosome XII sequence | CP006409.1 |
| Saccharomyces cerevisiae | chromosome XII sequence | CP006390.1 |
| Saccharomyces cerevisiae | chromosome XII sequence | CP008621.1 |
| Saccharomyces cerevisiae | chromosome XII sequence | CP008009.1 |
| Saccharomyces cerevisiae | chromosome XII sequence | CP006452.1 |
| Saccharomyces cerevisiae | chromosome XII sequence | CP006430.1 |
| Saccharomyces cerevisiae | chromosome XII sequence | CP006401.1 |
| Saccharomyces cerevisiae | chromosome XII sequence | CP006393.1 |
| Saccharomyces cerevisiae | chromosome XII sequence | CP007992.1 |
| Saccharomyces cerevisiae | chromosome XII sequence | CP006414.1 |
| Saccharomyces cerevisiae | chromosome XII sequence | CP008570.1 |
| Saccharomyces cerevisiae | chromosome XII sequence | CP008383.1 |
| Saccharomyces cerevisiae | chromosome XII sequence | CP020236.1 |
| Saccharomyces cerevisiae | chromosome XII sequence | CP006421.1 |
| Saccharomyces cerevisiae | chromosome XII sequence | CP008060.1 |
| Saccharomyces cerevisiae | chromosome XII sequence | CP020151.1 |
| Saccharomyces cerevisiae | chromosome XII sequence | CP006453.1 |
| Saccharomyces cerevisiae | chromosome XII sequence | CP006418.1 |
| Saccharomyces cerevisiae | chromosome XII sequence | CP006386.1 |
| Saccharomyces cerevisiae | chromosome XII sequence | CP006449.1 |
| Saccharomyces cerevisiae | chromosome XII sequence | CP006404.1 |
| Saccharomyces cerevisiae | chromosome XII sequence | LN907795.1 |
| Saccharomyces cerevisiae | chromosome XII sequence | CP006387.1 |

Chitin deacetylase is an enzyme that catalyzes the hydrolysis of chitin to chitosan and acetate. In one aspect, the chitin deacetylase reaction can proceed to completion. In an alternative aspect, the hydrolysis is incomplete, leaving some acetate groups attached to glucosamine residues in the polymer backbone.

In one aspect, the gene that expresses chitin deacetylase is isolated from yeast. In a further aspect, the yeast can be Saccharomyces cerevisiae. In another aspect, the S. cerevisiae strain can be Y12, S288c, BSPX042, N85, YJM470, YJM456, YJM1615, YJM1592, YJM1549, YJM1460, YJM1389, YJM1388, YJM1387, YJM1304, YJM1208, YJM689, YJM1202, YJM1199, YJM1133, YJM1381, YPS128, another commonly cultured experimental strain, or can be a wild type strain. In a further aspect, the gene that expresses chitin deacetylase has SEQ ID NO. 3 or at least 70% homology thereto, at least 75% homology thereto, at least 80% homology thereto, at least 85% homology thereto, at least 90% homology thereto, or at least 95% homology thereto. In one aspect, the gene that expresses chitin deacetylase is isolated from Saccharomyces cerevisiae and can be found in GenBank with accession number NM_001182196.

Other sequences expressing chitin deacetylase or related or homologous genes can be identified in a database such as, for example, GenBank. In one aspect, sequences useful herein include those with the GI numbers listed in Table 3.

TABLE 3

Chitin Deacetylase Genes

| Source Organism | Sequence Description | GI Number |
|---|---|---|
| Saccharomyces cerevisiae | chromosome XII sequence | CP020202.1 |
| Saccharomyces cerevisiae | chromosome XII sequence | CP020134.1 |
| Saccharomyces cerevisiae | chromosome XII sequence | CP014727.1 |
| Saccharomyces cerevisiae | chromosome XII sequence | LN907795.1 |
| Saccharomyces cerevisiae | chromosome XII sequence | CP006449.1 |
| Saccharomyces cerevisiae | chromosome XII sequence | CP006448.1 |
| Saccharomyces cerevisiae | chromosome XII sequence | CP006434.1 |
| Saccharomyces cerevisiae | chromosome XII sequence | CP006433.1 |
| Saccharomyces cerevisiae | chromosome XII sequence | CP006430.1 |
| Saccharomyces cerevisiae | chromosome XII sequence | CP006423.1 |
| Saccharomyces cerevisiae | chromosome XII sequence | CP006407.1 |
| Saccharomyces cerevisiae | chromosome XII sequence | CP006406.1 |
| Saccharomyces cerevisiae | chromosome XII sequence | CP006405.1 |
| Saccharomyces cerevisiae | chromosome XII sequence | CP006390.1 |
| Saccharomyces cerevisiae | chromosome XII sequence | CP006383.1 |
| Saccharomyces cerevisiae | chromosome XII sequence | BK006945.2 |
| Saccharomyces cerevisiae | chitin deacetylase | NM_001182196.1 |

TABLE 3-continued

Chitin Deacetylase Genes

| Source Organism | Sequence Description | GI Number |
|---|---|---|
| Saccharomyces cerevisiae | chromosome XII sequence | U17247.1 |
| Saccharomyces cerevisiae | chromosome XII sequence | CP006457.1 |
| Saccharomyces cerevisiae | chromosome XII sequence | CP006382.1 |
| Saccharomyces cerevisiae | chromosome XII sequence | CP006381.1 |
| Saccharomyces cerevisiae | chromosome XII sequence | CP006379.1 |
| Saccharomyces cerevisiae | chromosome XII sequence | CP006401.1 |
| Saccharomyces cerevisiae | chromosome XII sequence | CP020219.1 |
| Saccharomyces cerevisiae | chromosome XII sequence | CP006427.1 |
| Saccharomyces cerevisiae | chromosome XII sequence | CP006426.1 |
| Saccharomyces cerevisiae | chromosome XII sequence | CP006422.1 |
| Saccharomyces cerevisiae | chromosome XII sequence | CP006419.1 |
| Saccharomyces cerevisiae | chromosome XII sequence | CP006417.1 |
| Saccharomyces cerevisiae | chromosome XII sequence | CP006409.1 |
| Saccharomyces cerevisiae | chromosome XII sequence | CP006389.1 |
| Saccharomyces cerevisiae | chromosome XII sequence | CP006377.1 |
| Saccharomyces cerevisiae | chromosome XII sequence | CP020236.1 |
| Saccharomyces cerevisiae | chromosome XII sequence | CP006429.1 |
| Saccharomyces cerevisiae | chromosome XII sequence | CP006421.1 |
| Saccharomyces cerevisiae | chromosome XII sequence | CP006420.1 |
| Saccharomyces cerevisiae | chromosome XII sequence | CP006414.1 |
| Saccharomyces cerevisiae | chromosome XII sequence | CP006410.1 |
| Saccharomyces cerevisiae | chromosome XII sequence | CP011821.1 |
| Saccharomyces cerevisiae | chromosome XII sequence | CP006458.1 |
| Saccharomyces cerevisiae | chromosome XII sequence | CP006456.1 |
| Saccharomyces cerevisiae | chromosome XII sequence | CP006455.1 |
| Saccharomyces cerevisiae | chromosome XII sequence | CP006451.1 |
| Saccharomyces cerevisiae | chromosome XII sequence | CP006450.1 |
| Saccharomyces cerevisiae | chromosome XII sequence | CP006446.1 |
| Saccharomyces cerevisiae | chromosome XII sequence | CP006445.1 |
| Saccharomyces cerevisiae | chromosome XII sequence | CP006443.1 |
| Saccharomyces cerevisiae | chromosome XII sequence | CP006442.1 |
| Saccharomyces cerevisiae | chromosome XII sequence | CP006404.1 |
| Saccharomyces cerevisiae | chromosome XII sequence | CP006436.1 |
| Saccharomyces cerevisiae | chromosome XII sequence | CP006431.1 |
| Saccharomyces cerevisiae | chromosome XII sequence | CP006415.1 |
| Saccharomyces cerevisiae | chromosome XII sequence | CP006411.1 |
| Saccharomyces cerevisiae | chromosome XII sequence | CP006408.1 |
| Saccharomyces cerevisiae | chromosome XII sequence | CP009950.1 |
| Saccharomyces cerevisiae | chromosome XII sequence | CP008196.1 |
| Saccharomyces cerevisiae | chromosome XII sequence | CP020151.1 |
| Saccharomyces cerevisiae | chromosome XII sequence | CP008247.1 |
| Saccharomyces cerevisiae | chromosome XII sequence | CP008332.1 |
| Saccharomyces cerevisiae | chromosome XII sequence | CP008315.1 |
| Saccharomyces cerevisiae | chromosome XII sequence | CP008298.1 |
| Saccharomyces cerevisiae | chromosome XII sequence | CP008281.1 |
| Saccharomyces cerevisiae | chromosome XII sequence | CP008264.1 |
| Saccharomyces cerevisiae | chromosome XII sequence | CP008230.1 |
| Saccharomyces cerevisiae | chromosome XII sequence | CP008417.1 |
| Saccharomyces cerevisiae | chromosome XII sequence | CP008383.1 |
| Saccharomyces cerevisiae | chromosome XII sequence | CP008366.1 |
| Saccharomyces cerevisiae | chromosome XII sequence | CP008349.1 |
| Saccharomyces cerevisiae | chromosome XII sequence | CP008502.1 |
| Saccharomyces cerevisiae | chromosome XII sequence | CP008485.1 |
| Saccharomyces cerevisiae | chromosome XII sequence | CP008468.1 |
| Saccharomyces cerevisiae | chromosome XII sequence | CP008451.1 |
| Saccharomyces cerevisiae | chromosome XII sequence | CP008434.1 |
| Saccharomyces cerevisiae | chromosome XII sequence | CP008587.1 |
| Saccharomyces cerevisiae | chromosome XII sequence | CP008570.1 |
| Saccharomyces cerevisiae | chromosome XII sequence | CP008553.1 |
| Saccharomyces cerevisiae | chromosome XII sequence | CP008536.1 |
| Saccharomyces cerevisiae | chromosome XII sequence | CP008519.1 |
| Saccharomyces cerevisiae | chromosome XII sequence | CP008672.1 |
| Saccharomyces cerevisiae | chromosome XII sequence | CP008655.1 |
| Saccharomyces cerevisiae | chromosome XII sequence | CP008638.1 |
| Saccharomyces cerevisiae | chromosome XII sequence | CP008621.1 |
| Saccharomyces cerevisiae | chromosome XII sequence | CP008604.1 |
| Saccharomyces cerevisiae | chromosome XII sequence | CP008213.1 |
| Saccharomyces cerevisiae | chromosome XII sequence | CP008179.1 |
| Saccharomyces cerevisiae | chromosome XII sequence | CP008162.1 |
| Saccharomyces cerevisiae | chromosome XII sequence | CP008689.1 |
| Saccharomyces cerevisiae | chromosome XII sequence | CP008145.1 |
| Saccharomyces cerevisiae | chromosome XII sequence | CP008128.1 |
| Saccharomyces cerevisiae | chromosome XII sequence | CP008111.1 |
| Saccharomyces cerevisiae | chromosome XII sequence | CP008094.1 |
| Saccharomyces cerevisiae | chromosome XII sequence | CP008077.1 |
| Saccharomyces cerevisiae | chromosome XII sequence | CP008060.1 |
| Saccharomyces cerevisiae | chromosome XII sequence | CP008043.1 |
| Saccharomyces cerevisiae | chromosome XII sequence | CP008026.1 |
| Saccharomyces cerevisiae | chromosome XII sequence | CP008009.1 |
| Saccharomyces cerevisiae | chromosome XII sequence | CP007975.1 |
| Saccharomyces cerevisiae | chromosome XII sequence | CP007958.1 |
| Saccharomyces cerevisiae | chromosome XII sequence | CP007941.1 |
| Saccharomyces cerevisiae | chromosome XII sequence | CP007924.1 |

A lipase is an esterase that catalyzes the hydrolysis of fats, oils, and lipids. In one aspect, the gene that expresses lipase is isolated from a bacterium. In a further aspect, the bacterium is a *Micrococcus* species, a *Pseudomonas* species, a *Moraxella* species, or an *Acinetobacter* species. In a further aspect, the gene that expresses lipase has SEQ ID NO. 6 or at least 70% homology thereof, at least 75% homology thereof, at least 80% homology thereof, at least 85% homology thereof, at least 90% homology thereof, or at least 95% homology thereof. In a further aspect, the cellulose synthase is able to use mannose as a substrate instead of or in addition to glucose. In one aspect, the gene that expresses lipase can be positioned anywhere in the DNA construct disclosed herein. In one aspect, the gene that expresses lipase is positioned 5' (i.e., prior) to the gene that expresses chitin synthase.

Other sequences expressing lipase or related or homologous genes can be identified in a database such as, for example, GenBank. In one aspect, sequences useful herein include those with the GI numbers listed in Table 4:

TABLE 4

Lipase Genes

| Source Organism | Sequence Description | GI Number |
|---|---|---|
| *Micrococcus* sp. HL-2003 | lipase gene | AY268069.1 |
| *Pseudomonas* sp. | esterase gene | M68491.1 |
| *Moraxella* L1 | lipase 1 | X53053.1 |
| *A. calcoaceticus* | carboxylesterase and peptidyl prolyl-cis-trans-isomerase | X74839.1 |
| *Acinetobacter* sp. ADP1 | genomic DNA | CR543861.1 |
| *A. calcoaceticus* | esterase | X71598.1 |
| *Pseudomonas trivialis* | genomic DNA | CP011507.1 |
| *Pseudomonas azotoformans* | genomic DNA | CP019856.1 |
| *Pseudomonas extremaustralis* | genomic DNA | LT629689.1 |
| Pseudomonas fluorescens | genomic DNA | CP005975.1 |
| *Pseudomonas fluorescens* | genomic DNA | CP010896.1 |
| *Pseudomonas fluorescens* | genomic DNA | AF228666.1 |
| *Pseudomonas simiae* | genomic DNA | CP007637.1 |
| *Pseudomonas fluorescens* | genomic DNA | AM181176.4 |
| *Pseudomonas Antarctica* | genomic DNA | CP015600.1 |
| *Pseudomonas fluorescens* | genomic DNA | CP015639.1 |
| *Pseudomonas fluorescens* | genomic DNA | LT907842.1 |
| *Pseudomonas* sp. NS1 | genomic DNA | CP022960.1 |
| *Pseudomonas poae* | genomic DNA | LT629706.1 |
| *Pseudomonas poae* | genomic DNA | CP004045.1 |
| *Pseudomonas rhodesiae* | genomic DNA | LT629801.1 |
| *Pseudomonas trivialis* | genomic DNA | LT629760.1 |
| *Pseudomonas azotoformans* | genomic DNA | LT629702.1 |
| *Pseudomonas Antarctica* | genomic DNA | LT629704.1 |
| *Pseudomonas fluorescens* | genomic DNA | CP012400.1 |
| *Pseudomonas azotoformans* | genomic DNA | CP014546.1 |
| *Pseudomonas yamanorum* | genomic DNA | LT629793.1 |
| *Pseudomonas prosekii* | genomic DNA | LT629762.1 |
| *Pseudomonas koreensis* | genomic DNA | CP014947.1 |
| *Pseudomonas libanensis* | genomic DNA | LT629699.1 |
| *Pseudomonas* sp. GR 6-02 | genomic DNA | CP011567.1 |
| *Pseudomonas fluorescens* | genomic DNA | CP014868.1 |

TABLE 4-continued

Lipase Genes

| Source Organism | Sequence Description | GI Number |
| --- | --- | --- |
| Pseudomonas fluorescens | genomic DNA | CP011117.1 |
| Pseudomonas fluorescens | genomic DNA | S69066.1 |
| Pseudomonas cedrina | genomic DNA | LT629753.1 |
| Pseudomonas sp. bs2935 | genomic DNA | LT629744.1 |
| Pseudomonas fluorescens | genomic DNA | CP017296.1 |
| Pseudomonas sp. WCS374 | genomic DNA | CP007638.1 |
| Pseudomonas fluorescens | genomic DNA | CP003041.1 |
| Pseudomonas corrugate | genomic DNA | LT629798.1 |
| Pseudomonas corrugate | genomic DNA | CP014262.1 |
| Pseudomonas mediterranea | genomic DNA | LT629790.1 |
| Pseudomonas tolaasii | genomic DNA | CP020369.1 |
| Pseudomonas fluorescens | genomic DNA | CP015638.1 |
| Pseudomonas fluorescens | genomic DNA | CP015637.1 |
| Pseudomonas sp. TKP | genomic DNA | CP006852.1 |
| Synthetic construct | carboxylesterase | HM212419.1 |
| Synthetic construct | carboxylesterase | FJ213454.1 |
| Pseudomonas sp. FDAARGOS 380 | genomic DNA | CP023969.1 |
| Pseudomonas synxantha | genomic DNA | LT629786.1 |
| Pseudomonas orientalis | genomic DNA | LT629782.1 |
| Pseudomonas sp. URMO17WK12:I11 | genomic DNA | LN854573.1 |

In one aspect, the DNA construct has the following genetic components: a) a gene that expresses chitin synthase, b) a gene that expresses chitosanase, and c) a gene that expresses chitin deacetylase.

In an alternative aspect, the DNA construct has the following genetic components: a) a gene that expresses lipase, b) a gene that expresses chitin synthase, c) a gene that expresses chitosanase, and d) a gene that expresses chitin deacetylase.

In another aspect, said construct further includes a) a promoter, b) a terminator or stop sequence, c) a gene that confers resistance to an antibiotic (a "selective marker"), d) a reporter protein, or a combination thereof.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is an operon such as, for example, the LAC operon. As used herein, an "operon" is a segment of DNA containing a group of genes wherein the group is controlled by a single promoter. Genes included in an operon are all transcribed together. In a further aspect, the operon is a LAC operon and can be induced when lactose crosses the cell membrane of the biological device.

In one aspect, the regulatory sequence is a promoter. The term "promoter" refers to a DNA sequence capable of controlling the expression of a coding sequence. In another aspect, the coding sequence to be controlled is located 3' to the promoter. In still another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter also may be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, and GAL1 promoter. In a further aspect, the promoter is a native part of the vector used herein. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides from a ribosomal binding site. In another aspect, the promoter is positioned before the gene that expresses chitin synthase, the gene that expresses chitosanase, the gene that expresses chitin deacetylase, or any combination thereof.

In one aspect, the promoter is a GAL1 promoter. In another aspect, the GAL1 promoter is native to the plasmid used to create the vector. In another aspect, a GAL1 promoter is positioned before the gene that expresses chitin synthase, the gene that expresses chitosanase, the gene that expresses chitin deacetylase, the gene that expresses lipase (when used), or any combination thereof. In an another aspect, the promoter is a GAL1 promoter obtained from or native to the pYES2 plasmid.

In another aspect, the promoter is a T7 promoter. In a further aspect, the T7 promoter is native to the plasmid used to create the vector. In still another aspect, the GAL1 promoter is positioned before any or all of the genes in the construct, or is positioned before the LAC operon. In yet another aspect, the promoter is a T7 promoter obtained from or native to the pETDuet-1 plasmid.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is a T7 terminator. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated Enhancers may be located from about 1 to about 2000 nucleotides in the 5' direction from the start codon of the DNA to be transcribed, or may be located 3' to the DNA to be transcribed Enhancers may be "cis-acting," that is, located on the same molecule of DNA as the gene whose expression they affect.

In another aspect, the vector contains one or more ribosomal binding sites. As used herein, a "ribosomal binding site" is a sequence of nucleotides located 5' to the start codon of an mRNA that recruits a ribosome to initiate protein translation. In one aspect, the ribosomal binding site can be positioned before one or more or or all genes in the DNA construct, or a before a subset of genes in a DNA construct.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BasBI, NotI, XhoI, XphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA at a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior insertion into the plasmid. In a further aspect, a DNA ligase enzyme can be used to assist in the ligation process.

In another aspect, the ligation mix may be incubated in an electromagnetic chamber. In one aspect, the incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and commercially available. Such vectors include, but are not limited to, pWLneo, pSV2cat, pOG44, pXT1, pSG, pSVK3, pBSK, pYES, pYES2, pBSKII, pUC, pUC19, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copier per host cell and will contain selectable markers (such as genes for antibiotic resistance) to show the skilled artisan to select host eels that have been successfully transfected with the plasmids (for example, by growing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector, which confers antibiotic resistance, can survive. Optimally, only cells containing the vector to be expressed will be cultured, as this will result in the highest production efficiency of the desired gene products (e.g., peptides). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 4 or at least 70% homology thereto. The amount of fluorescence that is produced can be correlated to the amount of DNA incorporated into the transfected cells. The fluorescence produced can be detected and quantified using techniques known in the art. For example, spectrofluorometers are typically used to measure fluorescence.

The DNA construct described herein can be part of a vector. In one aspect, the vector is a plasmid, a phagemid, a cosmid, a yeast artificial chromosome, a bacterial artificial chromosome, a virus, a phage, or a transposon.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

In one aspect the construct includes from 5' to 3' the following genetic components in the following order: (1) a gene that expresses chitin synthase, (2) a gene that expresses chitosanase, and (3) a gene that expresses chitin deacetylase.

In one aspect the construct includes from 5' to 3' the following genetic components in the following order: a gene that expresses chitin synthase having SEQ ID NO. 1 or at least 70% homology thereto, a gene that expresses chitosanase having SEQ ID NO. 2 or at least 70% homology thereto, and a gene that expresses chitin deacetylase having SEQ ID NO. 3 or at least 70% homology thereto.

In another aspect the construct includes from 5' to 3' the following genetic components in the following order: (1) a GAL1 promoter, (2) a gene that expresses chitin synthase, (3) a CYC1 terminator, (4) a GAL1 promoter, (5) a gene that expresses chitosanase, (6) a CYC1 terminator, (7) a GAL1 promoter, (8) a gene that expresses chitin deacetylase, and (9) a CYC1 terminator.

In another aspect the construct includes from 5' to 3' the following genetic components in the following order: a GAL1 promoter, a gene that expresses chitin synthase having SEQ ID NO. 1 or at least 90% homology thereto, a GAL1 promoter, a gene that expresses chitosanase having SEQ ID NO. 2 or at least 90% homology thereto, a GAL1 promoter, and a gene that expresses chitin deacetylase having SEQ ID NO. 3 or at least 90% homology thereto.

In another aspect, the construct is a pYES2 plasmid having from 5' to 3' the following genetic components in the following order: a) a gene that expresses chitin synthase having SEQ ID NO. 1 or at least 70% homology thereto, b) a CYC1 terminator, c) a GAL1 promoter, d) a gene that expresses chitosanase having SEQ ID NO. 2 or at least 70% homology thereto, e) a CYC1 terminator, f) a GAL1 promoter, g) a gene that expresses chitin deacetylase having SEQ ID NO. 3 or at least 70% homology thereto, h) a CYC1 terminator, i) a GAL1 promoter, and j) a yellow fluorescent reporter protein having SEQ ID NO. 4 or at least 70% homology thereto, at least 75% homology thereto, at least 80% homology thereto, at least 85% homology thereto, at least 90% homology thereto, or at least 95% homology thereto.

In another aspect the construct includes from 5' to 3' the following genetic components in the following order: (1) a gene that expresses lipase, (2) a gene that expresses chitin synthase, (3) a gene that expresses chitosanase, and (4) a gene that expresses chitin deacetylase.

In one aspect the construct includes from 5' to 3' the following genetic components in the following order: (1) a gene that expresses lipase having SEQ ID NO. 6 or at least 70% homology thereto, (2) a gene that expresses chitin synthase having SEQ ID NO. 1 or at least 70% homology thereto, (3) a gene that expresses chitosanase having SEQ ID NO. 2 or at least 70% homology thereto, and (4) a gene that expresses chitin deacetylase having SEQ ID NO. 3 or at least 70% homology thereto.

In one aspect the construct includes from 5' to 3' the following genetic components in the following order: a gene that expresses chitin synthase having SEQ ID NO. 1 or at least 90% homology thereto, a gene that expresses chitosanase having SEQ ID NO. 2 or at least 90% homology thereto, and a gene that expresses chitin deacetylase having SEQ ID NO. 3 or at least 90% homology thereto.

In one aspect the construct includes from 5' to 3' the following genetic components in the following order: a gene that expresses lipase having SEQ ID NO. 6 or at least 90% homology thereto, a gene that expresses chitin synthase having SEQ ID NO. 1 or at least 90% homology thereto, a gene that expresses chitosanase having SEQ ID NO. 2 or at least 90% homology thereto, and a gene that expresses chitin deacetylase having SEQ ID NO. 3 or at least 90% homology thereto.

In another aspect the construct includes from 5' to 3' the following genetic components in the following order: a gene that expresses lipase having SEQ ID NO. 6 or at least 90% homology thereto, a GAL1 promoter, a gene that expresses chitin synthase having SEQ ID NO. 1 or at least 90% homology thereto, a GAL1 promoter, a gene that expresses chitosanase having SEQ ID NO. 2 or at least 90% homology thereto, a GAL1 promoter, and a gene that expresses chitin deacetylase having SEQ ID NO. 3 or at least 90% homology thereto.

In another aspect the construct includes from 5' to 3' the following genetic components in the following order: (1) a GAL1 promoter, (2) a gene that expresses lipase, (3) a GAL1 promoter, (4) a gene that expresses chitin synthase, (5) a CYC1 terminator, (6) a GAL1 promoter, (7) a gene that expresses chitosanase, (8) a CYC1 terminator, (9) a GAL1 promoter, (10) a gene that expresses chitin deacetylase, and (11) a CYC1 terminator.

In another aspect, the construct is a pYES2 plasmid having from 5' to 3' the following genetic components in the following order: a) a gene that expresses lipase having SEQ ID NO. 6 or at least 70% homology thereto, b) a CYC1 terminator, c) a GAL1 promoter, d) a gene that expresses chitin synthase having SEQ ID NO. 1 or at least 70% homology thereto, e) a CYC1 terminator, f) a GAL1 promoter, g) a gene that expresses chitosanase having SEQ ID NO. 2 or at least 70% homology thereto, h) a CYC1 terminator, i) a GAL1 promoter, j) a gene that expresses chitin deacetylase having SEQ ID NO. 3 or at least 70% homology thereto, k) a CYC1 terminator, l) a GAL1 promoter, and m) a yellow fluorescent reporter protein having SEQ ID NO. 4 or at least 70% homology thereto, at least 75% homology thereto, at least 80% homology thereto, at least 85% homology thereto, at least 90% homology thereto, or at least 95% homology thereto.

In another aspect the construct includes from 5' to 3' the following genetic components in the following order: (1) a gene that expresses lipase, (2) a gene that expresses chitosanase, (3) a gene that expresses chitin synthase, and (4) a gene that expresses chitin deacetylase.

In another aspect, the construct includes from 5' to 3' the following genetic components in the following order: (1) a gene that expresses lipase having SEQ ID NO. 6 or at least 70% homology thereto, (2) a gene that expresses chitonase having SEQ ID NO. 2 or at least 70% homology thereto, (3) a gene that expresses chitin synthase having SEQ ID NO. 1 or at least 70% homology thereto, and (4) a gene that expresses chitin deacetylase having SEQ ID NO. 3 or at least 70% homology thereto.

In another aspect, the construct includes from 5' to 3' the following genetic components in the following order: (1) a ribosomal binding site, (2) a gene that expresses lipase, (3) a ribosomal binding site, (4) a gene that expresses chitonase, (5) a T7 promoter, (6) a ribosomal binding site, (7) a gene that expresses chitin synthase, (8) a ribosomal binding site, and (9) a gene that expresses chitin deacetylase.

In another aspect, the construct includes from 5' to 3' the following genetic components in the following order: a gene that expresses lipase having SEQ ID NO. 6 or at least 90% homology thereto, a ribosomal binding site, a gene that expresses chitosanase having SEQ ID NO. 2 or at least 90% homology thereto, a T7 promoter, a LAC operon, a ribosomal binding site, a gene that expresses chitin synthase having SEQ ID NO. 1 or at least 90% homology thereto, a ribosomal binding site, and a gene that expresses chitin deacetylase having SEQ ID NO. 3 or at least 90% homology thereto.

In still another aspect, the construct is a pETDuet-1 plasmid having from 5' to 3' the following genetic components in the following order: a gene that expresses lipase having SEQ ID NO. 6 or at least 70% homology thereto, b) a ribosomal binding site, c) a gene that expresses chitosanase having SEQ ID NO. 2 or at least 70% homology thereto, d) a T7 promoter, e) a LAC operon, f) a ribosomal binding site, g) a gene that expresses chitin synthase having SEQ ID NO. 1 or at least 70% homology thereto, h) a ribosomal binding site, and i) a gene that expresses chitin deacetylase or at least 70% homology thereto, at least 75% homology thereto, at least 80% homology thereto, at least 85% homology thereto, at least 90% homology thereto, or at least 95% homology thereto.

Figure 1B:
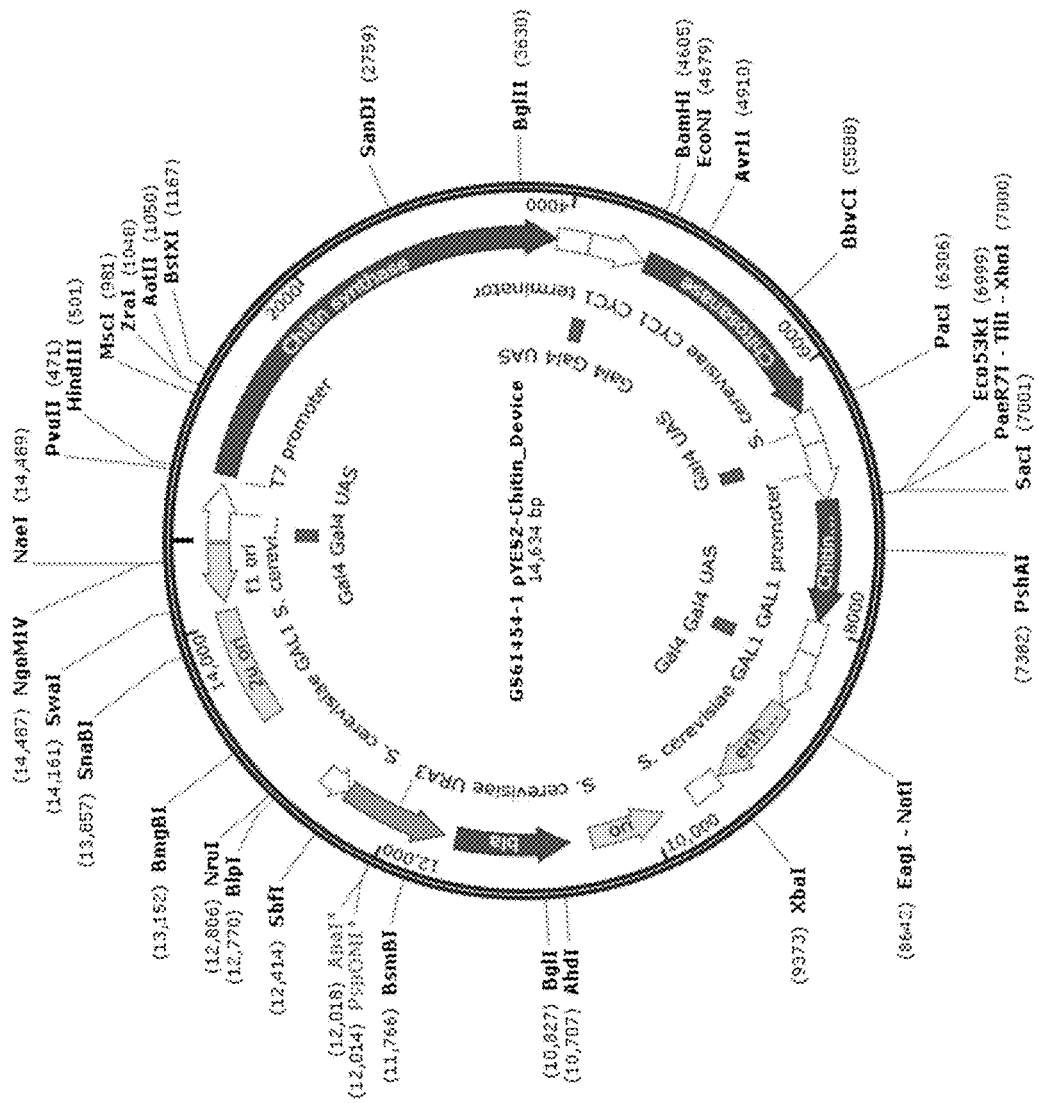
Figure 2A:
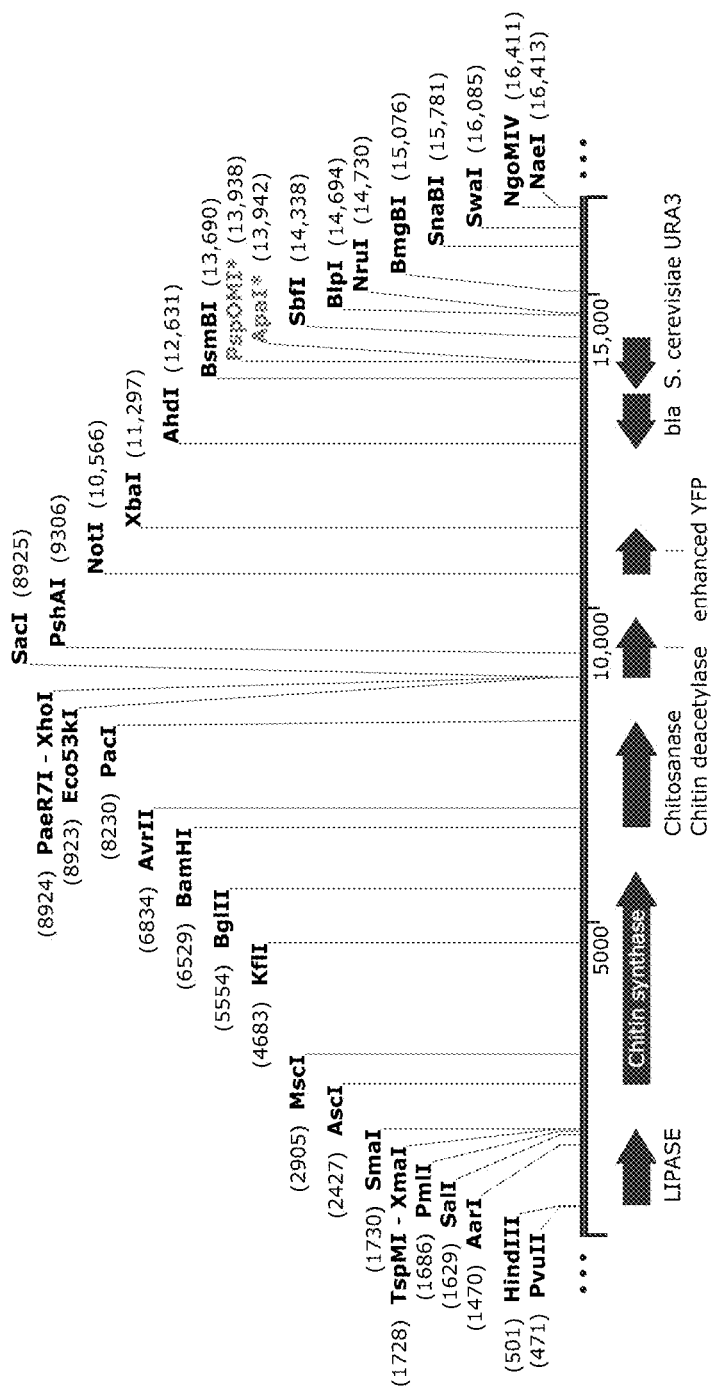
FIGS. 2A and 2B show, respectively, a linear and circular schematic of a constructed pYES2 plasmid showing the direction, placement, and size of genetic parts used of a second exemplary DNA device described herein.
Figure 2B:
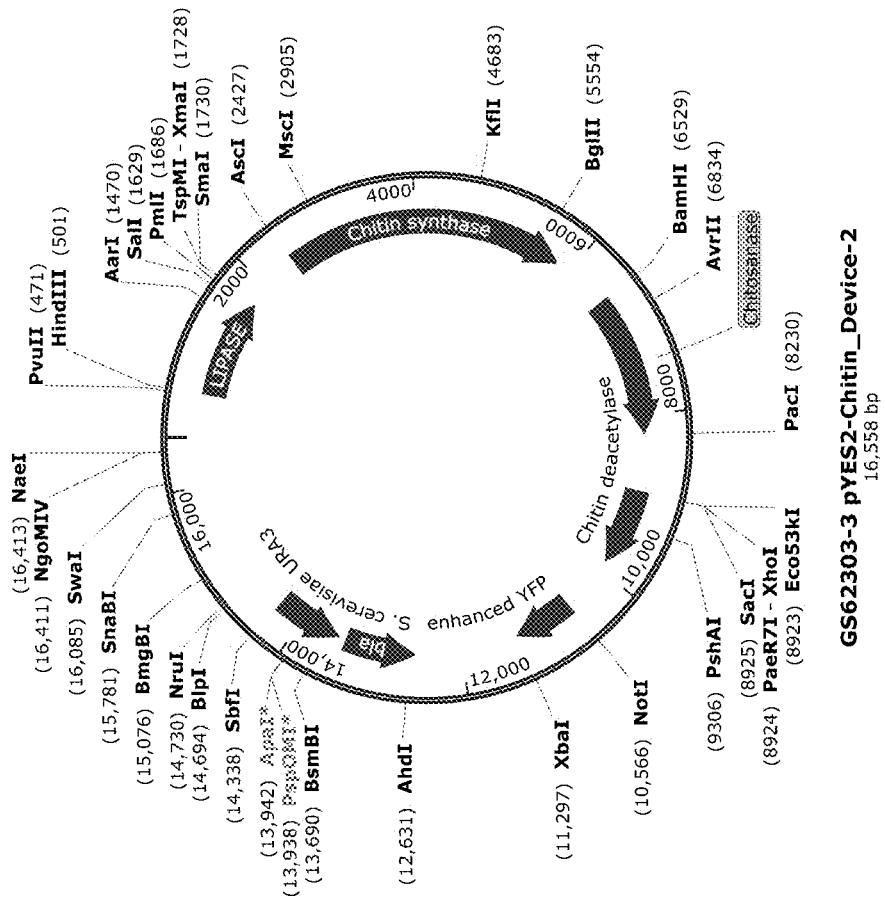
Figure 3A:
FIGS. 3A-D show the effect of extracts from the biological devices described herein on the retention of petroleum in sand.
Figure 3B:
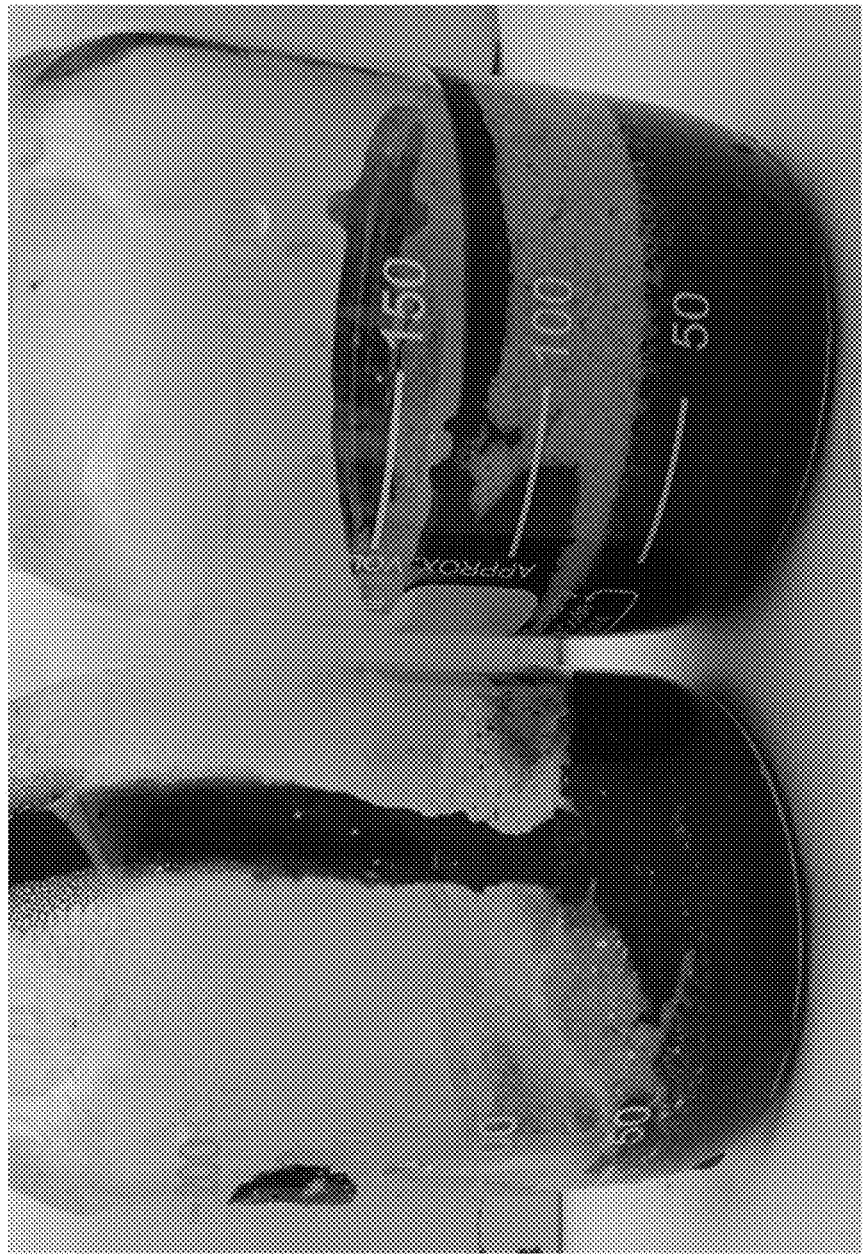
Figure 3C:
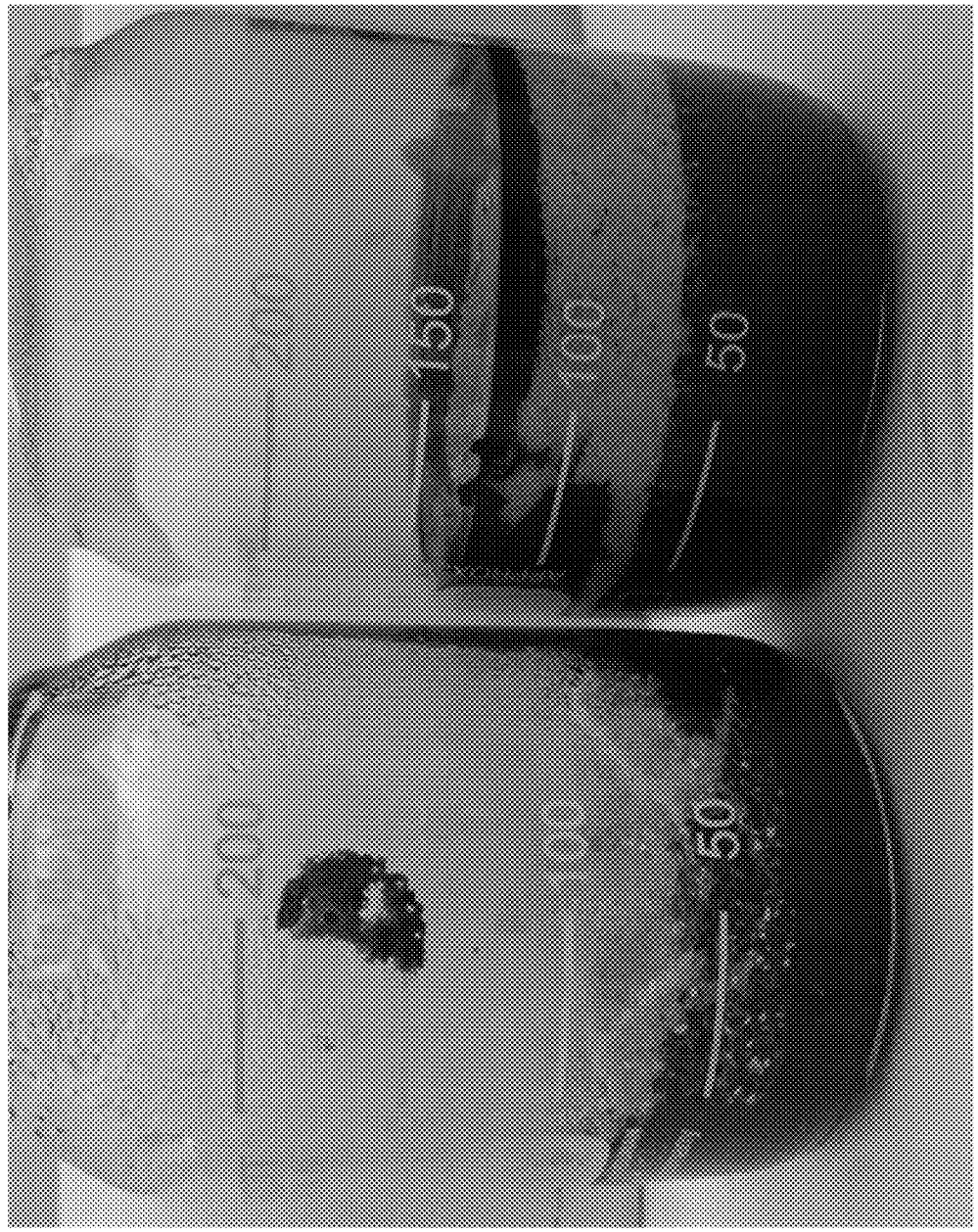
Figure 3D:
Figure 5A:
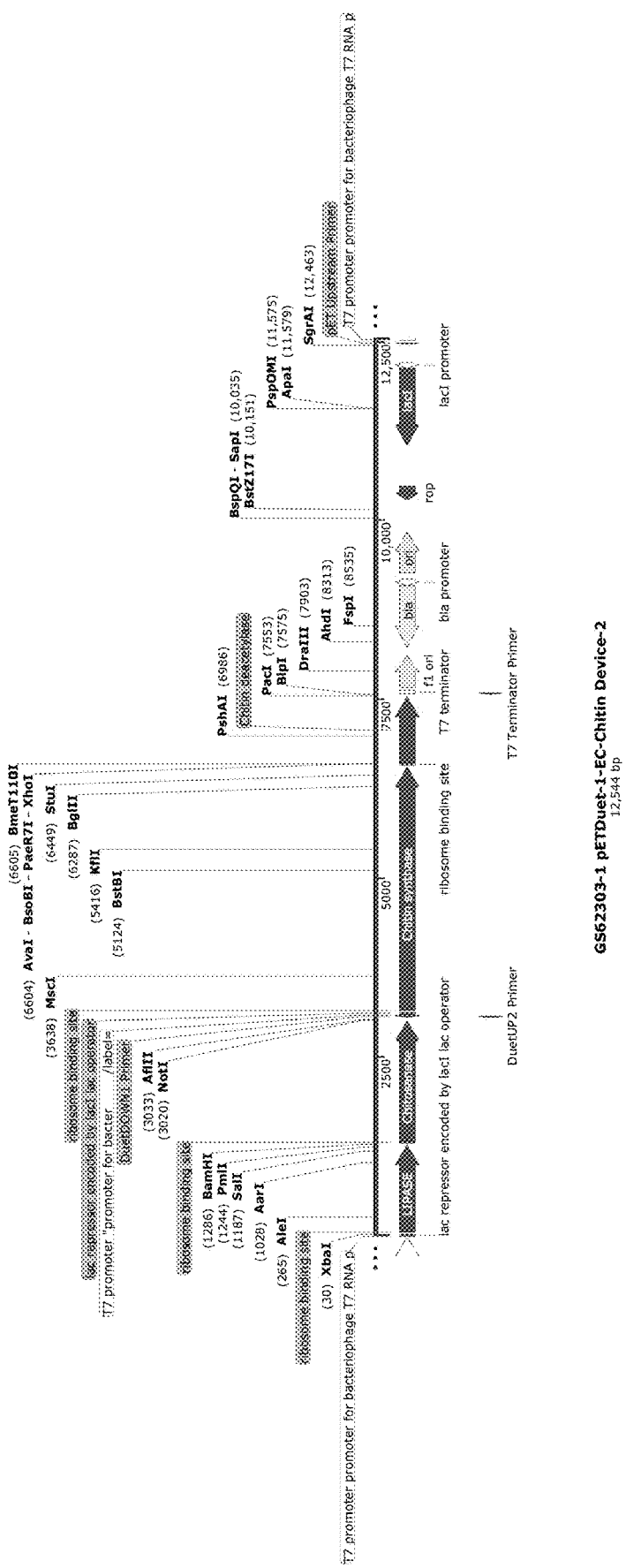
FIGS. 5A and 5B show, respectively, a linear and circular schematic of a constructed pETDuet-1 plasmid showing the direction, placement, and size of genetic parts used of an exemplary DNA device described herein.
Figure 5B:
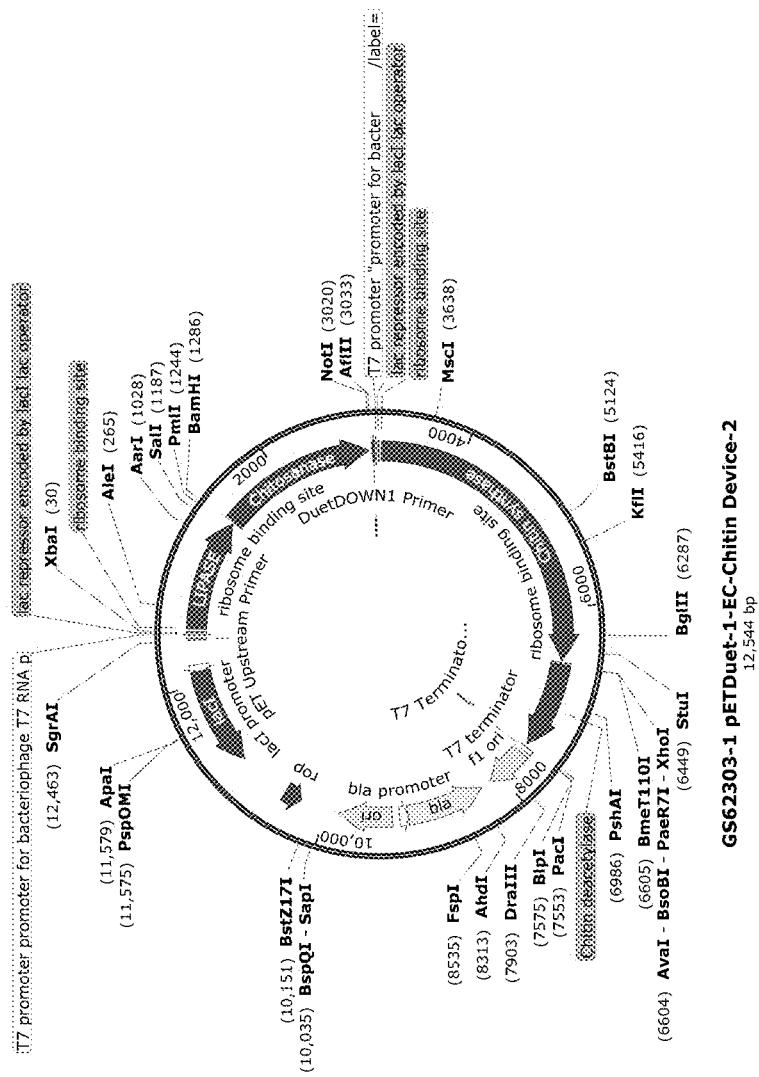

In another aspect, the DNA construct is SEQ ID NO. 5 or at least 90% homology thereof as depicted in FIGS. 1A and 1B. In another aspect, the DNA construct is SEQ ID NO. 7 or at least 90% homology thereof as depicted in FIGS. 2A and 2B. In yet another aspect, the DNA construct is SEQ ID NO. 8 or at least 90% homology thereof as depicted in FIGS. 5A and 5B.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce a polyactive carbohydrate.

"Heterologous" genes and proteins are genes and proteins that have been experimentally inserted into a cell that are not normally expressed by the cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which an exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

III. Preparation of Polyactive Carbohydrates

The biological devices described herein are useful in the production of polyactive carbohydrates. Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells can be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated and include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Culturing or fermenting of host cells can be accomplished by any technique known in the art. In one aspect, batch fermentation can be conducted. In batch fermentation, the composition of the culture medium is set at the beginning and the system is closed to future alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In one aspect, the method involves growing the biological devices described herein for a sufficient time to produce polyactive carbohydrates. The ordinary artisan will be able to choose a culture medium and optimum culture conditions based on the biological identity of the host cells.

IV. Extraction of Polyactive Carbohydrates

In certain aspects, after culturing the biological device to produce the polyactive carbohydrates, the host cells of the device can be lysed with one or more enzymes. For example, when the host cells are yeast, the yeast cells can be lysed with lyticase. In one aspect, the lyticase concentration can be 500, 600, 700, 800, 900, or 1000 µL per liter of culture, where any value can be the lower and upper endpoint of a range (e.g., 500 to 900 µL, 600 to 800 µL, etc.).

In addition to enzymes, other components can be used to facilitate lysis of the host cells. In one aspect, chitosan can be used in combination with an enzyme to lyse the host cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from 60% to about 100%, 80% to 90%, 75% to 85%, or about 80% acetylated. The molecular weight of the chitosan can vary, as well. For example, the chitosan can comprise about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, chitosan can be added until a concentration of 0.0015, 0.0025, 0.005, 0.0075, 0.01, 0.015, 0.02, 0.03, 0.04, or 0.05% (where any value can be a lower and/or upper endpoint of a range, e.g., 0.005 to 0.02, 0.0075 to 0.015, etc.) is achieved in the culture. Still further in this aspect, the chitosan is present at a concentration of 0.01%.

In a further aspect, the polyactive carbohydrates can be collected, separated from the microbial cells (lysed or intact), and/or purified through any technique known in the art such as, for example, precipitation, centrifugation, filtration, and the like. In one aspect, the polyactive carbohydrates can be purified via microfiltration to remove impurities. In one aspect, the microfilter has a pore size of 0.3, 0.35, 0.4, 0.45, 0.5, 0.55, 0.6, 0.65, 0.7, 0.75, or 0.8 µm, where any value can be a lower and/or upper endpoint of a range (e.g., 0.3 µm to 0.5 µm).

In another aspect, polyactive carbohydrates can be chemically-modified to produce additional desirable properties. Alternatively, compositions composed of the polyactive carbohydrates with lysed and/or intact host cells (e.g., yeast) can be used herein, where it is not necessary to separate the host cells and other components from the polyactive carbohydrate.

In one aspect, the polyactive carbohydrates can be produced in 24-48 hours from transformed host cells at a cost of approximately $0.50 per kilogram. In another aspect, the polyactive carbohydrates are provided in solution. In an alternative aspect, the polyactive carbohydrates are provided in powdered or dried form.

V. Use of Polyactive Carbohydrates in the Medical Industry

In one aspect, the polyactive carbohydrates produced by the devices described herein are useful in the medical industry. Further in this aspect, the polyactive carbohydrates can take any form that is suitable for the intended use such as, for example, sprays, liquids, gels, beads, nanoparticles, hydrogels, nanofibers, films, and/or nanogels. Still further in this aspect, various formulations of the polyactive carbohydrates can be incorporated into items designed for use in medical settings included, but not limited to, gauze pads and other wound dressings, bandages, membranes, and the like. Provided herein are also medical devices incorporating or coated with the polyactive carbohydrate.

In one aspect, wound dressings incorporating the polyactive carbohydrates maintain a moist environment at the wound interface, allow exchange of air around the wound site, absorb wound exudates, serve as a barrier to infectious microorganisms, are nonadherent and easily removable, and are non-toxic and non-allergenic.

In one aspect, the polyactive carbohydrates produced herein can promote wound and/or burn healing. In another aspect, the polyactive carbohydrates can promote blood clotting and can be used as hemostatic agents or incorporated into hemostatic bandages, wound dressings, and the like. In one aspect, the polyactive carbohydrates are mixed with absorbent materials and incorporated into wound dressings. In one aspect, the polyactive carbohydrates are incorporated into hydrogel-type bandages and can be used as wound dressings. In still another aspect, the polyactive carbohydrates can treat or prevent microbial and fungal infections of the skin. In yet another aspect, the polyactive carbohydrates can be used for transdermal drug delivery, temporary bone fillers, bioadhesives, and the like.

In one aspect, materials such as, for example, sponges or non-woven fabrics made from or incorporating the polyactive carbohydrate can be used as filling agents for surgical tissue defects, including at sites of tumor removal and at tissue abscesses. Further in this aspect, implantation of devices and objects incorporating the polyactive carbohydrate may prevent tumor recurrence in addition to promoting wound healing. Still further in this aspect, use of devices and objects incorporating the polyactive carbohydrate results in few to no side effects.

In another aspect, use of the polyactive carbohydrate may stimulate collagen synthesis, which is particularly important early in the wound healing process. In still another aspect, action of the polyactive carbohydrate may stimulate fibroblast proliferation, also important in the wound healing process. In yet another aspect, the polyactive carbohydrate does not stimulate the production of reactive oxygen species; this can be important to wound healing since reactive oxygen species are known to cause tissue and cell damage. In one aspect, use of the polyactive carbohydrate reduces the number of inflammatory cells surrounding a wound, which may also promote healing.

In one aspect, the polyactive carbohydrate may carry a net positive charge. Further in this aspect, the positive charge may interact with net negatively charged microbial membranes, causing increased membrane permeability and leakage of microbial cell constituents, leading to microbial cell death. In an alternative aspect, the charged polyactive carbohydrate may serve to keep microbial cells suspended rather than allowing them to form films and colonize surfaces. In a further aspect, the polyactive carbohydrate can be further derivatized such as, for example, through the addition of quaternary ammonium groups, in order to increase antimicrobial efficacy. In another aspect, metal ions such as, for example, silver, can be added to wound dressings and coverings incorporating the polyactive carbohydrate to increase antimicrobial efficacy. In still another aspect, another antimicrobial compound such as a topical antibiotic can be included in wound dressings incorporating the polyactive carbohydrate. In one aspect, provided herein is a method of reducing or preventing an infection in a subject, the method including the step of applying or administering to the subject the polyactive carbohydrate described herein. In a further aspect, the infection can be caused by a bacterium or a fungus. In a still further aspect, the polyactive carbohydrate can be applied topically to the skin of the subject. In another aspect, the polyactive carbohydrate can be applied to an open wound.

In a further aspect, the polyactive carbohydrate can be used in conjunction with another substance such as, for example, heparin. Further in this aspect, the polyactive carbohydrate can be used to treat burns and/or to prevent the extension of burns. In one aspect, a hydrogel incorporating the polyactive carbohydrate may be particularly useful as a wound dressing for burns.

The polyactive carbohydrate may also be used to treat surgical sites. In one aspect, the polyactive carbohydrate and dressings and products incorporating the same can be used to promote ordered tissue regeneration at surgical sites, thus reducing scarring.

In still another aspect, the polyactive carbohydrate may be used as an active agent or as a carrier to treat gum disease. In one aspect, the polyactive carbohydrate can be particularly useful in the treatment of chronic periodontitis. Further in this aspect, the polyactive carbohydrate can be used alone or in conjunction with standard treatments for periodontitis or other dental conditions. In one aspect, treatment with the polyactive carbohydrate can promote bone healing and prevent bone loss associated with periodontal disease.

In one aspect, provided herein are tissue adhesives incorporating the polyactive carbohydrate described herein. In a further aspect, the tissue adhesive can be used to promote wound closure and healing, can be used in the placement of implanted medical devices, or can be used in tissue engineering or bone and dental applications. In one aspect, tissue adhesives incorporating the polyactive carbohydrate are biocompatible and biodegradable as well as displaying strong and rapid adhesion when applied. In a further aspect, tissue adhesives incorporating the polyactive carbohydrate do not promote an immune reaction in the subject. In still a further aspect, the polyactive carbohydrate can be used as a scaffold for tissue engineering.

In another aspect, the polyactive carbohydrate produced herein can be used in various pharmaceutical applications. Further in this aspect, the net positive charge of the polyactive carbohydrate can increase adhesion to tissues and thus retention time of delivered molecules. Alternatively, the positive charge may be harnessed to form complexes of DNA or RNA with the polyactive carbohydrate for drug delivery purposes. In still another aspect, the polyactive carbohydrate has tunable drug delivery properties based on the pH of the pharmaceutical preparation and/or the surrounding tissue. In one aspect, the polyactive carbohydrate can be used in pharmaceutical preparations as an excipient to control factors such as, for example, dissolution of carried drug molecules.

In all of the above aspects, the subject can be a human or another mammal including animals commonly kept as pets (e.g., dogs and cats), livestock (e.g., horses, cattle, pigs, donkeys, sheep, goats, chickens, turkeys, oxen, etc.), zoo and circus animals (e.g., elephants, lions, tigers, giraffes, apes, monkeys, bears, rhinoceroses, etc.), and wild and/or game animals (e.g., deer, buffalo, ducks, geese, etc.).

VI. Antifungal and Antimicrobial Applications of Polyactive Carbohydrates

In one aspect, the polyactive carbohydrates can be used to coat items and articles or can be incorporated and dispersed throughout said items and articles. Further in this aspect, the presence of the polyactive carbohydrates may have antifungal properties that help to preserve the items and articles. In one aspect, the items and articles can be made of glass, fiberglass, plastic, metal, wood, fabric, foam, rubber, latex, silicone, or any combination thereof.

In a further aspect, the items and articles may be used in the construction and building industries in such applications as building materials, wood preservation, drywall, flooring, roofing materials and roofing membranes, artificial wood, plastic lumber, wood-filled plastics, decking, mobile homes, carpet, awnings, swimming pool liners, and related applications. In any of these applications, whether used as a coating or incorporated throughout the items and articles, the polyactive carbohydrates can help preserve the items by reducing or eliminating the growth of fungus and/or other microbes.

In still another aspect, the items and articles may be home goods or consumer goods such as, for example, garments and textiles, leather, footwear and shoe soles, security documents, art and décor, cushions, mattresses, bath and/or kitchen mats, shower curtains, leisure furniture, plastic mulch, and the like.

In yet another aspect, the items and articles can be used in the transportation and automotive industries including upholstery for vehicles such as automobiles, trucks, trains, buses, and boats. In a further aspect, the items and articles can be used in various applications in the shipping industry such as packaging materials, crates, and pallets that are resistant to fungal colonization.

In a related aspect, the polyactive carbohydrate can be incorporated into a paint, ink, dye, or stain. In some aspects, the paint, ink, dye, or stain can also include chitosan. When the paint, ink, dye, or stain is applied to a surface, the polyactive carbohydrate can impart antifungal properties to the surface. In one aspect, applying a paint, ink, dye, or stain containing the polyactive carbohydrate to the hull of a boat or other surface exposed to water can prevent or reduce the growth of barnacles. In another aspect, the polyactive carbohydrate or an extract of the biological devices can be applied along with chitosan to the surface exposed to water.

In still another aspect, the items and articles can be materials used in the manufacture of other goods. In this aspect, the items and articles can be plastic, coated fabrics, flexible films, foils or sheet, flexible extrusion products, products produced by injection molding, vinyl, gaskets, vinyl films or sheeting, plastisols, molded goods, or organosols. In yet another aspect, the items and articles can be artificial turf, parts such as, for example, filters used in air conditioning units, or materials intended for use in the oil and gas industries.

In all of the above aspects, incorporation of the polyactive carbohydrates prevents or inhibits fungal growth, thereby reducing odors, improving and maintaining the appearance of the items and articles, reducing decomposition, and maintaining a microbe-free environment.

VII. Personal Care, Grooming, Cosmetic, and Oral Care Compositions

In one aspect, provided herein are personal care products and compositions incorporating the polyactive carbohydrates described herein.

In one aspect, the polyactive carbohydrates described herein have antifungal and/or other antimicrobial properties. Further in this aspect, the polyactive carbohydrates can act as preservatives, extending the shelf lives of products by preventing microbial growth and spoilage. In an alternative aspect, personal care or grooming compositions containing the polyactive carbohydrates can have antimicrobial and/or antifungal activities when applied to the body such as, for example, antifungal nail enamel products or anti-acne cleansers or skin creams.

In another aspect, provided herein are oral care products containing the polyactive carbohydrates described herein. In one aspect, the oral care product can be a toothpaste, dental floss or floss pick, mouthwash, chewing gum, mouth guard or other appliance, or toothbrush. In a further aspect, for reusable oral care products such as toothbrushes and mouth guards, the polyactive carbohydrates can coat the surfaces of such products or be incorporated throughout the products. Further in this aspect, the polyactive carbohydrates can have antimicrobial and/or antifungal properties and can perform functions such as, for example, preventing the growth of mold or bacterial films when said products are stored for a period of time.

In an alternative aspect, for single-use and/or consumable oral care products such as toothpaste, dental floss or floss picks, mouthwashes, and chewing gums, the polyactive carbohydrates can be incorporated into the products and can be transferred to the user's mouth upon contact, thereby exerting antimicrobial and/or antifungal properties in the oral cavity. In some aspects, single-use and consumable oral care products may additionally be formulated with ingredients such as foaming agents, thickeners, fluoride, alcohol, and anti-cavity compounds such as the sugar alcohol xylitol in addition to the polyactive carbohydrates.

In one aspect, provided herein are antiperspirant and/or deodorant products containing the polyactive carbohydrate. Further in this aspect, the polyactive carbohydrate may absorb excess moisture and/or prevent the growth of bacteria that may cause body odor.

In still another aspect, provided herein are sunscreen products containing the polyactive carbohydrates described herein. Without wishing to be bound by theory, the polyactive carbohydrates increase the water-binding capacity of sun protective creams and/or increase the water-resistance of UV filtering compounds, thus allowing users of such products to delay reapplication of sun protective creams and other products longer than when using competing products not containing the polyactive carbohydrates.

Also provided herein are compounds, products, and compositions intended for use in the hair, wherein the hair products contain the polyactive carbohydrates described herein. In one aspect, the compositions may be applied to the hair to reduce static and/or to provide hold after or during styling in products such as, for example, hair spray or styling lotions. In another aspect, the polyactive carbohydrates can act as conditioning agents in shampoos, conditioners, permanent wave chemicals, styling lotions, and hair colorants.

Additionally, provided herein are cosmetics products containing the polyactive carbohydrates described herein. These include products such as, for example, nail enamel, foundation, eyeshadow, blush, bronzer, lipstick, and other color cosmetics.

In one aspect, the polyactive carbohydrates described herein can absorb metal ions. Further in this aspect, the absorption of metal ions may decrease skin irritation or toxicity. Thus, in one aspect, provided herein are compositions such as lotions, creams, gels, serums, powders, and the like, wherein the compositions contain the polyactive carbohydrates and can be applied to the skin to reduce irritation or other negative effects resulting from contact of metal ions with the skin.

In yet another aspect, the polyactive carbohydrates can be incorporated into compositions intended for caring for the skin of the face or the body. In one aspect, the polyactive carbohydrates aid in film formation or act as wetting agents or lubricants. Further in this aspect, the polyactive carbohydrate may help increase the water-binding capacity of preparations in which it is an ingredient. Still further in this aspect, compositions including the polyactive carbohydrate can act as moisturizing and/or repairing agents. In an alternative aspect, the polyactive carbohydrate may contribute to skin flexibility, elasticity, and smoothness, or may help to soften or texturize the skin. Thus, provided herein are humectants, wrinkle-fillers, moisturizers, anti-aging treatments, sunscreens, eye creams, body firming lotions, cleansers, and the like, all incorporating the polyactive carbohydrate described herein. In one aspect, these skin and body care compositions may include additional fragrances; in such case, in one aspect, the polyactive carbohydrate can act as a fixative to reduce evaporation of fragrance molecules from the body.

In another aspect, the polyactive carbohydrates described herein can be incorporated into any of the compositions described above in order to make the compositions more substantive or to thicken and stabilize the compositions.

In any of the above aspects, the compositions incorporating the polyactive carbohydrate can be formulated with other standard ingredients for such preparations including, but not limited to, fragrances and dyes or color agents, diluents, stabilizers, emollients, emulsifiers, surfactants, thickeners, texturizers, preservatives, humectants, or other physiologically acceptable ingredients.

XIII. Removal of Contaminants from Water

In some aspects, biological device concentration can be adjusted to an optimal density for removal of petroleum contaminants from water. In one aspect, device concentration is measured in a spectrophotometer and the optical density (OD) at 550-600 nm is adjusted to 0.5, 1, 1.5, or 2.0. In yet another aspect, incubation is carried out under aseptic conditions.

In one aspect, the petroleum-contaminated water is pretreated by admixing it with a surfactant. In a further aspect, this pretreatment homogenizes the petroleum-contaminated water. In another aspect, this pretreatment enhances the interaction between the biological devices and the water to be treated. In one aspect, the surfactant can be used at a concentration of about 0.1%, 0.2%, 0.4%, 0.6%, or 0.8% relative to the volume of the biological devices. In a further aspect, the surfactant is used at a concentration of 0.1%. In another aspect, the surfactant is DENVIRO FL-30 (DISAN®), polysorbate 20, or polysorbate 80. In still another aspect, the surfactant is mixed with the petroleum-contaminated water for about 1, 5, 10, 20, 30, or 60 minutes, or is mixed with the petroleum-contaminated water for about 12 or 24 hours, prior to contacting the petroleum-contaminated water with the biological devices.

In one aspect, the biological devices disclosed herein can be admixed with an aliquot of chitosan prior to contacting the petroleum-contaminated water. Further in this aspect, the aliquot of chitosan induces the immediate activity of the biological device.

In another aspect, 0.2, 0.5, 1, 2, 5, 10, 15, or 25 mL of the solution containing the biological device is added to the petroleum-contaminated water to make a total volume of 100 mL. In a further aspect, the mixture of petroleum-contaminated water and biological devices is incubated at about 20, 25, 28, 30, 35, or 40° C. while being shaken at 100, 110, 120, 150, or 180 rpm. In one aspect, the mixture is incubated at from 25-28° C. with shaking at from 110-120 rpm. In one aspect, 1 mL of biological device/chitosan is added to 99 mL of petroleum-contaminated water. For example, 0.900 mL to 0.999 mL of device and 0.100 to 0.001 mL of chitosan are used to treat petroleum-contaminated water.

In one aspect, the water to be treated is wastewater, well water, a municipal water supply, ground water, or a combination thereof that contains petroleum contaminants. In another aspect, the water to be treated is collected at or near a petroleum processing, storage, or transportation facility. Further in this aspect, the facility can be an oil well, a refinery, a bulk storage facility, a storage tank at a gas station, or a pipeline. In one aspect, the treated water is filtered after decontamination. In an alternative aspect, filtration is not required to separate the contaminants and/or biological devices from the treated water.

In one aspect, following incubation of the biological devices with the petroleum-contaminated water, pH of the solution is adjusted to a pH of from about 7 to about 9 and the pH-adjusted mixture is shaken for from 30-60 seconds. In a further aspect, pH-adjusted samples are then centrifuged. In one aspect, centrifugation occurs at 9000 rpm for 5 minutes at 10° C. In another aspect, the supernatant of the centrifuged solution contains decontaminated water and the pellet contains the biological devices and the contaminants. In this aspect, the supernatant can be decanted to separate the contaminants from the purified water.

In another aspect, at 15 minutes of treatment, about 80% of contaminants are removed from petroleum-contaminated water. In a further aspect, more than 90% of contaminants are removed from petroleum-contaminated water after 30 minutes of treatment.

In certain aspects, the compounds, compositions, and methods disclosed herein can optionally be used in conjunction with one or more additional water purification techniques. These techniques can include, for example, chlorination, aeration, coagulation, flocculation, sedimentation, filtration, decantation, desalination, boiling, autoclaving, distillation, UV irradiation, X-ray irradiation, ion exchange, reverse osmosis, ozonation, Fenton or photo-Fenton oxidation of organic compounds, iron precipitation, treatment with peroxides, or a combination thereof. In one aspect, the water to be treated herein can first be treated with the methods disclosed herein and then be treated using another technique. In an alternative aspect, the water to be treated herein can first be treated using one or more other techniques and can then be treated by the methods disclosed herein.

In some aspects, aliquots of water at various stages of treatment by the compounds, compositions, and methods disclosed herein can be assessed for the presence of petroleum-derived compounds and lipids. In one aspect, aliquots are withdrawn, mixed with benzene, and placed in a UV/visible spectrophotometer. In this aspect, absorbance at 280 nm can be used to quantify the concentration in ppm of petroleum-derived compounds remaining. Methods for determining concentration are known in the art and can be accomplished by a practitioner having ordinary skill in the art using only reasonable and routine experimentation.

In one aspect, the methods disclosed herein are used to treat petroleum-contaminated water prior to discharging it into the environment. In another aspect, the methods disclosed herein are used to treat water before it is used by humans or domestic animals.

In one aspect, a kit for removing petroleum contamination from water can be provided. In this aspect, the kit can contain at least the following elements: (a) a supply of biological devices capable of expressing the polyactive carbohydrates described herein and (b) a surfactant. In a further aspect, the biological devices can be provided in a freeze-dried form, in a frozen form, or in a liquid form. In an alternative aspect, the kit can contain: (a) the polyactive carbohydrates described herein and (b) a surfactant.

In another aspect, the biological devices and their products are useful in environmental remediation and cleaning applications not involving petroleum contaminants in water. In one aspect, the polyactive carbohydrate causes fine sediment particles to bind together, which allows subsequent removal through filtration. In another aspect, the polyactive carbohydrate can remove heavy metals, minerals, dyes, and oils from the water. In still another aspect, the polyactive carbohydrate can be used alone or in combination with bentonite, gelatin, silica gel, isinglass, or another fining agent to clarify alcoholic beverages such as wine, mead, and beer.

Additional applications can include, but are not limited to: removal of or reduction in levels of toxic metals and metal salts in soil and water; cleaning of spills of petroleum and petroleum derivatives including gasoline, diesel, motor oil, and the like, from soil; removal of environmental contamination due to laundry soaps; treatment of agricultural and industrial waste water; removal of dyes or colorings from waste water; and degreasing surfaces and/or environmental sites. In one aspect, the surface to be degreased is a natural surface such as stone, wood, compacted dirt, animal fur or feathers or skin, or the like. In another aspect, the surface to be degreased is a manmade surface such as, for example, glass or glassware, metal, concrete, asphalt, a building, a vehicle, oil drilling equipment, a road a path, a household object, or the like. In a further aspect, the fatty substance to be removed from the water or surface is a plant fat or animal fat such as, for example, food waste or cooking oil.

In the food industry, the polyactive carbohydrates produced herein can be used to degrease surfaces coated with cooking oils and fats. For example, frying pans and utensils coated with cooking oils and grease can be degreased with the polyactive carbohydrates. In other aspects, grease traps for collecting and storing cooking oil and grease can be degreased with the polyactive carbohydrates described herein.

In one aspect, the biological devices and their products described herein can be used to degrease water mixed with petroleum oil or another fatty substance. In another aspect, the biological devices and their products described herein can be used to degrease a surface coated with petroleum oil or another fatty substance. The term "degrease" as used herein is the ability of the carbo sugars described herein to remove petroleum oil or fatty substances from water or a surface. In one aspect, the biological devices and/or their products remove up to 50%, up to 60%, up to 70%, up to 80%, up to 90%, up to 95%, or up to 99% of the petroleum oil or fatty substances from water or the surface. In one aspect, biological devices expressing lipase can catalyze the hydrolysis of fatty substances contaminating water or a surface.

VIII. Polyurethanes and Biofoams

In another aspect, the polyactive carbohydrates described herein can be used to produce polyurethane compositions that have numerous applications.

In one aspect, the polyurethane composition is produced by:

a) admixing the polyactive carbohydrate produced herein and a natural oil polyol to produce a first admixture; and b) reacting the first admixture with a polyisocyanate to produce the polyurethane composition.

A "natural oil" as used herein is any oil extracted from a living organism. In one aspect, the living organism is a plant or alga. In a further aspect, the plant is the castor bean or castor oil plant (*Ricinus communis*). In another aspect, the living organism is an animal. In an alternative aspect, the living organism is a fungus. Natural oils can additionally contain triglycerides, fatty acids, fatty acid esters, sterols, isoprenoid or terpenoid compounds, alkaloids, phenols, and other metabolites.

"Natural oil polyols" are compounds that include at least one free hydroxyl group and are derived from or present in natural oils. A natural oil polyol may be naturally occurring, as with the ricinoleic acid in castor oil, or it may be chemically synthesized from an oil or fat containing one or more carbon-carbon double bonds. In one aspect, a natural fatty acid or triglyceride containing a carbon-carbon double bond is subjected to ozonolysis to cleave the double bond, followed by treatment with another molecule such as, for example, ethylene glycol, to form an alcohol. In another aspect, a natural fatty acid or triglyceride containing a carbon-carbon double bond can be epoxidized and treated with a nucleophile to generate an alcohol. In still another aspect, a natural fatty acid or triglyceride containing a carbon-carbon double bond can be formylated in the presence of carbon monoxide and hydrogen gas, followed by hydrogenation to generate a hydroxyl group. Other methods of producing natural oil polyols are also contemplated. Natural oils can be used as extracted or can optionally be purified. In one aspect, the natural oil polyol is or is derived from soy, a chemically-modified vegetable oil, a carbohydrate, lignin, cork, cashew nutshell liquid, *Lesquerella* oil, or a combination thereof. In one aspect, the natural oil polyol is castor oil. In another aspect, the natural oil polyol is ricinoleic acid. In still another aspect, the natural oil polyol is coriolic acid or a chemically-modified fatty acid.

"Castor oil" can optionally be extracted from the seeds of the castor oil plant. The primary component of castor oil is ricinoleic acid; minor components include oleic acid, linoleic acid, linolenic acid, stearic acid, palmitic acid, dihydroxystearic acid, and other trace fatty acids.

In one aspect, the natural oil polyol can include one or more hydroxyl fatty acids, which are defined herein as fatty acids having at least one free hydroxyl group. The hydroxyl fatty acid has the general formula R'C(O)OH, wherein R' is a saturated or unsaturated hydrocarbon chain having from 10 to 25 carbon atoms, and at least one hydroxyl group is covalently attached to a carbon atom of the hydrocarbon chain. The hydrocarbon can be linear or branched. In the case where the hydrocarbon is unsaturated, the hydrocarbon can have one carbon-carbon double bond or multiple carbon-carbon double bonds. Examples of monohydroxy fatty acids (i.e., one hydroxyl group present on the fatty acid) include, but are not limited to, hydroxynervonic acid, cerebronic acid, 10-hydroxy-20-decenoic acid, hydroxy-2-decenoic acid 10-phosphate, strophantus acid, lesquerolic acid, densipolic acid, auricolic acid, α-dimorphecolic acid, kamlolenic acid, 8-hydroxyoctadeca-9,11-diynoic acid, 8-hydroxyoctadeca-17-en-9,11-diynoic acid (isanolic), or 8-hydroxyoctadeca-13,17-dien-9,11-diyonic acid. Examples of polyhydroxy fatty acids (i.e., two or more hydroxyl groups) include, but are not limited to, axillarenic acid, tetrapedic acid, byrsonic acid, 9,10-dihyrdoxyoctadecanoic acid, phaseolic acid, phloionolic acid, Resolvin D1, 10,18S-docosatriene, or Resolvin E1. The hydroxyl fatty acids can be used as is in the natural oil (e.g., castor oil), isolated from a natural oil, or synthesized accordingly.

In certain aspects, a surfactant can be used to produce the polyurethane compositions described herein, where it is admixed with the polyactive carbohydrate and a natural oil polyol to produce a first admixture. A "surfactant" is an organic compound that may be derived from a natural product, or may result from chemical modification of a natural product, or may be completely chemically synthesized. Surfactants typically contain hydrophilic head groups and hydrophobic tails. In one aspect, the head group is anionic, cationic, non-ionic, or zwitterionic. In another aspect, the tail is composed of a hydrocarbon or a glucoside. Surfactants alter the surface tension of liquids and may form micelles or bilayers in aqueous solution. Many applications of surfactants are known in the art. Surfactants are, for example, commonly employed as emulsifiers, detergents, wetting agents, and the like.

Numerous cationic surfactants can be used in the compositions described herein. In one aspect, the cationic surfactant can be a quaternary ammonium salt.

Numerous zwitterionic surfactants can be used in the compositions described herein. In one aspect, the zwitterionic surfactant can be a lecithin such as soy lecithin; in another aspect, the zwitterionic surfactant can be a hydroxysultaine, a betaine, a sulfobetaine, or a mixture thereof. Among betaines, surfactants may be selected from the group comprising high alkyl betaines such as cetyl dimethyl carboxymethyl betaine, cocamidopropyl betaine, cocobetaine, coco dimethyl carboxymethyl betaine, lauryl amidopropyl betaine, lauryl bis-(2-hydroxyethyl) carboxymethyl betaine, laruyl bis-(2-hydroxypropyl)alpha-carboxyethyl betaine, lauryl dimethyl alphacarboxyethyl betaine, lauryl dimethyl carboxymethyl betaine, oleyl betaine, oleyl dimethyl gamma-carboxypropyl betaine, stearyl bis-(2-hydroxypropyl) carboxymethyl betaine, and mixtures thereof. Among sulfobetaines, surfactants may be selected from the group comprising coco dimethyl sulfopropyl betaine, lauryl bis-(2-hydroxyethyl) sulfopropyl betaine, lauryl dimethyl sulfoethyl betaine, stearyl dimethyl sulfopropyl betaine, and mixtures thereof. Amidobetaines and amidosulfobetaines are also contemplated.

Numerous nonionic surfactants can be used in the compositions described herein. Nonionic surfactants useful in the compositions described herein include alkoxylated fatty acid esters, alkyl glucosides, alkyl polyglucosides, amine oxides, alcohol ethoxylates, cocoamine oxide, glyceryl monohydroxystearate, glyceryl stearate, hydroxyl stearic acid, lauramine oxide, laureth-2, polyhydroxy fatty acid amides, polyoxyalkylene stearates, propylene glycol stearate, sorbitan monostearate, sucrose cocoate, sucrose esters, sucrose laurate, steareth-2, PEG-40 hydrogenated castor oil, and mixtures thereof. Preferred nonionic surfactants include those based on polyethoxylated sorbitan and oleic acid such as, for example, polysorbate 80 and polysorbate 20, both of which are available under a variety of trade names.

Further nonionic surfactants contemplated include, in one aspect, the condensation products of a higher aliphatic alcohol, such as a fatty alcohol, containing about 8 to 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij™ surfactants from ICI. Tergitol™ 15-S surfactants include $C_{11}$-$C_{13}$ secondary alcohol polyethylene glycol ethers, Brij™97 surfactant is polyoxyethylene(10) oleyl ether; Brij™58 surfactant is polyoxyethylene(20) cetyl ether; and Brij™76 surfactant is polyoxyethylene(10) stearyl ether.

In another aspect, a useful class of nonionic surfactants includes the polyethylene oxide condensates of one mole of alkyl phenol containing from about 6 to 12 carbon atoms in a straight or branched chain configuration, with about 3 to about 100 moles, preferably about 5 to about 40 moles, most preferably about 5 to about 20 moles of ethylene oxide to achieve the above defined HLB. Examples of nonreactive nonionic surfactants are the Igepal™ CO and CA series from Rhone-Poulenc. Igepal™ CO surfactants include nonylphenoxy poly(ethyleneoxy)ethanols. Igepal™ CA surfactants include octylphenoxy poly(ethyleneoxy)ethanols. Still another useful class of hydrocarbon nonionic surfactants includes block copolymers of ethylene oxide and propylene oxide or butylene oxide with HLB values of about 6 to about 19, preferably about 9 to about 18, and most preferably about 10 to about 16. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers. In other aspects, the nonionic surfactants include sorbitan fatty acid esters, polyoxyethylene sorbitan fatty acid esters and polyoxyethylene stearates having HLBs of about 6 to about 19, about 9 to about 18, and about 10 to about 16. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates. In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Numerous anionic surfactants can be used herein. In one aspect, the anionic surfactant can be alcohol phosphates and phosphonates, alkyl alkoxy carboxylates, alkyl aryl sulfates, alkyl aryl sulfonates, alkyl carboxylates, alkyl ether carboxylates, alkyl ether sulfates, alkyl ether sulfonates, alkyl phosphates, alkyl polyethoxy carboxylates, alkyl polyglucosides, alkyl polyglucoside sulfates, alkyl polyglucoside sulfonates, alkyl succinamates, alkyl sulfates, alkyl sulfonates, aryl sulfates, aryl sulfonates, fatty taurides, isethionates, N-acyl taurates, nonoxynol phosphates, octoxynol phosphates, sarcosinates, sulfated fatty acid esters, taurates, and mixtures thereof. Useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8) N-acyltaurine derivatives such as sodium N methyl-N-oleyltaurate); 9) amine oxides including alkyl and alkylamidoalkyldialkylamine oxides; and 10) alkyl phosphate mono or di-esters such as ethoxylated dodecyl alcohol phosphate ester, sodium salt. Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL™ A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the trade name AEROSOL™ OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and/or dodecylbenzenesulfonic acid sold under BIO-SOFT® AS-100 from Stepan Chemical Co. In one aspect, the surfactant can be a disodium alpha olefin sulfonate, which contains a mixture of $C_{12}$ to $C_{16}$ sulfonates. In one aspect, CALSOFT™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates. Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340KL from Clariant Corp., as well as PPG-5 cetyl 10 phosphate available under the trade designation CRODAPHOS™ SG from Croda Inc., Parsipanny, N.J. Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In one aspect, a surfactant is chosen based on its ability to form a stable emulsion containing an acidic aqueous solution of a polyactive carbohydrate and a natural oil polyol. In a further aspect, the concentration of surfactant can be from 0.001% to 1% (v/v), or can be about 0.001%, 0.005%, 0.01%, 0.05%, 0.1%, 0.35%, 0.5%, or 1% (v/v) with respect to the final emulsion volume. In another aspect, 0.35% of polysorbate 80 is used. In a further aspect, emulsion formation can be evaluated as a function of stirring time (e.g., about 1 minute, about 2 minutes, about 4 minutes, about 6 minutes, about 8 minutes, or about 10 minutes) and/or stirring speed (e.g., about 2000 rpm, about 5000 rpm, about 10,000 rpm, or about 20,000 rpm).

The order in which the polyactive carbohydrate and natural oil polyol can be admixed with one another to produce the first admixture can vary. In one aspect, the natural oil polyol can be added to a solution of the polyactive carbohydrate. In one aspect, the natural oil polyol is added over time (e.g., 2 minutes, 4 minutes, 5 minutes, 6 minutes, 8 minutes, or 10 minutes) with stirring (2000 rpm, 5000 rpm, 10,000 rpm, or 20,000 rpm) to create a final admixture that also incorporates the polyactive carbohydrate. In one aspect, the natural oil polyol is castor oil and stirring is conducted at 10,000 rpm for 5 minutes.

In one aspect, the polyactive carbohydrate is from 0.1 to 1% by weight of the first admixture. In another aspect, the amount of polyactive carbohydrate is 0.1, 0.2, 0.3, 0.4, 0.5, 0.6, 0.7, 0.8, 0.9, or 1 wt % of the first admixture, where any value can be a lower or upper endpoint of a range (2 g., 0.2 to 0.7, etc.). In another aspect, the polyactive carbohydrate can be prepared and used as a solution. In one aspect, the polyactive carbohydrate is an aqueous solution of 1% to 5% (v/v), where the first admixture includes 20% to 80% (v/v) of the aqueous solution of polyactive carbohydrate.

In one aspect, the natural oil polyol is from 20% to 80% (v/v) of the first admixture. In another aspect, the natural oil polyol is about 20%, 25%, 30%, 35%, 40%, 45%, 50%, 55%, 60%, 70%, 75%, or 80% (v/v) of the first admixture, where any value can be a lower or upper endpoint of a range (e.g., 40% to 60%, etc.).

Prior to the addition of the polyisocyanate, additional components can be added to the first admixture of polyactive carbohydrate and natural oil polyol. In one aspect, a catalyst can be added to the first admixture. A "catalyst" as used herein is any substance that can increase the rate of a chemical reaction. In one aspect, the catalyst is not consumed in the reaction. A single molecule of a catalyst can assist with multiple chemical reactions. Catalysts useful herein include, but are not limited to, tertiary amines such as dimethylethanolamine (DMAE), triethylenediamine (DABCO), 3-aminopropyldimethylamine (DMAPA), dimethylcyclohexylamine (DMCHA); compounds containing hydroxyl groups or secondary amines such as, for example, propylene glycol; metallic compounds including metal carboxylates such as, for example, dibutyltin dilaurate (DBTDL) as well as mercury, lead, bismuth, and zinc carboxylates; and other alkyl tin carboxylates, oxides, and mercaptides. In one aspect, the catalyst is added to an emulsion containing the polyactive carbohydrate and natural oil polyol at from about 0.05% to about 2% (v/v) with respect to the volume of the emulsion. In another aspect, about 0.05%, 0.1%, 0.15%, 0.2%, 0.25%, 0.4%, 0.6%, 0.7%, 0.8%, 1%, 1.2%, 1.5%, or 2% catalyst is used. In some aspects, a combination of catalysts is used. In one aspect, 0.5% (v/v) dibutyltin dilaurate and 1% (v/v) dimethylethanolamine were used in combination. In a further aspect, stirring is used to incorporate the catalyst throughout an emulsion containing the polyactive carbohydrate and natural oil polyol. In one aspect, different stirring times (e.g., about 1 minute, about 2 minutes, about 3 minutes, about 4 minutes, about 5 minutes, about 8 minutes, or about 10 minutes) and different stirring speeds (about 100 rpm, about 200 rpm, about 300 rpm, about 400 rpm, about 500 rpm, about 600 rpm, or about 700 rpm) are evaluated to determine the minimum stirring time and speed required to fully incorporate the catalyst into the emulsion. In one aspect, the emulsion and added catalyst are stirred at 300 rpm for 3 minutes.

In another aspect, a clay can be added to the first admixture. "Clay" and "clay minerals" as used herein refer to hydrous aluminum phylosilicates. Clays can optionally include oxides and/or chelates of other metals and semimetals such as, for example, silicon, iron, calcium, magnesium, sodium, potassium, and other alkali and alkaline earth metals. "Bentonite" is a category of impure clay that can consist of montmorillonite, kaolinite, and other species; and that can include potassium, sodium, calcium, aluminum, as well as other metals. "Zeolites" are microporous aluminosilicates that can accommodate a variety of cations, including, but not limited to, sodium, potassium, calcium, and magnesium. The cations in zeolites can be exchanged in aqueous solutions. Clays, bentonites, and zeolites can be used as sources of trace oxides and/or ions in the practice of the present invention. An "oxide" as used herein refers to a molecule, a network solid, or an ionic compound containing at least one oxygen atom and one other element. In one aspect, clays, bentonites, and zeolites contain chelated metal and semimetal ions. Not wishing to be bound by theory, the inclusion of the clay can be used to vary the pore size of the final biofoam product produced.

In one aspect, a metal or semimetal oxide or a chelated metal ion can be incorporated into the first admixture. In one aspect, the metal or semimetal oxide includes, for example, $Al_2O_3$, $Fe_2O_3$, MgO, CaO, $Na_2O$, $K_2O$, $SiO_2$, or a combination thereof. In this aspect, the metal or semimetal oxide can be introduced into the polyurethane compositions as a pure compound. In an alternative aspect, ions such as, for example, aluminum, iron (III), magnesium, calcium, sodium, potassium, silicon, and combinations thereof, can be incorporated into the polyurethane compositions described herein through the inclusion of clays or clay minerals. In one aspect, the metal or semimetal oxides or chelated metals are incorporated at concentrations of from about 0.02 nM to about 1.2 mM, or at 0.2 nM, 0.04 nM, 0.06 nM, 0.08 nM, 0.1 nM, 0.15 nM, 0.2 nM, 0.25 nM, 0.3 nM, 0.35 nM, 0.4 nM, 0.45 nM, 0.5 nM, 0.55 nM, 0.2 mM, 0.4 mM, 0.6 mM, 0.8 mM, or 1.2 mM.

In another aspect, one or more water-soluble metal salts can be incorporated into the first admixture. In one aspect, the water-soluble metal salts can include, for example, gallium (III) nitrate hydrate, zinc sulfate, zinc acetate, or a combination thereof. In one aspect, 50 mg/L of gallium (III) nitrate hydrate is incorporated into the emulsion containing the polyactive carbohydrate and natural oil polyol. In another aspect, 100 mg/L of zinc sulfate is incorporated into the emulsion containing the polyactive carbohydrate and natural oil polyol.

After preparation of the first admixture as described above, a polyisocyanate is added to the first admixture. "Polyisocyanates" as used herein are compounds with two or more —N=C=O groups. In one aspect, the polyisocyanate is an aliphatic diisocyanate, a cycloaliphatic diisocyanate, an aromatic diisocyanate, or an isomer thereof. In another aspect, the isocyanate or polyisocyanate is 2,4-toluenediisocyanate, 2,6-toluenediisocyanate, 4,4'-methylene diphenyl diisocyanate (MDI), 4,4'-methylenebis(cyclohexylisocyanate) (H12-MDI), 1-isocyanato-3-isocyanatomethyl-3,5,5-trimethylcyclohexane (isophorone diisocyanate), 2,4,4-trimethylhexamethylenediisocyanate, ethylidenediisocyanate, butylenediisocyanate, hexamethylenediisocyanate, cyclohexylene-1,4-diisocyanate, cyclohexylene-1,2-diisocyanate, 1-methyl-2,4-diisocyanato-cyclohexane, 1-methyl-2,6-diisocyanato-cyclohexane, naphtalene-1,5-diisocyanate, p-phenylendiisocyanate, tetramethyl-xylylenediisocyanate (TMXDI), or any combination thereof. The isocyanate or polyisocyanate can exist as one or more structural isomers. Alternatively, the isocyanate or polyisocyanate can be a dimer, trimer, or oligomer. In other aspects, the isocyanate or polyisocyanate can exist as one or more positional isomers. For example, the polyisocyanate can be a mixture of 2,4-toluenediisocyanate and 2,6-toluenediisocyanate. In a further aspect, the polyisocyanate can be a 65:35 mixture of 2,4-TDI and 2,6-TDI (i.e., TDI 65). In a different aspect, the polyisocyanate can be an 80:20 mixture of 2,4-TDI and 2,6-TDI (i.e., TDI 80). In an alternative aspect, the polyisocyanate is a modified MDI or polyphenylmethane polyisocyanate such as one of those sold by Yantai Wanhua Polyurethanes Co. under the trade name WANNATE®.

In one aspect, the polyisocyanate is added to the first admixture at different ratios such as, for example, about 1:1, about 1:2, about 1:3, about 1:4, about 1:5, about 1:6, about 1:7, or about 1:8 with respect to the total emulsion volume, or any range thereof (e.g., 1: to 1:8, 1:3 to 1:5, etc.). In this aspect, polymerization reactions can then be carried out. Different reaction times (e.g. 8 minutes, 10 minutes, 12 minutes, 15 minutes, or 20 minutes) and stirring speeds (e.g., 500 rpm, 600 rpm, 700 rpm, 800 rpm, 900 rpm, or 1000 rpm) can be evaluated to determine the optimum reaction time and stirring speed. In one aspect, the first admixture is admixed with the polyisocyanate for 10 minutes at 500 rpm. In another aspect, the reaction is conducted at room temperature.

Upon admixing the components in the first admixture with the polyisocyanate, isocyanate-reactive functional groups present on the polyactive carbohydrate and/or natural oil polyol react with the isocyanate groups on the polyisocyanate to produce a polyurethane. Here, a polymer composed of organic residues joined by urethane linkages is produced. Although the components in the first admixture include hydroxyl groups, other components may be present that include other isocyanate-reactive functional groups such as amine groups, thiol groups, or other nucleophilic groups capable of reacting with isocyanate groups.

The polyurethane compositions described herein can be used to produce biofoams that nave numerous applications. The term "biofoam" as used herein is any substance formed when pockets of gas have been trapped in a solid or liquid. In one aspect, the biofoams produced herein can exist as an emulsion or dispersion at room temperature. In other aspects, the biofoams produced herein are solid materials at room temperature.

The amount of the polyactive carbohydrate present in the final biofoam product can vary. In one aspect, the amount of polyactive carbohydrate present in the biofoam is from 0.005% to 0.1% by weight of the biofoam. In another aspect, the amount of polyactive carbohydrate present in the biofoam is about 0.005%, 0.01%, 0.02%, 0.03%, 0.04%, 0.05%, 0.06%, 0.07%, 0.08%, 0.09%, or 0.1% by weight of the biofoam, where any value can be a lower and/or upper endpoint of a range (e.g., 0.01% to 0.05%). When used to prepare the biofoams, the polyactive carbohydrate can be prepared as a stock solution. For example, the polyactive carbohydrate in powder form (0.05, 0.1, 0.2, 0.3, 0.4, 0.5, 0.6, 0.7, 0.8, 0.9, or 1 g) can be added to water (100 mL to 1 L) to produce a stock solution. The pH of the stock solution can be adjusted as necessary.

The selection and amounts of reactants as well as processing conditions will determine the physical state of the biofoams. For example, by varying the amount of the polyactive carbohydrate relative to the amount of castor oil it is possible to produce soft and hard biofoams. In one aspect, when the polyisocyanate is admixed with the first admixture, a solid biofoam is produced. The polyurethane compositions produced herein can be poured into a mold of any desired shape. If necessary, the mold containing the polyurethane composition can be placed in an oven to remove residual solvent and produce the final biofoam.

In other aspects, one or more blowing agents can be incorporated into the polyurethane compositions to produce the biofoams. A blowing agent can be physical or chemical in nature. A "physical blowing agent" is a gas or low boiling point liquid which expands due to heat generated by the polyurethane-forming reaction, thus forming bubbles and creating foam. A "chemical blowing agent" is a compound or substance that reacts to form a gas. In one aspect, the blowing agent is a physical blowing agent. Physical blowing agents include compounds such as, for example, hydrofluorocarbons (HFCs), hydrocarbons (HCs), hydrofluoroolefins, liquid $CO_2$, and other low boiling point liquids. In one aspect, the physical blowing agent is HFC-134a (1,1,1,2-tetrafluoroethane), HFC-245fa (pentafluoropropane), HFC-365mfc (1,1,1,3,3-pentafluorobutane), HFC-152a (1,1-difluoroethane), formic acid, methyl formate, HFO-1234ze (1,3,3,3-tetrafluoropropene), cyclopentane, n-pentane, iso-pentane, iso-butane, acetone, dichloromethane, or a mixture thereof. In another aspect, the blowing agent is a chemical blowing agent. In one aspect, the chemical blowing agent is carbon dioxide produced by the reaction of isocyanate groups with water. In a further aspect, both chemical and physical blowing agents can be used.

In other aspects, the biofoams include additional additives not already described above such as, for example, flame retardants, color additives, release agents, biocides, other additives, or a combination thereof. The additional components can be admixed with a dispersion or emulsion of polyurethane composition in order incorporate the additives throughout the biofoam. In the alternative, the additives can be applied to the surface of the solid biofoam.

In another aspect, after the preparation of the biofoam, the biofoam can contain residual solvent (e.g., water). In certain aspects, it is desirable to remove all or substantially all (e.g., greater than 70%, greater than 80%, greater than 90%, greater than 95%, greater than 99%, or 100%) of the solvent in the biofoam. In one aspect, drying of the biofoams can be accomplished in an oven at about 20° C., 30° C., 40° C., 50° C., 60° C., or about 70° C. In one aspect, the biofoams are dried in an oven at 50° C. In a further aspect, the biofoams can be dried for from about 0.5 to about 100 hours, or for about 72 hours. In one aspect, removal of water from biofoams is assessed by periodically removing the biofoams from the oven and weighing them. When the biofoams have the same weight at, for example, at least 2 or 3 successive weighings separated by several hours, the biofoams can be considered to be dry and can be removed from the oven.

The biofoams produced herein have several beneficial properties. In one aspect, the biofoams are resistant to discoloration. In another aspect, discoloration of the biofoams can be assessed by exposing the biofoams to an agent known to cause stains. In a further aspect, the agent known to cause stains is, for example, tea, coffee, or red wine. In one aspect, the biofoams can be submersed in coffee for a period of up to about 24 hours. In this aspect, after 24 hours, the biofoams are removed from the coffee and rinsed with water. Discoloration can then be qualitatively assessed as, for example, weak, medium, or strong.

In another aspect, the biofoams are resistant to acid degradation. For example, the biofoam can be assessed by placing a piece of the foam in an aqueous solution of an acid for 24 or 48 hours. In a further aspect, the acid is present at a 0.1N concentration. In another aspect, the acid is an organic acid such as, for example, acetic acid or formic acid. In an alternative aspect, the acid is an inorganic acid such as, for example, nitric acid, hydrochloric acid, phosphoric acid, or sulfuric acid. Resistance to mixtures of acids can also be tested. In a further aspect, photographs of the foam before and after exposure to acid can be compared to qualitatively assess acid resistance. In another aspect, the foam can be weighed before and after acid exposure to assess whether material has been lost.

In one aspect, it is desirable to know the maximum temperature to which the biofoams can be exposed without decomposition. This is known as temperature resistance. In one aspect, decomposition due to heat exposure can be assessed by placing a piece of the foam in an oven at a temperature of from about 50° C. to about 120° C. In a further aspect, temperature resistance is assessed at about 50° C., at about 80° C., or at about 120° C. In certain aspects, pieces of biofoam can be placed in an oven and the internal temperatures of the biofoam pieces can be measured periodically with, for example, a thermometer or a thermocouple. In a further aspect, temperature resistance can be measured every 10 minutes for up to one hour. In one aspect, the biofoam samples can be weighed prior to assessing temperature resistance, and can be weighed periodically to evaluate the level of decomposition. In this aspect, samples can be weighed every 10 minutes for up to one hour, at about the same time the internal temperature of the biofoam pieces is being measured, with weight loss indicating that decomposition has occurred. In an additional aspect, temperature resistance can be qualitatively assessed by, for example, visually noting any discoloration of the biofoam samples that occurs subsequently to heat treatment. In one aspect, if a sample exhibits less than about 20% weight loss, or less than about 10% weight loss, after exposure to a particular temperature, the sample can be said to be temperature resistant. In another aspect, if a sample does not become visibly discolored after exposure to a particular temperature, the sample can be said to be temperature resistant.

In one aspect, it is desirable to assess the biofoams for recovery from deformation. In this aspect, pressure can be applied to the biofoams, causing deformation. Also in this aspect, when pressure is removed from the biofoams, the biofoams can return to their original shapes and/or sizes. In certain aspects, from about 0.5 bars to about 1 bar of pressure are applied. In other aspects, the time required for the biofoams to recover from deformation is measured. In one aspect, the biofoams take up to about 5 seconds to recover from deformation. In another aspect, the biofoams take from about 1 second to about 3 seconds to recover from deformation.

In one aspect, provided herein are articles composed of or including the biofoams described herein. The biofoams produced herein can be used in any application where soft synthetic polyurethane foams are used. For example, the biofoams can be used in upholstery such as cushions, pillows, furniture, or mattresses, including in automobiles, trains, watercraft and boats, and aircraft. In another aspect, the biofoams can be used to produce equipment for exercise or physical therapy including, for example, yoga mats and other floor mats, padding or upholstery for weight machines and seating for stationary and street bicycles, foam balls for physical therapy, comfort grips for handles for weights, kettlebells, bicycles, and the like, helmet padding and other personal protective equipment, and similar applications. In still another aspect, the biofoams can be used in the construction industry such as for insulation, carpet padding or carpet underlay materials, and materials useful in soundproofing rooms. In another aspect, the biofoams can be used to create packaging materials including anti-static cushioning, case inserts, pads for vibration control, camping pads, and the like.

In another aspect, the biofoams disclosed herein can be used in the medical industry. In one aspect, the biofoam can be used where it is desirable to reduce or minimize blunt force or trauma to a subject. For example, the polyurethane composition can be injected between the skin of the subject and a cast to produce a biofoam that can further prevent any applied force to the broken bone of the subject. In certain aspects, the polyurethane composition can include antimicrobial agents in order to prevent odor.

In other aspects, the polyurethane compositions described herein can be used as adhesives. For example, the polyurethane composition can be in a sufficient amount of solvent so that it can readily be applied to the surface of a substrate (e.g., spray coating, dipping, brushing). Upon removal of the solvent a biofoam is produced, which results in the formation of a strong bond between to substrates. In other aspects, the polyurethane compositions can be used to seal cracks and holes. Here, the polyurethane composition is sprayed in a hole or crack then forms a biofoam.

IX. Methods for Enhancing the Physiological Properties of Plants

The devices and methods described herein can enhance the physiological properties of a plant. The term "physiological property" as defined herein includes any physical, chemical, or biological feature that is improved using the devices and methods described herein. In one aspect, the devices and methods can enhance the growth rate of the plant. In some aspects, the devices and methods can enhance the plant's ability to kill fungal cells or resist fungal infection. These are just some of the physiological properties that are enhanced using the devices and methods described herein.

As used herein, "plant" is used in a broad sense to include, for example, any species of woody, ornamental, crop, cereal, fruit, or vegetable plant, as well as photosynthetic green algae. "Plant" also refers to a plurality of plant cells that are differentiated into a structure that is present at any stage of the plant's development. Such structures include, but are not limited to, fruits, shoots, stems, leaves, flower petals, roots, tubers, corms, bulbs, seeds, gametes, cotyledons, hypocotyls, radicles, embryos, gametophytes, tumors, and the like. "Plant cell," "plant cells," or "plant tissue" as used herein refer to differentiated and undifferentiated tissues of plants including those present in any of the tissues described above, as well as to cells in culture such as, for example, single cells, protoplasts, embryos, calluses, etc.

In one aspect, provided herein is a method for producing one or more polyactive carbohydrates from plant cells, the method involves contacting the plant cells with the biological device disclosed herein. In one aspect, when the polyactive carbohydrate comes into contact with the plant cell, the polyactive carbohydrate can influence the molecular biology of the plant cell by targeting, for example, the plasma membrane of the cell or the chromatin/DNA in the cell nucleus. This, in turn, can alter concentration of metabolites or ions (e.g., calcium) in the cell, structural stability of the cell, or expression of cellular DNA that is later translated into proteins involved in protection against reactive oxygen species, against pathogenetic microorganisms, and the like.

The selection of the plant used in the methods described herein can vary depending on the application. For example, a specific plant can be selected that produces certain desirable metabolites. Current techniques for producing most plant metabolites are expensive. For example, large amounts of fresh plant biomass must be cultivated and harvested and expensive and time-consuming extraction methods must be used. The biological devices and methods described herein enhance the production of metabolites from plants that naturally produce those metabolites.

In one aspect, plant cells when contacted with the biological devices described above exhibit enhanced production of various desirable metabolites. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescences, seedling apical meristems, microspores, and the like. Those cells that are capable of proliferating as callus are also useful herein. Methods for growing plant cells are known in the art (see U.S. Pat. No. 7,919,679). In one aspect, plant calluses grown from 2 to 4 weeks can be used herein. The plant cells can also be derived from plants varying in age. For example, plants that are 80 days to 120 days old after pollination can be used to produce calluses useful herein.

The plant cells can be contacted with the biological device in a number of different ways. In one aspect, the device can be added to media containing the plant cells. In another aspect, the device can be injected into the plant cells via syringe. The amount of device and the duration of exposure to the device can vary as well. In one aspect, the concentration of the device is about $10^3$, $10^4$, $10^5$, $10^6$, $10^7$, $10^8$, or $10^9$ cells/mL of water. In one aspect, when the host cell is a bacterium, the concentration of the device is $10^6$. In another aspect, when the host cell is yeast, the concentration of the device is $10^9$. Different volumes of the biological device can be used as well, ranging from 5 μL to 500 μL.

Once the plant cells have been in contact with the biological device for a sufficient time to produce the metabolite, the metabolite is isolated. In one aspect, the metabolite is extracted from the media containing the biological device and the plant cells. The selection of extraction solvent can vary depending upon the solubility of the metabolite.

With current techniques, the extraction of metabolites produced from plants usually requires high initial amounts of plant biomass or material, which in turn requires larger amounts of extraction solvents. The use of higher amounts of extraction solvents adds to the expense of metabolite production. The use of higher amounts of organic solvents presents environmental risks as well. However, the use of the biological devices described herein produces significantly higher amounts of metabolites such as polyactive carbohydrates, which means smaller amounts of biomass are required in order to produce and isolate the metabolites when compared with existing techniques. The extraction of plant metabolites using current techniques also requires fresh biomass, which entails agronomic practices, the use of chemicals, and time-consuming extraction methods. Therefore, the use of the biological devices described herein is more cost-effective and safer for the environment than traditional methods for producing and synthesizing polyactive carbohydrates. Furthermore producing polyactive carbohydrates in a laboratory setting removes the need to source them from the natural environment, leading to a reduction in harmful practices such as, for example, beach modification, accumulation of industry debris, and reduction of biodiversity that are associated with commercial shellfish aquaculture.

In other aspects, the devices and methods described herein can increase the growth rate of a plant. In particular, the devices and methods described herein are effective in accelerating plant development in the early stages of tissue culturing. By accelerating plant development in the early stages, it is possible to harvest more metabolites from the plant. Additionally, the devices and methods described herein protect plant tissue cultures against microbial contamination, which is a problem associated with tissue culturing. Finally, traditional methods for tissue culture involve the use of synthetic growth factors such as 2,4-dichlorophenoxyacetic acid (2,4-D), which can pose environmental concerns. The devices and methods described herein avoid the need for such compounds.

In certain aspects, any of the biological devices described above can be used in combination with a polysaccharide to enhance one or more physiological properties of the plant. In one aspect, the plant cells are first contacted with the biological device, then subsequently contacted with the polysaccharide. In another aspect, the plant cells are first contacted with the polysaccharide, then subsequently contacted with the biological device. In a further aspect, the plant cells are only contacted with a polysaccharide and not contacted with the biological device. In a still further aspect, the plant cells are contacted simultaneously with the polysaccharide and the biological device.

In one aspect, the polysaccharide includes chitosan, glucosamine (GlcN), N-acetylglucosamine (NAG), or any combination thereof. Chitosan is generally composed of GlcN and NAG units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, chitosan isolated from shells of crab, shrimp, lobster, and/or krill is useful herein. In one aspect, the chitosan is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.01% to 0.01% by weight, from 0.075% to 0.025% by weight, or is about 0.05% by weight. The polysaccharides used here are generally natural polymers and thus present no environmental concerns. Additionally, the polysaccharides can be used in acceptably low concentrations. In certain aspects, however, the polysaccharides can be used in combination with one or more plant growth regulators.

In one aspect, the plant growth regulator is an auxin, a cytokinin, a gibberellin, abscisic acid, or a polyamine. In a further aspect, the auxin is a natural or synthetic auxin. In a still further aspect, the auxin is indole-3-acetic acid (IAA), 4-chloroindole-3-acetic acid (4-Cl-IAA), 2-phenylacetic acid (PAA), indole-3-butyric acid (IBA), 2,3-dichlorophenoxyacetic acid (2,4-D), α-naphthalene acetic acid (α-NAA), 2-methoxy-3,6-dichlorobenzoic acid (dicamba), 4-amino-3,5,6-trichloropicolinic acid (torden or picloram), 2,4,5-trichloropicolinic acid (2,4,5-T), or a combination thereof. In another aspect, the cytokinin is zeatin, kinetin, 6-benzylaminopurine, diphenylurea, thidizuron (TDZ), 6-(γ, γ-dimethylallylamino)purine, or a combination thereof. In another aspect, the gibberellin is gibberellin A1 (GA1), gibberellic acid (GA3), ent-gibberellane, ent-kaurene, or a combination thereof. In yet another aspect, the polyamine is putrescine, spermidine, or a combination thereof.

In one aspect, the plant cell or callus is first contacted with a polysaccharide and subsequently contacted with a plant growth regulator. In another aspect, the plant cell or callus is first contacted with a plant growth regulator and subsequently contacted with a polysaccharide. In an alternative aspect, the plant cell or callus is simultaneously contacted with a polysaccharide and a plant growth regulator. In a further aspect, the plant cell or callus is only contacted with a polysaccharide and is not contacted with a plant growth regulator.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of the callus can vary depending on the type of plant. The amount of polysaccharide can vary depending upon, among other things, the selection and number of plant cells. The use of the polysaccharide in the methods described herein permits rapid tissue culturing at room temperature. Due to the ability of the polysaccharide to prevent microbial contamination, the tissue culture can grow for extended periods of time ranging from days to several weeks. Moreover, tissue culturing with the polysaccharide can occur in the dark and/or light. As discussed above, the plant cells can optionally be contacted with any of the biological devices described above. Thus, the use of the polysaccharides and biological devices described herein is a versatile way to culture and grow plant cells—and, ultimately, plants of interest—with enhanced physiological properties.

In other aspects, the plant cells can be cultured in a liquid medium on a larger scale in a bioreactor. For example, plant cells can be cultured in agar and medium, then subsequently contacted with (e.g., injected) a biological device described herein. After a sufficient culturing time (e.g., two to four weeks), the plant cells are introduced into a container with the same medium used above and, additionally, the polysaccharide. In certain aspects, the polysaccharide can be introduced with anionic polysaccharides including, but not limited to, alginates (e.g., sodium alginate, calcium alginate, potassium alginate, etc.). After the introduction of the polysaccharide, if using, the solution is mixed for a sufficient time to produce a desired result (e.g., production of a desired metabolite).

In one aspect, provided herein is a plant grown by the process that involves contacting plant gamete cells or a plant reproductive organ with the biological devices disclosed herein. In a further aspect, the plant is produced by the following method:
  a) contacting a plant callus with the biological device;
  b) culturing the plant callus; and
  c) growing the plant from the plant callus.

In a further aspect, the same method can be applied to other plant parts including fruits, stems, roots, tubers, corms, bulbs, flowers, buds, seeds, and the like. In a still further aspect, the same method can be applied to an entire plant.

In one aspect, the plant callus is immersed in a solution of polysaccharide (e.g., chitosan), then inoculated with the device. In another aspect, the plant callus can be from 2 days up to 20 days old prior to inoculation with the biological devices described herein. The plant callus is then allowed to grow until it is of sufficient weight and size. In one aspect, the plant callus is allowed to grow (i.e., culture) for 1 to 10 weeks after inoculation. The next step involves removal of a polyactive carbohydrate from the callus.

In a further aspect, provided herein is a plant coated with the polyactive carbohydrate disclosed herein. In one aspect, coating a plant with the polyactive carbohydrate increases resistance of the plant to fungal or microbial disease. Further in this aspect, the polyactive carbohydrate is cost-effective and biodegradable, as distinguished from chemical fertilizers and/or pesticides. Still further in this aspect, the polyactive carbohydrate elicits innate defense responses in the plant with respect to insects, pathogens, parasites of the roots, and soil-borne diseases. In another aspect, this innate defense response, while attacking pests and pathogens, does not harm beneficial organisms. In another aspect, provided herein is an agricultural product coated with the polyactive carbohydrate. In a further aspect, the agricultural product can be fruits, leaves, seeds, flowers, grains, nuts, stems, vegetables, and/or mushrooms, and the like. In another aspect, applying the polyactive carbohydrate to an agricultural product can increase yield, reduce decay of fruits and vegetables, improve seed quality, and/or extend the life of cut flowers and/or Christmas trees.

In another aspect, applying the polyactive carbohydrate can reduce environmental stresses on plants such as those caused by drought, soil deficiencies, freezing conditions, and the like. In yet another aspect, the polyactive carbohydrate can be considered environmentally friendly, safe for broad-spectrum use, and non-toxic.

In still another aspect, provided herein is a method for producing a polyactive carbohydrate, the method comprising fermenting any one of the biological devices disclosed herein.

X. Use of the Polyactive Carbohydrate in Hydraulic Fracturing Applications

Guar, also known as guar gum, is a polysaccharide traditionally derived from the endosperm of *Cyamopsis tetragonoloba* but that can also be produced by other plant species. The primary polysaccharide in guar is called guaran and is made of a linear backbone of D-mannose monomers connected by β-(1-4) glycosidic bonds. To the mannose backbone are attached D-galactose monomers via α-(1→6) glycosidic bonds. In some aspects, the galactose residues are thought to follow a regular or repeating pattern of attachment to the mannose backbone. In other aspects, the galactose residues are believed to be randomly distributed, usually in groups of two or three. The ratio of mannose to galactose can be from about 1.6:1 to 2:1, or can be about 1.8:1.

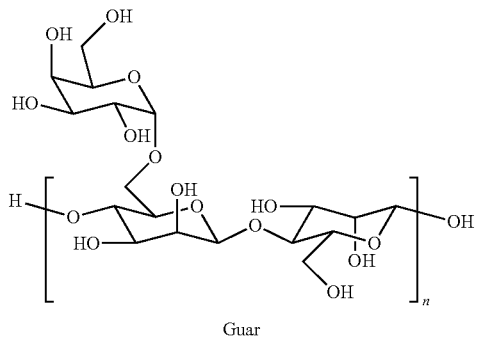

Guar

Guar is a naturally-occurring, high molecular weight, water-soluble polymer. In some aspects, the average molecular weight of guaran polymers is from about 220,000 to about 2,000,000 Da. In another aspect, the average molecular weight is from about 1,000,000 to about 2,000,000 Da. In one aspect, the molecular weight of guar is determined by size exclusion chromatography or a light scattering technique.

In some aspects, guar may be chemically modified after production and/or isolation. In one aspect, chemical modification includes reaction with propylene oxide to form hydroxypropyl guar. In one aspect, a single propylene oxide unit attaches to a galactose residue. In another aspect, multiple propylene oxide units attach to the same galactose residue, forming a chain. In another aspect, two or more propylene oxide units attach to two or more different hydroxyl groups on the same galactose residue. In a further aspect, the hydroxypropyl groups can themselves be modified to produce, for example, carboxymethylhydroxypropyl guar. Other substituents and chemical modifications, including the production of cationic guars, are also contemplated. One having ordinary skill in the art will be able to determine the correct stoichiometries of reactants to use in order to achieve a desired degree of substitution when chemically modifying guar. In other aspects, enzyme preparations can be used to modify the microbial guar disclosed herein, after it is produced.

In one aspect, the polyactive carbohydrates and extracts disclosed herein can be used alone or in combination with guar in applications in the petroleum industry.

In certain aspects, the polyactive carbohydrate either alone or with guar can be dissolved in an aqueous electrolyte solution. In one aspect, dissolving unmodified guar in such a solution will cause the guar to develop viscosity different than that of water. In a further aspect, the development of viscosity occurs concurrently with, or as a result of, hydration. The electrolyte solution can be, for example, aqueous potassium chloride, sodium chloride, or calcium chloride. In one aspect, the electrolyte solution is a 2% solution of potassium chloride in water at pH 7-8. The pH of the electrolyte solution may be adjusted using any of a variety of acids, bases, or buffer systems known in the art.

In other aspects, the presence of metal ions, crosslinking, temperature, solution pH, and polymer concentration can also affect the viscosity of solutions containing guar. In one aspect, crosslinking reactions can be performed to link the side chains of chemically-modified guar to one another.

In one aspect, the polyactive carbohydrate disclosed herein can be used in the petroleum industry. In a further aspect, the polyactive carbohydrate can be included as a component of a hydraulic fracturing fluid, as a component of a drilling fluid, or to alter the viscosity of a crude petroleum product. In another aspect, the polyactive carbohydrate disclosed herein can be used in any application in which plant-based guar is normally used such as, for example, thickening textile and carpet dyes, facilitating paper processing, waterproofing and/or gelling in explosive compositions, binding pharmaceutical tablets, thickening cosmetics and toiletry preparations, controlling the viscosity of fire retardants, drug delivery, flocculating and/or flotation in metallurgy and/or mining applications, or as an additive in the food industry. In a further aspect, the polyactive carbohydrate disclosed herein can be used as a thickener, stabilizer, binder, or texturizing agent in food products such as baked goods, dairy products, meat, condiments, canned goods, ice cream, hot cereals, and the like.

In some aspects, compositions including the polyactive carbohydrate or combinations of the polyactive carbohydrate and plant-based guar can include other ingredients such as, for example, electrolyte solutions, fillers, particulates, surfactants, and the like. In certain aspects, compositions including the polyactive carbohydrate can be used as fluids for hydraulic fracturing. In some aspects, polyactive carbohydrate compositions for hydraulic fracturing can further include petroleum oil.

In one aspect, surfactants can act in concert with the polyactive carbohydrate to alter the viscosity and friction properties of petroleum samples and compositions. The surfactant can be of any type including, for example, a cationic surfactant, an anionic surfactant, a nonionic surfactant, an amphiphilic surfactant, a zwitterionic surfactant, or a combination thereof. In one aspect, the surfactant is a nonionic surfactant such as, for example, ethoxylated alcohols, polysorbate 20, or polysorbate 80. In another aspect, the surfactant is a zwitterionic surfactant such as, for example, soy lecithin. In another aspect, the fillers and particulates can be used as proppants during hydraulic fracturing. As used herein, "proppant" refers to any material that can keep a hydraulic fracture open. Proppants may exert their effects either during or after hydraulic fracturing. Proppants include materials such as sand, ceramic particles, glass, bauxite, and combinations thereof.

In certain aspects, the polyactive carbohydrate described and disclosed herein can be used to alter the viscosity of petroleum oil. In one aspect, the polyactive carbohydrate can be directly mixed with petroleum oil. In another aspect, the polyactive carbohydrate can first be diluted with a solution of an electrolyte, then mixed with petroleum oil. In another aspect, the polyactive carbohydrate can be mixed with guar derived from plant-based sources prior to being placed into contact with petroleum oil. In a further aspect, the polyactive carbohydrate compositions described herein can additionally include a surfactant.

In one aspect, contacting petroleum oil with the polyactive carbohydrate compositions disclosed herein can alter the API gravity of the petroleum oil. "API gravity" as used herein refers to a set of standards developed by the American Petroleum Institute to classify the density of petroleum liquids compared to water. API gravity corresponds to grades of oil; light crude oil typically has API gravity of 31.1° API, medium crude oil between 22.3 and 31.1° API, and heavy crude oil below 22.3° API. API gravity can be derived from density which can be measured by methods such as, for example, ASTM D1298 or ASTM D4052. In another aspect, API gravity can be determined using a fluorescent optical sensor.

In a further aspect, the altered API gravity can be increased; that is, the viscosity of the petroleum oil is reduced through contact with the polyactive carbohydrate compositions. In certain aspects, alteration of the viscosity of the petroleum oil facilitates downstream processing of the petroleum oil.

XI. Additional Applications of the Polyactive Carbohydrate

In one aspect, the biological devices and their products are useful in the paper industry for providing a replacement for some of the cellulosic material in paper and/or in the textile industry as sources of fibers. In another aspect, the biological devices and their products are useful in agriculture, plant biotechnology, and food, including as fertilizers, pesticides, growth factors, root enhancers, seed germination stimulants, and food ingredients. In still another aspect, the biological devices and their products are useful in household and commercial cleaning applications, such as the degreasing of cooking utensils, sinks, etc. In other aspects, the biological devices and their products are useful as surfactants. In still another aspect, the polyactive carbohydrate can be used as a fining agent in winemaking.

In one aspect, the biological devices can be used directly in a given application. In another aspect, the biological devices secrete the polyactive carbohydrates into a culture medium, or the host cells can be lysed to release these gene products. In this aspect, the crude culture medium can be used in the applications provided, or the culture medium can be purified to yield appreciable amounts of polyactive carbohydrate.

In another aspect, the polyactive carbohydrate can be incorporated into a flexible film that can replace plastic in food packaging applications and the like. Further in this aspect, the polyactive carbohydrate can be enzymatically broken down (e.g., by bacteria in the environment) or actively recycled.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such processes and conditions.

Example 1: Preparation of DNA Construct for Production of Polyactive Carbohydrates The DNA construct was composed of the genetic components described herein and assembled in plasmid vectors (e.g., pYES2, pBSK, pETDuet-1). Sequences of genes and/or proteins with desired properties were identified in GenBank; these included a gene that expresses lipase, a gene that expresses chitin synthase, a gene that expresses chitosanase, and a gene that expresses chitin deacetylase. These sequences were synthesized by CloneTex Systems, Inc. (Austin, Tex.). Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors. Lipase was included in some constructs and was functional at any position in the construct. However, a position 5' of the gene for expressing chitin synthase was preferable when the lipase gene was included.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzymes' supplier (Promega). The complete insert, containing restriction sites on each end, was then ligated into the plasmid. Successful construction of the insert and ligation of the insert into the plasmid were confirmed by gel electrophoresis.

From 5' to 3', one version of the construct includes (a) a gene that expresses chitin synthase, (b) a CYC1 terminator, (c) a GAL1 promoter, (d) a gene that expresses chitosanase, (e) a CYC1 terminator, (f) a GAL1 promoter, (g) a gene that expresses chitin deacetylase, (h) a CYC1 terminator, (i) a GAL1 promoter, and (j) a yellow fluorescent reporter protein (FIGS. 1A and 1B).

From 5' to 3', a second version of the construct includes (a) a gene that expresses lipase, (b) a CYC1 terminator, (c) a GAL1 promoter, (d) a gene that expresses chitin synthase, (e) a CYC1 terminator, (f) a GAL1 promoter, (g) a gene that expresses chitosanase, (h) a CYC1 terminator, (i) a GAL1 promoter, (j) a gene that expresses chitin deacetylase, (k) a CYC1 terminator, (l) a GAL1 promoter, and (m) a yellow fluorescent reporter protein (FIGS. 2A and 2B).

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual*, 2nd ed., Vol. 1, Cold Spring Harbor Laboratory Press: Cold Spring Harbor, N.Y.). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm and 280 nm. In order to verify final ligations, DNA was visualized and purified via electrophoresis using a Thermo EC-150 power supply.

The DNA construct was made with gene parts fundamental for expression of sequences such as, for example, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the method described below.

A DNA device for the production of polyactive carbohydrates was constructed by assembling a plasmid (e.g., pYES2) having the following genetic components in the following order: (a) a gene that expresses chitin synthase having SEQ ID NO. 1, (b) a CYC1 terminator, (c) a GAL1 promoter, (d) a gene that expresses chitosanase having SEQ ID NO. 2, (e) a CYC1 terminator, (f) a GAL1 promoter, (g) a gene that expresses chitin deacetylase having SEQ ID NO. 3, (h) a CYC1 terminator, (i) a GAL1 promoter, and (j) a yellow fluorescent reporter protein having SEQ ID NO. 4. The DNA construct having SEQ ID NO. 5 was transformed into cells, as described below, to produce the biological devices. Plasmids containing the DNA construct are shown in FIGS. 1A, 1B, 2A, 2B, 5A, and 5B.

Example 2: Selection of Microorganisms

The polyactive carbohydrate was produced using transfected yeasts (*Saccharomyces cerevisiae*, ATCC® 200892™).

Alternatively, bacterial devices were constructed with one of the following strains of cells: *Escherichia coli*, ONE-SHOT® Top10 competent cells from Life Technologies™, BL21 (DE3) *E. coli* from Novagen, Inc., or DH5α™ *E. coli* from Thermo Fisher Scientific.

Example 3: Development of Competent Yeast Cells

Yeast cells were made competent by subjecting them to an electrochemical process adapted from Gietz and Schiestl (*Nature Protocols*, 2007, 2:35-37). Briefly, a single yeast colony was inoculated into 100 mL YPD (yeast extract peptone dextrose) growth media. Yeast was grown overnight on a shaker at 30° C. to $OD_{600}$=1.0. (Acceptable results were obtained with $OD_{600}$ values ranging from 0.6 to 1.8.) Cells were centrifuged at 2000 rpm in a tabletop centrifuge and resuspended in 10 mL TEL buffer (10 mM Tris-HCl, 1 mM EDTA, 0.1 M LiAc, pH=7.5) and shaken vigorously overnight at room temperature. Cells were again centrifuged and resuspended in 1 mL TEL buffer. Cells prepared in this manner could be stored in the refrigerator for up to one month.

Example 4: Transformation of Microbial Cells to Produce Polyactive Carbohydrate Device Competent cells were stored in the freezer until needed. Cells were thawed on ice and 100 µL of competent cells in TEL buffer were placed in a sterile 1.5 mL microcentrifuge tube. To this was added 5 µL of a 10 mg/mL solution of salmon sperm DNA (carrier DNA). Transforming DNA was added in various amounts. From 1 to 5 µg was sufficient for plasmids from commercial sources, but more DNA was required when transforming yeast with artificial DNA constructs. 10 µL of the DNA device were added to the microcentrifuge tube containing the competent yeast cells and the contents of the tube were mixed. The DNA-yeast suspension was incubated for 30 min at room temperature.

A PLATE solution (consisting of 40% PEG-3350 in 1×TEL buffer) was prepared. 0.7 mL of PLATE solution was added to the DNA-yeast suspension and the contents were mixed thoroughly and incubated for 1 h at room temperature. The mixture was placed in an electromagnetic chamber for 30 minutes. Cells were then heated at 42° C. for 5-10 minutes and 250 µL aliquots were plated on yeast malt agar to which selective growth compounds had been added. Plates were incubated overnight at 30° C.

DNA expression and effectiveness of transformation were determined by fluorescence of the transformed cells expressed in fluorescence units (FSUs) using a 20/20 Luminometer (Promega) according to a protocol provided by the manufacturer. Plasmid DNA extraction, purification, PCR, and gel electrophoresis were also used to confirm transformation. Different transformed devices were obtained. Different types of fluorescent reporter proteins were used (e.g., yellow, red, green, and cyan) for all transformed cells and/or constructs. However, the yellow fluorescent protein was preferred. When no fluorescent reporter protein was assembled, no fluorescence was observed.

*S. cerevisiae* cells were subjected to transformation with the modified pYES2 plasmid as described above. Transformed yeast cells were incubated for 30 min at 28-30° C. Colonies of transformed yeast cells were selected, their DNA isolated and subjected to PCR amplification. Two control treatments were also carried out: (1) a negative control involving competent yeast and nuclease free water instead of a plasmid and (2) a positive control involving competent yeast with unmodified pYES2 plasmid.

Alternatively, the pETDuet-1 plasmid-based device was transformed into DH5a and BL21(DE3) *E. coli* using a standard heat shock protocol. Four clones were selected from a transformed plate and processed for full-length DNA sequencing. A clone with 100% DNA sequence accuracy was selected for further processing and was used to obtain a high concentration of plasmid construct at a mid-scale plasmid purification level.

The following non-limiting procedures were used to produce polyactive carbohydrates:

Method 1
1. Yeasts transformed with the device depicted in FIGS. 1A and 1B were fermented at 30° C. for 72 hours. Alternatively, the yeasts were transformed with the device depicted in FIGS. 2A and 2B. If used, bacteria were transformed with the device depicted in FIGS. 5A and 5B.
2. At 48 hours of fermentation, lyticase (240 uL/L) was added.
3. The culture was sterilized by autoclaving at 121° C. for 30 minutes.
4. The mixture was filtered with an 8 μm filter to produce a supernatant composed of the polyactive carbohydrate.

Method 2
1. Yeast transformed with the device depicted in FIGS. 1A and 1B were fermented at 30° C. for 72 hours.
2. The mixture was centrifuged at 9,000 rpm for 15 minutes to produce a pellet.
3. The pellet was resuspended in water (1 g/100 mL)
4. Lyticase (240 uL/L) was added to the solution.
5. The solution was sonicated two times for 30 minutes.
6. The solution was centrifuged at 9,000 rpm for 15 minutes.
7. The mixture was filtered with a 0.45 μm filter to produce a supernatant composed of the polyactive carbohydrate.

Example 5: Evaluation of Antimicrobial Activity of Polyactive Carbohydrates

The polyactive carbohydrates produced in Methods 1 and 2 above (device depicted in FIGS. 1A and 1B) were mixed at concentrations of 5% and 10% in PDA culture mediums with *Fusarium* sp. The antimicrobial tests were carried out at a temperature of 26° C. for 5 days with continuous observations daily. After 5 days, little to no growth of *Fusarium* sp. was observed compared to a control culture of *Fusarium* sp. with no polyactive carbohydrate.

Due to the success of initial testing, further antifungal evaluation was performed. *Fusarium graminearum*. (ATCC 15624) at a concentration of $10^4$ cells/mL (minimum) was used. This fungal culture was mixed with an extract produced above (10% of either extract based on total volume) and incubated at 26° C. for up to 72 hours.

Samples were removed at 0, 30, and 60 minutes, as well as 24, 48, and 72 hours to determine fungal growth. 500 μL aliquots were placed into PDA agar plates to confirm whether fungal cells were dead or alive (i.e., able to form colonies). After approximately 30 minutes of incubation, antifungal effects of the extracts was observed.

*Fusarium graminearum* growth was inhibited by the extract produced by the biological device as well as from unpurified cultures of the biological devices after 30 minutes of treatment. Untreated fungal colonies of *Fusarium graminearum* after 24 hours exhibited strong growth versus a fungal culture treated with the extract, which exhibited no fungal growth after only 30 minutes of treatment.

Example 6: Humidity Testing

Two (2) ml of polyactive carbohydrate produced in Method 2 (device depicted in FIGS. 1A and 1B transformed in yeast) was sprayed directly onto the surface of rabbit skin. The percentage of moisture and oil on the samples were determined using a digital moisture monitor for skin. The results are provided in Table 5 below with control experiments.

TABLE 5

Humidity Testing Results

| | Humidity | Oil |
|---|---|---|
| Water | 16.4% | 24.5% |
| Polyactive Carbohydrate | 33.3% | 32.0% |
| Chitosan | 35.6% | 22.4% |
| Polyactive Carbohydrate + Chitosan | 43.6% | 25.5% |

Example 7: Production of Soft Biofoams

Polyactive Carbohydrate Extract

The following procedure was used to produce the polyactive carbohydrate extract:

1. Fermentation of yeast transformed with the construct in FIGS. 1A and 1B in yeast malt medium with 2% of raffinose, 1 mg/mL of glucosamine and induction with galactose at 30° C. for 72 hours.
2. Centrifugation at 9000 rpm for 15 minutes and pelletizing of the culture.
3. Pellet resuspension (1 g/50 mL) in sterile deionized water.
4. Sonication: 3 times for 2.5 minutes.
6. Centrifugation at 9000 rpm for 15 minutes.
7. Filtration of supernatant with 0.45 μm filter.

Preparation of Soft Biofoam

The polyactive carbohydrate extract (38 mL; optical density 2.5) was mixed with surfactant TWEEN 80 (2 ml) for 3 minutes. Castor oil (50 mL) was next added and mixed for 10 minutes.

Separately, the polyactive carbohydrate extract (10 mL) and bentonite (0.5 g) were vortexed for 5 minutes. This mixture was added to the solution above and mixed for 10 minutes. The above process was carried out at room temperature (25°-28° C.) to produce the biopolyol.

Isocyanate (Geos Quimica S.A.S—Isocyanate for rigid-MDI) (20 mL) was added to the biopolyol above at a ratio of 5:1 (biopolyol: isocyanate) for 7 minutes at room temperature (25°-28° C.). Pressured air (5-15 psi) was injected during the last two (2) minutes of this process; however, in some cases there is no need to inject air. The resultant product was allowed to dry overnight at room temperature. The mixture was transferred to a mold to produce a shaped article (e.g., a cube). The biofoam was taken out of the mold and transferred to an oven to complete drying (30°-40° C.) for 30-60 minutes.

Example 8: Fracking by Polyactive Carbohydrate

Experiments modeling the retention of petroleum in sand as a model for fracking were carried out using extracts produced by the device depicted in FIGS. 1A and 1B transformed in yeast. Extracts from cultures of the biological devices used for these experiments had an optical density (OD) of 2.3. Treatment groups and conditions are summarized in Table 6; these were prepared in separate glass containers:

TABLE 6

Treatment Groups and Conditions for Retention of Petroleum from Sand

| | Treatment | |
|---|---|---|
| | A | B |
| Volume of Petroleum (mL) | 80 | 25 |
| Mass of Sand (g) | 80 | 50 |
| Volume of Biological Device Extract (mL) | 15 | 30 |

These treatment groups were prepared and added to flasks, which were then heated for 20 minutes at 60° C. Petroleum retention in sand was observed. The scale in Table 7 was used to qualitatively assess the degree of petroleum retention:

TABLE 7

Measurement Scale for Petroleum Retention in Sand

| Degree of Petroleum Retention | Measure |
|---|---|
| Too low | 1 |
| Low | 2 |
| Medium | 3 |
| High | 4 |
| Too high | 5 |

Further observations of petroleum retention were recorded at 40 minutes and at 1 hour. Photographs of the samples at the time of initial mixing and at 20 minutes, 40 minutes, and one hour can be seen in FIGS. 3A-D, with treatment "A" on the left and treatment "B" on the right. Evaluations of the samples at each time point using the scale in Table 7 are presented in Table 8:

TABLE 8

Assessment of Petroleum Retention in Sand

| Time | Treatment A | Treatment B |
|---|---|---|
| 0 min. (initial mixing) | N/A | N/A |
| After 20 min. heating | 2 | 1-2 |
| After 40 min. heating | 3-4 | 3 |
| After 1 hr. heating | 3-4 | 3 |

After 40 minutes, the petroleum sample with polyactive carbohydrate dispersed throughout the sand; this did not significantly change after one hour.

Example 9: Degreasing Experiments

Figure 4A:
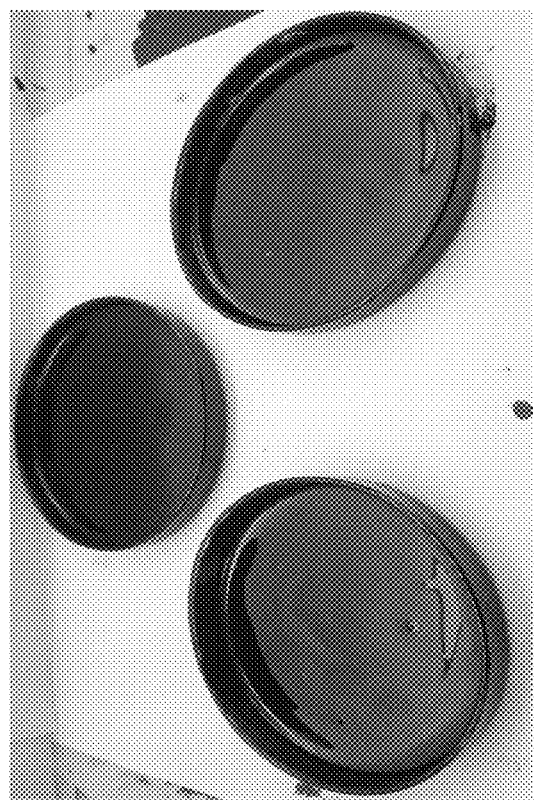
FIGS. 4A-C show degreasing of surfaces by extracts from the biological devices described herein over time.
Figure 4B:
Figure 4C:
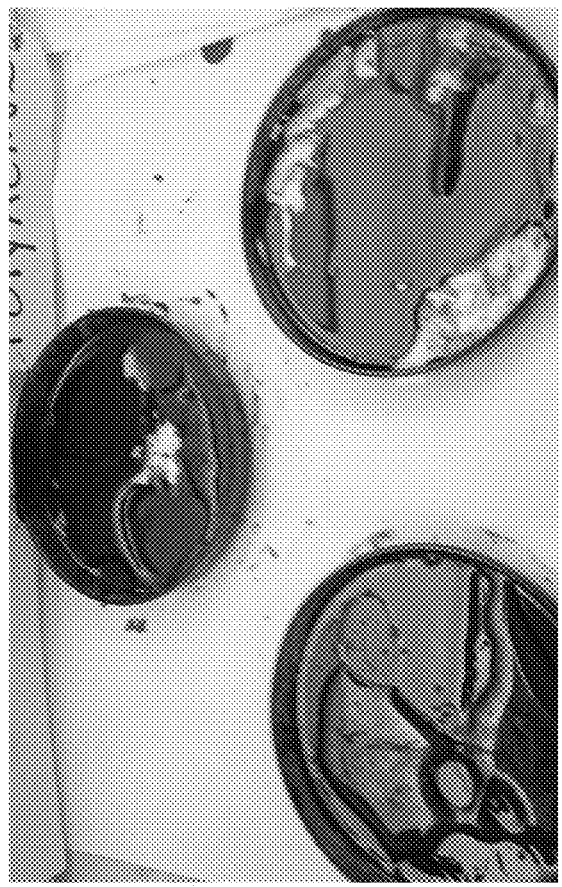

In a second experiment, degreasing and/or decontamination of a surface with extracts was performed. 80 mL of petroleum were mixed with 20 mL of extract produced by the device depicted in FIGS. 1A and 1B transformed in yeast. 8-15 mL of this mixture were distributed into Petri dishes and observed over time. At 10 minutes, some degreasing of surfaces becomes evident. After 24 hours, qualitatively, further degreasing can be seen. FIGS. 4A-4C show the Petri dishes at times of 0 min, 10 min, and 24 hours. Thus, the polyactive carbohydrates described herein can effectively degrease surfaces without stirring or the application of heat.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A method for producing a polyactive carbohydrate, the method comprising fermenting a biological device comprising host cells transformed with a DNA construct comprising the following genetic components: (a) a gene that expresses chitin synthase; (b) a gene that expresses chitosanase; (c) a gene that expresses chitin deacetylase; and (d) optionally, a gene that expresses lipase, wherein the gene that expresses chitin deacetylase has a sequence of SEQ ID NO. 3 or at least 70% homology thereof.

2. The composition of claim 1, wherein the gene that expresses chitin synthase has a sequence of SEQ ID NO. 1 or at least 70% homology thereof.

3. The composition of claim 1, wherein the gene that expresses chitosanase has a sequence of SEQ ID NO. 2 or at least 70% homology thereof.

4. The composition of claim 1, wherein the gene that expresses lipase has a sequence of SEQ ID NO. 6 or at least 70% homology thereof.

5. The method of claim 1, wherein the construct further comprises one or more ribosomal binding sites preceding the gene that expresses lipase, the gene that expresses chitin synthase, the gene that expresses chitosanase, and the gene that expresses chitin deacetylase, or any combination thereof.

6. The method of claim 1, wherein the construct comprises from 5' to 3' the following genetic components in the following order: (1) the gene that expresses chitin synthase, (2) the gene that expresses chitosanase, and (3) the gene that expresses chitin deacetylase.

7. The method of claim 1, wherein the construct comprises from 5' to 3' the following genetic components in the following order: (1) the gene that expresses chitin synthase having a sequence of SEQ ID NO. 1 or at least 70% homology thereof, (2) the gene that expresses chitosanase having a sequence of SEQ ID NO. 2 or at least 70% homology thereof, and (3) the gene that expresses chitin deacetylase having a sequence of SEQ ID NO. 3 or at least 70% homology thereof.

8. The method of claim 1, wherein the construct comprises from 5' to 3' the following genetic components in the following order: (1) the gene that expresses lipase, (2) the gene that expresses chitin synthase, (3) the gene that expresses chitosanase, and (4) the gene that expresses chitin deacetylase.

9. The method of claim 1, wherein the construct comprises from 5' to 3' the following genetic components in the following order: (1) the gene that expresses lipase having a sequence of SEQ ID NO. 6 or at least 70% homology thereof, (2) the gene that expresses chitin synthase having a sequence of SEQ ID NO. 1 or at least 70% homology thereof, (3) the gene that expresses chitosanase having a sequence of SEQ ID NO. 2 or at least 70% homology thereof, and (4) the gene that expresses chitin deacetylase having a sequence of SEQ ID NO. 3 or at least 70% homology thereof.

10. The method of claim 1, wherein the construct comprises from 5' to 3' the following genetic components in the following order: (1) the gene that expresses lipase, (2) the gene that expresses chitosanase, (3) the gene that expresses chitin synthase, and (4) the gene that expresses chitin deacetylase.

11. The method of claim 1, wherein the construct comprises from 5' to 3' the following genetic components in the following order: (1) the gene that expresses lipase having a sequence of SEQ ID NO. 6 or at least 70% homology thereof, (2) the gene that expresses chitosanase having a sequence of SEQ ID NO. 2 or at least 70% homology thereof, (3) the gene that expresses chitin synthase having a sequence of SEQ ID NO. 1 or at least 70% homology thereof, and (4) the gene that expresses chitin deacetylase having a sequence of SEQ ID NO. 3 or at least 70% homology thereof.

12. The method of claim 1, wherein the host cells are transformed with a vector comprising the DNA construct.

13. The method of claim 12, wherein the vector is a plasmid.

14. The method of claim 12, wherein the vector is pWLNEO, pSV2CAT, pOG44, pXTI, pSG (Stratagene), pSVK3, pBSK, pBR322, pYES, pYES2, pBSKII, pUC, pUC19, or pETDuet-1.

15. The method of claim 1, wherein the host cells comprise yeast or bacteria.

16. The composition of claim 1, wherein the gene that expresses chitin synthase has a sequence of SEQ ID NO. 1 or at least 70% homology thereof and the gene that expresses chitosanase has a sequence of SEQ ID NO. 2 or at least 70% homology thereof.

17. The composition of claim 1, wherein the gene that expresses chitin synthase has a sequence of SEQ ID NO. 1 or at least 70% homology thereof, the gene that expresses chitosanase has a sequence of SEQ ID NO. 2 or at least 70% homology thereof, and the gene that expresses lipase has a sequence of SEQ ID NO. 6 or at least 70% homology thereof.

* * * * *

SEQUENCE LISTING

```
<160> NUMBER OF SEQ ID NOS: 8

<210> SEQ ID NO 1
<211> LENGTH: 3414
<212> TYPE: DNA
<213> ORGANISM: Saccharomyces cerevisiae

<400> SEQUENCE: 1
aagcttgcca ccatgagtga tcaaaataat cgatcgagaa atgaatatca ctcaaaccgg      60
aagaatgaac cttcctatga actccaaaat gcacatagcg ggctatttca ctcttctaat     120
gaagaattaa caaacaggaa ccaaagatat accaatcaaa atgccagcat gggttcattc     180
actccagtcc aatctttgca atttccagaa caatctcagc aaacaaatat gctttataac     240
ggtgacgatg gcaataataa tactatcaat gataacgaac gagacatata tggaggtttt     300
gtcaaccacc atcgccagcg tcccccacca gcaactgcag aatacaatga cgtttttaat     360
acgaatagtc aacagctacc gtcggaacat caatacaata acgtaccttc atatccactt     420
ccttcgataa atgtgattca aaccactcca gaactcatac ataacggctc acagactatg     480
gccaccccca tcgaaaggcc cttctttaac gaaaacgact actattataa taacaggaac     540
```

-continued

```
tctaggacgt caccgagtat tgcttctagt agcgatggtt atgcagatca ggaagctagg    600
cccatttttgg agcaacccaa caataacatg aatagcggta atattcctca ataccatgac    660
caacctttttg gatacaacaa tggttaccat ggcctacagg caaaagatta ctatgacgat    720
ccggagggtg gttatattga tcagagagga gatgactatc agattaattc atatttgggt    780
agaaacggtg aaatggttga tccttacgat tatgaaaaca gtttaagaca tatgactcct    840
atggagcgta gagaatatct tcatgatgat agcagacccg taaacgatgg aaaagaagaa    900
ttagacagtg tgaaaagcgg ttactctcat agagacttgg gggaatatga caaggatgat    960
tttttcaaggg atgacgagta cgatgatctc aacactattg ataaattaca gtttcaagct   1020
aatggtgtac ctgcatcatc ctcggtgtct tctatcggat ctaaagaatc cgacataata   1080
gtaagcaatg ataacttaac cgcaaataga gcactaaaga gaagcggtac tgaaattagg   1140
aaattcaaac tttggaatgg taattttgtt ttcgattctc aatcagtaa gacgctattg    1200
gaccaatacg ctactacaac agaaaatgca aacactttac caaatgagtt taagtttatg   1260
agatatcaag cagttacttg cgaacctaat caacttgcag agaagaattt cacggtgagg   1320
cagttgaagt atttaactcc aagggaaacg gaattgatgc tagtagtcac aatgtataat   1380
gaagaccata tcctgttagg aagaactttg aaaggtatta tggacaatgt caaatatatg   1440
gtgaaaaaaa aaaattcaag cacttggggg ccggatgcat ggaaaaagat tgtcgtttgt   1500
atcatttcag atggtagatc caaaattaat gaacgctcgc tagcattact aagttcgtta   1560
ggttgttacc aggacgggtt tgctaaggat gaaattaatg aaaaaaaagt ggcaatgcat   1620
gtctacgaac atacgacaat gatcaacatc acaaatattt cggaatcaga ggtttcatta   1680
gaatgcaatc aaggtactgt tccaatacaa ctttttgttt gtttgaaaga gcaaaatcag   1740
aaaaaaatta actcacatag atgggcattt gaaggctttg cagaattact gcgtcccaat   1800
atcgttacat tgttagatgc tggtactatg ccaggtaaag attctattta ccagttatgg   1860
agagagttca ggaatccaaa tgttggtggc gcatgtggtg aaataagaac tgatttgggt   1920
aagagatttg taaagttgtt gaatccttta gttgcatcac agaatttcga atacaaaatg   1980
tccaatattt tagacaaaac aaccgagtct aactttggat ttattactgt tctaccgggg   2040
gcattctctg cgtataggtt tgaagctgtg agaggccaac cattacagaa gtacttttat   2100
ggtgaaatta tggaaaatga aggttttcat ttttttttctt ccaatatgta tcttgctgaa   2160
gatcgtattt tatgctttga agtggtcaca aaaaaaaatt gtaattggat tttgaaatac   2220
tgcagaagtt cttatgcttc aacagatgta ccggagaggg tccctgaatt tattcttcag   2280
aggaggcgtt ggttgaatgg ttcatttttt gctagtgtat attccttttg tcattttac    2340
agagtctgga gcagtggtca taatattggt agaaaactcc ttttgacggt tgaatttttt   2400
tacctttttct tcaatacatt gatttcatgg ttttcattga gttcatttttt cctagtcttt   2460
aggattctca ctgtttctat tgcactggca taccattcag catttaatgt gttgtccgtc   2520
atattcctgt ggctttatgg gatttgtacc ttatcaacat tcatactgtc attgggtaat   2580
aaacctaaaa gtactgagaa attttatgtt ctaacttgcg tcattttttgc ggtgatgatg   2640
atttacatga tattctgcag tatattcatg agtgtcaaat ccttccaaaa tatattgaaa   2700
aacgatacca tcagctttga gggtttgatt accacagagg ctttcaggga tattgttatc   2760
tctctgggct ccacttattg tttgtaccta atcagttcaa ttatctattt gcagccatgg   2820
catatgttga caagttttat tcagtatatt ttattgagtc cttcttacat caatgttttg   2880
```

```
aatatctatg cattttgtaa tgtccacgac ttatcatggg gtacaaaggg tgcaatggca    2940
aatccgctgg gtaagattaa tactacagaa gatggtacgt tcaaaatgga agttctggtc    3000
tctagttcag agattcaagc aaactacgat aaatatttga aagttttaaa tgacttcgat    3060
ccaaaatcag aatctcggcc tactgagcca tcttatgatg aaaaaaagac tggctattat    3120
gcaaacgtta gatctctcgt gattatcttt tgggtcatca caaatttcat catcgttgct    3180
gttgtcttag aaaccggtgg gattgcagat tatattgcta tgaaatccat atcaactgat    3240
gacactttag aaactgcaaa gaaggcggaa attcccttaa tgaccagtaa ggcctcaatt    3300
tattttaatg taattttatg gttagttgca ttatcggcat taataaggtt cattggttgc    3360
tcaatataca tgatagtaag gttttttaaa aaggttacat ttcgctaagg tacc          3414
```

<210> SEQ ID NO 2
<211> LENGTH: 1712
<212> TYPE: DNA
<213> ORGANISM: Saccharomyces cerevisiae

<400> SEQUENCE: 2

```
gaattcaagc ttatgtcact cctttacatc attcttctat tcacacaatt cttactactg      60
ccaaccgatg cctttgatag gtctgctaac acaaatattg ctgtttattg gggtcaaaac     120
tcagcaggaa cgcaagaatc cttagctact tactgtgaat cttctgatgc tgatattttc     180
ctattatctt tcttgaacca atttccaacc cttggtttga actttgccaa cgcatgctct     240 gatactttt ctgatggctt acttcactgc acccagattg ctgaagatat tgaaacttgc     300
cagtccctag gaaagaaagt tctattatca ttaggtggtg catctggtag ctacctcttt     360
tcagatgatt ctcaagcgga aacttttgca caaactttat gggatacttt cggtgaaggt    420
acaggtgcca gtgagagacc atttgactca gcagtcgttg atggttttga ttttgatatt    480
gaaaacaaca acgaagtagg ctatagtgcg ttagctacca agttaagaac tttgtttgcc    540
gaaggtacaa agcaatatta ccttttctgcc gcaccacaat gtccataccc ggatgcttct    600
gttggtgact tgttggaaaa tgcagacatt gattttgcgt tcatccaatt ttacaataat    660
tactgcagtg tgagtggtca attcaattgg gatacttggt taacctatgc tcaaactgta    720
tccccaaata aaaatatcaa actgttctta ggtttacctg gttctgcttc tgctgctggc    780
tctggttata tttctgacac ttcttttattg gaatcaacta ttgcagatat tgcctcttca    840
agttcttttg gtggtattgc gttatgggat gcatctcaag cctttttccaa cgagctaaat    900 ggtgaaccat atgttgagat tttgaagaat ttgctaacaa gtgctagcca gaccgccact    960
actacagttg ccacctcaaa aacctcagca gcctcaactt catctgcttc aacttcatct   1020
gcttcaactt ctcagaaaaa gaccacacaa tctacgacat ctacacaaag taaaagcaaa   1080
gttactttat ctccaactgc aagcagcgct atcaaaacat caattactca aactacaaaa   1140
acattgacga gtagcaccaa gacaaaaatct agtctaggta ccaccacaac agagagcact   1200
ttaaattcag ttgctatcac aagtatgaaa actactctat cttcccaaat aaccagtgct   1260
gccttggtga ccctcaaac aactactact agcatagttt cttcggcccc aattcaaaca   1320
gctatcacta gtactctttc gccagcaacg aagagttctt ctgtcgtttc cctacagaca   1380
gctactacta gtacgctttc cccaacaacg accagtacaa gctcaggtag tacaagctca   1440
ggtagtacaa gctcagacag tacagctcgt acattggcta agaattgaa tgctcaatat   1500 gcggctggta aattgaacgg taatctacc tgtactgaag gtgaaattgc atgctctgct   1560
gatgggaagt tcgccgtttg tgatcatagc gcttgggttt acatggaatg tgcttctgga   1620
```

```
accacatgtt atgcttatga ctccggcgac tcagtctata cccaatgtaa tttctcttat    1680
ttggaaagca attacttta actcgaggat cc                                  1712

<210> SEQ ID NO 3
<211> LENGTH: 939
<212> TYPE: DNA
<213> ORGANISM: Saccharomyces cerevisiae

<400> SEQUENCE: 3
atgagaatac aactaaatac aattgatttg caatgtatta ttgcactttc ctgtctgggg    60
caatttgttc acgcggaagc taatagggaa gatttaaagc agatagactt tcaatttcct   120
gtattggaaa gggcagctac aaaaacgcct tttccggatt ggcttagtgc atttaccggg   180
ttaaaagaat ggcctgggtt agatccacct tatataccctt tagatttcat tgatttcagt   240
caaattccag attataagga atatgatcaa aaccattgcg acagtgttcc aagggactcg   300
tgctctttcg attgccatca ctgcaccgaa acgatgatg tgtacacatg ttccaaactt    360
tcccagacat ttgacgatgg tccttctgct tccactacta aattattgga ccggttgaag   420
cataattcca ccttcttcaa tttaggtgtc aatatagttc aacatccaga tatctatcaa   480
agaatgcaaa aggagggaca cttaatcggc tcacatacct ggtctcacgt atatttgcca   540
aatgtatcga atgaaaaaat tatagctcaa attgaatggt ccatctgggc gatgaatgct   600
actggcaacc atacccccaa atggttcaga cctccatatg gcggaataga aatagagta    660 agagcaataa caaggcaatt tggcttacaa gccgtcttat gggatcacga tacttttgat   720
tggagcctcc ttctcaatga ttctgtcata actgaacaag aaattcttca aaatgtaata   780
aactggaaca gtcaggaac cggattaata ttagaacacg attcaacgga aaaaactgtc   840
gatcttgcca ttaaaataaa taagttgata ggtgatgatc aatcaacagt ttctcattgt   900
gtcggcggaa ttgattacat aaaagaattc ttgtcctaa                         939

<210> SEQ ID NO 4
<211> LENGTH: 890
<212> TYPE: DNA
<213> ORGANISM: Artificial sequence
<220> FEATURE:
<223> OTHER INFORMATION: Synthetic construct

<400> SEQUENCE: 4
ggattcaaag aggagaaata ctagatggtg agcaagggcg aggagctgtt caccggggtg    60
gtgcccatcc tggtcgagct ggacggcgac gtaaacggcc acaagttcag cgtgtccggc   120
gagggcgagg gcgatgccac ctacggcaag ctgaccctga agttcatctg caccaccggc   180
aagctgcccg tgccctggcc caccctcgtg accaccttcg ctacggcct gcaatgcttc    240 gcccgctacc ccgaccacat gaagctgcac gacttcttca gtccgccat gcccgaaggc    300 tacgtccagg agcgcaccat cttcttcaag gacgacggca actacaagac ccgcgccgag   360
gtgaagttcg agggcgacac cctggtgaac cgcatcgagc tgaagggcat cgacttcaag   420
gaggacggca acatcctggg gcacaagctg gagtacaact acaacagcca caacgtctat   480
atcatggccg acaagcagaa gaacggcatc aaggtgaact tcaagatccg ccacaacatc   540
gaggacggca gcgtgcagct cgccgaccac taccagcaga cacccccat cggcgacggc    600 cccgtgctgc tgcccgacaa ccactacctg agctaccagt ccgccctgag caaagacccc   660
aacgagaagc gcgatcacat ggtcctgctg gagttcgtga ccgccgccgg gatcactctc   720
```

| | | |
|---|---|---|
| ggcatggacg agctgtacaa gtaataatac tagagccagg catcaaataa aacgaaaggc | 780 | |
| tcagtcgaaa gactgggcct ttcgttttat ctgttgtttg tcggtgaacg ctctctacta | 840 | |
| gagtcacact ggctcacctt cgggtgggcc tttctgcgtt tataaagctt | 890 | |

<210> SEQ ID NO 5
<211> LENGTH: 14634
<212> TYPE: DNA
<213> ORGANISM: Artificial sequence
<220> FEATURE:
<223> OTHER INFORMATION: Synthetic construct

<400> SEQUENCE: 5

| | |
|---|---|
| acggattaga agccgccgag cgggtgacag ccctccgaag gaagactctc ctccgtgcgt | 60 |
| cctcgtcttc accggtcgcg ttcctgaaac gcagatgtgc ctcgcgccgc actgctccga | 120 |
| acaataaaga ttctacaata ctagctttta tggttatgaa gaggaaaaat tggcagtaac | 180 |
| ctggccccac aaaccttcaa atgaacgaat caaattaaca accataggat gataatgcga | 240 |
| ttagtttttt agccttattt ctgggtaat taatcagcga agcgatgatt tttgatctat | 300 |
| taacagatat ataaatgcaa aaactgcata accactttaa ctaatacttt caacattttc | 360 |
| ggtttgtatt acttcttatt caaatgtaat aaaagtatca acaaaaaatt gttaatatac | 420 |
| ctctatactt taacgtcaag gagaaaaaac cccggatcgg actactagca gctgtaatac | 480 |
| gactcactat agggaatatt aagcttgcca ccatgagtga tcaaaataat cgatcgagaa | 540 |
| atgaatatca ctcaaaccgg aagaatgaac cttcctatga actccaaaat gcacatagcg | 600 |
| ggctatttca ctcttctaat gaagaattaa caaacaggaa ccaagatat accaatcaaa | 660 |
| atgccagcat gggttcattc actccagtcc aatctttgca atttccagaa caatctcagc | 720 |
| aaacaaatat gctttataac ggtgacgatg gcaataataa tactatcaat gataacgaac | 780 |
| gagacatata tggaggtttt gtcaaccacc atcgccagcg tcccccacca gcaactgcag | 840 |
| aatacaatga cgttttaat acgaaatagtc aacagctacc gtcggaacat caatacaata | 900 |
| acgtaccttc atatccactt ccttcgataa atgtgattca aaccactcca gaactcatac | 960 |
| ataacggctc acagactatg gccaccccca tcgaaaggcc cttctttaac gaaaacgact | 1020 |
| actattataa taacaggaac tctaggacgt caccgagtat tgcttctagt agcgatggtt | 1080 |
| atgcagatca ggaagctagg cccatttttgg agcaacccaa caataacatg aatagcggta | 1140 |
| atattcctca ataccatgac caaccttttg gatacaacaa tggttaccat ggcctacagg | 1200 |
| caaaagatta ctatgacgat ccggagggtg gttatattga tcagagagga gatgactatc | 1260 |
| agattaattc atatttgggt agaaacggtg aaatggttga tccttacgat tatgaaaaca | 1320 |
| gtttaagaca tatgactcct atggagcgta gagaatatct tcatgatgat agcagacccg | 1380 |
| taaacgatgg aaaagaagaa ttagacagtg tgaaaagcgg ttactctcat agagacttgg | 1440 |
| gggaatatga caaggatgat ttttcaaggg atgacgagta cgatgatctc aacactattg | 1500 |
| ataaattaca gtttcaagct aatggtgtac ctgcatcatc ctcggtgtct tctatcggat | 1560 |
| ctaaagaatc cgacataata gtaagcaatg ataacttaac cgcaaataga gcactaaaga | 1620 |
| gaagcggtac tgaaattagg aaattcaaac tttggaatgg taattttgtt ttcgattctc | 1680 |
| caatcagtaa gacgctattg gaccaatacg ctactacaac agaaaatgca aacactttac | 1740 |
| caaatgagtt taagtttatg agatatcaag cagttacttg cgaacctaat caacttgcag | 1800 |
| agaagaattt cacggtgagg cagttgaagt atttaactcc aagggaaacg gaattgatgc | 1860 |
| tagtagtcac aatgtataat gaagaccata tcctgttagg aagaactttg aaaggtatta | 1920 |

```
tggacaatgt caaatatatg gtgaaaaaaa aaaattcaag cacttggggg ccggatgcat    1980
ggaaaaagat tgtcgtttgt atcatttcag atggtagatc caaaattaat gaacgctcgc    2040
tagcattact aagttcgtta ggttgttacc aggacgggtt tgctaaggat gaaattaatg    2100
aaaaaaaagt ggcaatgcat gtctacgaac atacgacaat gatcaacatc acaaatattt    2160
cggaatcaga ggtttcatta gaatgcaatc aaggtactgt tccaatacaa cttttgtttt    2220
gtttgaaaga gcaaaatcag aaaaaaatta actcacatag atgggcattt gaaggctttg    2280
cagaattact gcgtcccaat atcgttacat tgttagatgc tggtactatg ccaggtaaag    2340
attctattta ccagttatgg agagagttca ggaatccaaa tgttggtggc gcatgtggtg    2400
aaataagaac tgatttgggt aagagatttg taaagttgtt gaatccttta gttgcatcac    2460
agaatttcga atacaaaatg tccaatattt tagacaaaac aaccgagtct aactttggat    2520
ttattactgt tctaccgggg gcattctctg cgtataggtt tgaagctgtg agaggccaac    2580
cattacagaa gtactttat ggtgaaatta tggaaaatga aggttttcat ttttttttctt    2640 ccaatatgta tcttgctgaa gatcgtattt tatgctttga agtggtcaca aaaaaaaatt    2700
gtaattggat tttgaaatac tgcagaagtt cttatgcttc aacagatgta ccggagaggg    2760
tccctgaatt tattcttcag aggaggcgtt ggttgaatgg ttcattttt gctagtgtat    2820 attccttttg tcattttttac agagtctgga gcagtggtca taatattggt agaaaactcc    2880
ttttgacggt tgaatttttt taccttttct tcaatacatt gatttcatgg ttttcattga    2940
gttcattttt cctagtcttt aggattctca ctgtttctat tgcactggca taccattcag    3000
catttaatgt gttgtccgtc atattcctgt ggctttatgg gatttgtacc ttatcaacat    3060
tcatactgtc attgggtaat aaacctaaaa gtactgagaa attttatgtt ctaacttgcg    3120 tcattttgc ggtgatgatg atttacatga tattctgcag tatattcatg agtgtcaaat    3180
ccttccaaaa tatattgaaa aacgatacca tcagctttga gggtttgatt accacagagg    3240
cttccaggga tattgttatc tctctgggct ccacttattg tttgtaccta atcagttcaa    3300
ttatctattt gcagccatgg catatgttga caagttttat tcagtatatt ttattgagtc    3360
cttcttacat caatgttttg aatatctatg cattttgtaa tgtccacgac ttatcatggg    3420
gtacaaaggg tgcaatggca atccgctgg gtaagattaa tactacagaa gatggtacgt    3480
tcaaaatgga agttctggtc tctagttcag agattcaagc aaaactacgat aaatatttga    3540 aagtttaaa tgacttcgat ccaaaatcag aatctcggcc tactgagcca tcttatgatg    3600
aaaaaaagac tggctattat gcaaacgtta gatctctcgt gattatcttt tgggtcatca    3660
caaatttcat catcgttgct gttgtcttag aaaccggtgg gattgcagat tatattgcta    3720
tgaaatccat atcaactgat gacactttag aaactgcaaa gaaggcggaa attcccttaa    3780
tgaccagtaa ggcctcaatt tattttaatg taatttatg gttagttgca ttatcggcat    3840
taataaggtt cattggttgc tcaatataca tgatagtaag gttttttaaa aaggttacat    3900
ttcgctaagg tacctcatgt aattagttat gtcacgctta cattcacgcc ctcccccac    3960 atccgctcta accgaaaagg aaggagttag acaacctgaa gtctaggtcc ctatttattt    4020
ttttatagtt atgttagtat taagaacgtt atttatattt caaattttc ttttttttct    4080 gtacagacgc gtgtacgcat gtaacattat actgaaaacc ttgcttgaga aggttttggg    4140
acgctcgaag gctttaattt gccggattag aagccgccga gcgggtgaca gccctccgaa    4200
ggaagactct cctccgtgcg tcctcgtctt caccggtcgc gttcctgaaa cgcagatgtg    4260
```

```
cctcgcgccg cactgctccg aacaataaag attctacaat actagctttt atggttatga    4320
agaggaaaaa ttggcagtaa cctggcccca caaaccttca aatgaacgaa tcaaattaac    4380
aaccatagga tgataatgcg attagttttt tagccttatt tctggggtaa ttaatcagcg    4440
aagcgatgat ttttgatcta ttaacagata tataaatgca aaaactgcat aaccacttta    4500
actaatactt tcaacatttt cggtttgtat tacttcttat tcaaatgtaa taaaagtatc    4560
aacaaaaaat tgttaatata cctctatact ttaacgtcaa ggagggatcc gccaccatgt    4620
cactccttta catcattctt ctattcacac aattcttact actgccaacc gatgcctttg    4680
ataggtctgc taacacaaat attgctgttt attggggtca aaactcagca ggaacgcaag    4740
aatccttagc tacttactgt gaatcttctg atgctgatat tttcctatta tctttcttga    4800
accaatttcc aacccttggt ttgaactttg ccaacgcatg ctctgatact ttttctgatg    4860
gcttacttca ctgcacccag attgctgaag atattgaaac ttgccagtcc ctaggaaaga    4920
aagttctatt atcattaggt ggtgcatctg gtagctacct cttttcagat gattctcaag    4980
cggaaacttt tgcacaaact ttatgggata ctttcggtga aggtacaggt gccagtgaga    5040
gaccatttga ctcagcagtc gttgatggtt ttgattttga tattgaaaac aacaacgaag    5100
taggctatag tgcgttagct accaagttaa gaactttgtt tgccgaaggt acaaagcaat    5160 attaccttt c tgccgcacca caatgtccat acccggatgc ttctgttggt gacttgttgg    5220
aaaatgcaga cattgatttt gcgttcatcc aattttacaa taattactgc agtgtgagtg    5280
gtcaattcaa ttgggatact tggttaacct atgctcaaac tgtatcccca aataaaaata    5340
tcaaactgtt cttaggttta cctggttctg cttctgctgc tggctctggt tatatttctg    5400
acacttcttt attggaatca actattgcag atattgcctc ttcaagttct tttggtggta    5460
ttgcgttatg ggatgcatct caagcctttt ccaacgagct aaatggtgaa ccatatgttg    5520 agatttgaa gaatttgcta acaagtgcta gccagaccgc cactactaca gttgccacct    5580
caaaaacctc agcagcctca acttcatctg cttcaacttc atctgcttca acttctcaga    5640
aaaagaccac acaatctacg acatctacac aaagtaaaag caaagttact ttatctccaa    5700
ctgcaagcag cgctatcaaa acatcaatta ctcaaactac aaaaacattg acgagtagca    5760
ccaagacaaa atctagtcta ggtaccacca caacagagag cactttaaat tcagttgcta    5820
tcacaagtat gaaaactact ctatcttccc aaataaccag tgctgccttg gtgacccctc    5880
aaacaactac tactagcata gtttcttcgg ccccaattca aacagctatc actagtactc    5940
tttcgccagc aacgaagagt tcttctgtcg tttccctaca gacagctact actagtacgc    6000 tttcccaac aacgaccagt acaagctcag gtagtacaag ctcaggtagt acaagctcag    6060
acagtacagc tcgtacattg gctaaagaat tgaatgctca atatgcggct ggtaaattga    6120
acggtaaatc tacctgtact gaaggtgaaa ttgcatgctc tgctgatggg aagttcgccg    6180
tttgtgatca tagcgcttgg gtttacatgg aatgtgcttc tggaaccaca tgttatgctt    6240
atgactccgg cgactcagtc tatacccaat gtaatttctc ttatttggaa agcaattact    6300
tttaattaat catgtaatta gttatgtcac gcttacattc acgccctccc cccacatccg    6360
ctctaaccga aaaggaagga gttagacaac ctgaagtcta ggtccctatt tattttttta    6420
tagttatgtt agtattaaga acgttattta tatttcaaat ttttcttttt ttctgtaca    6480 gacgcgtgta cgcatgtaac attatactga aaaccttgct tgagaaggtt ttgggacgct    6540
cgaaggcttt aatttgccgg attagaagcc gccgagcggg tgcagccct ccgaaggaag    6600 actctcctcc gtgcgtcctc gtcttcaccg gtcgcgttcc tgaaacgcag atgtgcctcg    6660
```

```
cgccgcactg ctccgaacaa taaagattct acaatactag cttttatggt tatgaagagg    6720
aaaaattggc agtaacctgg ccccacaaac cttcaaatga acgaatcaaa ttaacaacca    6780
taggatgata atgcgattag ttttttagcc ttatttctgg ggtaattaat cagcgaagcg    6840 atgattttg atctattaac agatatataa atgcaaaaac tgcataacca ctttaactaa     6900
tactttcaac attttcggtt tgtattactt cttattcaaa tgtaataaaa gtatcaacaa    6960
aaaattgtta atatacctct atactttaac gtcaaggagc tcgagatgag aatacaacta    7020
aatacaattg atttgcaatg tattattgca ctttcctgtc tggggcaatt tgttcacgcg    7080
gaagctaata gggaagattt aaagcagata gactttcaat ttcctgtatt ggaaagggca    7140
gctacaaaaa cgccttttcc ggattggctt agtgcattta ccgggttaaa agaatggcct    7200
gggttagatc caccttatat acctttagat ttcattgatt tcagtcaaat tccagattat    7260
aaggaatatg atcaaaacca ttgcgacagt gttccaaggg actcgtgctc tttcgattgc    7320
catcactgca ccgaacacga tgatgtgtac acatgttcca aactttccca gacatttgac    7380
gatggtcctt ctgcttccac tactaaatta ttggaccggt tgaagcataa ttccaccttc    7440
ttcaatttag gtgtcaatat agttcaacat ccagatatct atcaaagaat gcaaaaggag    7500
ggacacttaa tcggctcaca tacctggtct cacgtatatt tgccaaatgt atcgaatgaa    7560
aaaattatag ctcaaattga atggtccatc tgggcgatga atgctactgg caaccatacc    7620
cccaaatggt tcagacctcc atatggcgga atagataata gagtaagagc aataacaagg    7680
caatttggct tacaagccgt cttatgggat cacgatactt ttgattggag cctccttctc    7740
aatgattctg tcataactga acaagaaatt cttcaaaatg taataaactg gaacaagtca    7800
ggaaccggat taatattaga acacgattca acgaaaaaa ctgtcgatct tgccattaaa     7860
ataaataagt tgataggtga tgatcaatca acagtttctc attgtgtcgg cggaattgat    7920
tacataaaag aattcttgtc ctaagaattc tcatgtaatt agttatgtca cgcttacatt    7980
cacgccctcc ccccacatcc gctctaaccg aaaaggaagg agttagacaa cctgaagtct    8040
aggtccctat ttatttttt atagttatgt tagtattaag aacgttattt atatttcaaa     8100
tttttctttt ttttctgtac agacgcgtgt acgcatgtaa cattatactg aaaaccttgc    8160
ttgagaaggt tttgggacgc tcgaaggctt taatttgccg gattagaagc cgccgagcgg    8220
gtgacagccc tccgaaggaa gactctcctc cgtgcgtcct cgtcttcacc ggtcgcgttc    8280
ctgaaacgca gatgtgcctc gcgccgcact gctccgaaca ataaagattc tacaatacta    8340
gcttttatgg ttatgaagag gaaaaattgg cagtaacctg gccccacaaa ccttcaaatg    8400
aacgaatcaa attaacaacc ataggatgat aatgcgatta gttttttagc cttatttctg    8460
gggtaattaa tcagcgaagc gatgattttt gatctattaa cagatatata aatgcaaaaa    8520
ctgcataacc actttaacta atactttcaa cattttcggt ttgtattact cttattcaa     8580 atgtaataaa agtatcaaca aaaaattgtt aatatacctc tatactttaa cgtcaaggag    8640
gcggccgcca tggtgagcaa gggcgaggag ctgttcaccg gggtggtgcc catcctggtc    8700
gagctggacg gcgacgtaaa cggccacaag ttcagcgtgt ccggcgaggg cgagggcgat    8760
gccacctacg gcaagctgac cctgaagttc atctgcacca ccggcaagct gcccgtgccc    8820
tggcccaccc tcgtgaccac cttcggctac ggcctgcaat gcttcgcccg ctaccccgac    8880
cacatgaagc tgcacgactt cttcaagtcc gccatgcccg aaggctacgt ccaggagcgc    8940
accatcttct tcaaggacga cggcaactac aagacccgcg ccgaggtgaa gttcgagggc    9000
```

```
gacaccctgg tgaaccgcat cgagctgaag ggcatcgact tcaaggagga cggcaacatc    9060
ctggggcaca agctggagta caactacaac agccacaacg tctatatcat ggccgacaag    9120
cagaagaacg gcatcaaggt gaacttcaag atccgccaca acatcgagga cggcagcgtg    9180
cagctcgccg accactacca gcagaacacc cccatcggcg acggccccgt gctgctgccc    9240
gacaaccact acctgagcta ccagtccgcc ctgagcaaag accccaacga gaagcgcgat    9300
cacatggtcc tgctggagtt cgtgaccgcc gccgggatca ctctcggcat ggacgagctg    9360
tacaagtaat aatctagagg gccgcatcat gtaattagtt atgtcacgct tacattcacg    9420 ccctccccc acatccgctc taaccgaaaa ggaaggagtt agacaacctg aagtctaggt     9480
ccctatttat tttttatag ttatgttagt attaagaacg ttatttatat ttcaaatttt     9540 tcttttttt ctgtacagac gcgtgtacgc atgtaacatt atactgaaaa ccttgcttga     9600
gaaggttttg ggacgctcga aggctttaat ttgcggccct gcattaatga atcggccaac    9660
gcgcggggag aggcggtttg cgtattgggc gctcttccgc ttcctcgctc actgactcgc    9720
tgcgctcggt cgttcggctg cggcgagcgg tatcagctca ctcaaaggcg gtaatacggt    9780
tatccacaga atcaggggat aacgcaggaa agaacatgtg agcaaaaggc cagcaaaagc    9840
ccaggaaccg taaaaaggcc gcgttgctgg cgttttccca taggctccgc cccctgacg    9900 agcatcacaa aaatcgacgc tcaagtcaga ggtggcgaaa cccgacagga ctataaagat    9960
accaggcgtt ccccctgga agctccctcg tgcgctctcc tgttccgacc ctgccgctta    10020
ccggatacct gtccgccttt ctcccttcgg gaagcgtggc gctttctcat agctcacgct    10080
gtaggtatct cagttcggtg taggtcgttc gctccaagct gggctgtgtg cacgaacccc    10140
ccgttcagcc cgaccgctgc gccttatccg gtaactatcg tcttgagtcc aacccggtaa    10200
gacacgactt atcgccactg gcagcagcca ctggtaacag gattagcaga gcgaggtatg    10260
taggcggtgc tacagagttc ttgaagtggt ggcctaacta cggctacact agaaggacag    10320
tatttggtat ctgcgctctg ctgaagccag ttaccttcgg aaaaagagtt ggtagctctt    10380
gatccggcaa acaaaccacc gctggtagcg gtggtttttt tgtttgcaag cagcagatta    10440
cgcgcagaaa aaaaggatct caagaagatc ctttgatctt ttctacgggg tctgacgctc    10500
agtggaacga aaactcacgt taagggattt tggtcatgag attatcaaaa aggatcttca    10560
cctagatcct tttaaattaa aaatgaagtt ttaaatcaat ctaaagtata tatgagtaaa    10620
cttggtctga cagttaccaa tgcttaatca gtgaggcacc tatctcagcg atctgtctat    10680
ttcgttcatc catagttgcc tgactccccg tcgtgtagat aactacgata cgggagcgct    10740
taccatctgg ccccagtgct gcaatgatac cgcgagaccc acgctcaccg gctccagatt    10800
tatcagcaat aaaccagcca gccggaaggg ccgagcgcag aagtggtcct gcaactttat    10860
ccgcctccat ccagtctatt aattgttgcc gggaagctag agtaagtagt tcgccagtta    10920
atagtttgcg caacgttgtt ggcattgcta caggcatcgt ggtgtcactc tcgtcgtttg    10980
gtatggcttc attcagctcc ggttcccaac gatcaaggcg agttacatga tcccccatgt    11040
tgtgcaaaaa agcggttagc tccttcggtc ctccgatcgt tgtcagaagt aagttggccg    11100
cagtgttatc actcatggtt atggcagcac tgcataattc tcttactgtc atgccatccg    11160
taagatgctt ttctgtgact ggtgagtact caaccaagtc attctgagaa tagtgtatgc    11220
ggcgaccgag ttgctcttgc ccggcgtcaa tacgggataa tagtgtatca catagcagaa    11280
ctttaaaagt gctcatcatt ggaaaacgtt cttcggggcg aaaactctca aggatcttac    11340
cgctgttgag atccagttcg atgtaaccca ctcgtgcacc caactgatct tcagcatctt    11400
```

```
ttactttcac cagcgtttct gggtgagcaa aaacaggaag gcaaaatgcc gcaaaaaagg    11460
gaataagggc gacacggaaa tgttgaatac tcatactctt cctttttcaa tgggtaataa    11520
ctgatataat taaattgaag ctctaatttg tgagtttagt atacatgcat ttacttataa    11580
tacagttttt tagttttgct ggccgcatct tctcaaatat gcttcccagc ctgcttttct    11640
gtaacgttca ccctctacct tagcatccct tcccttttgca aatagtcctc ttccaacaat    11700
aataatgtca gatcctgtag agaccacatc atccacggtt ctatactgtt gacccaatgc    11760
gtctcccttg tcatctaaac ccacaccggg tgtcataatc aaccaatcgt aaccttcatc    11820
tcttccaccc atgtctcttt gagcaataaa gccgataaca aaatcttttgt cgctcttcgc    11880 aatgtcaaca gtacccttag tatattctcc agtagatagg gagcccttgc atgacaattc    11940
tgctaacatc aaaaggcctc taggttcctt tgttacttct tctgccgcct gcttcaaacc    12000
gctaacaata cctgggccca ccacaccgtg tgcattcgta atgtctgccc attctgctat    12060
tctgtataca cccgcagagt actgcaattt gactgtatta ccaatgtcag caaattttct    12120
gtcttcgaag agtaaaaaat tgtacttggc ggataatgcc tttagcggct taactgtgcc    12180
ctccatggaa aaatcagtca agatatccac atgtgttttt agtaaacaaa tttttgggacc    12240 taatgcttca actaactcca gtaattcctt ggtggtacga acatccaatg aagcacacaa    12300
gtttgtttgc ttttcgtgca tgatattaaa tagcttggca gcaacaggac taggatgagt    12360
agcagcacgt tccttatatg tagctttcga catgatttat cttcgtttcc tgcaggtttt    12420
tgttctgtgc agttgggtta agaatactgg gcaatttcat gtttcttcaa cactacatat    12480
gcgtatatat accaatctaa gtctgtgctc cttccttcgt tcttccttct gttcggagat    12540
taccgaatca aaaaatttc aaagaaaccg aaatcaaaaa aaagaataaa aaaaaatga    12600 tgaattgaat tgaaaagcta gcttatcgat gataagctgt caaagatgag aattaattcc    12660
acggactata gactatacta gatactccgt ctactgtacg atacacttcc gctcaggtcc    12720
ttgtccttta acgaggcctt accactcttt tgttactcta ttgatccagc tcagcaaagg    12780
cagtgtgatc taagattcta tcttcgcgat gtagtaaaac tagctagacc gagaaagaga    12840
ctagaaatgc aaaaggcact tctacaatgg ctgccatcat tattatccga tgtgacgctg    12900
cagcttctca atgatattcg aatacgcttt gaggagatac agcctaatat ccgacaaact    12960
gttttacaga tttacgatcg tacttgttac ccatcattga attttgaaca tccgaacctg    13020
ggagttttcc ctgaaacaga tagtatattt gaacctgtat aataatatat agtctagcgc    13080
tttacggaag acaatgtatg tatttcggtt cctggagaaa ctattgcatc tattgcatag    13140
gtaatcttgc acgtcgcatc cccggttcat tttctgcgtt tccatcttgc acttcaatag    13200
catatctttg ttaacgaagc atctgtgctt cattttgtag aacaaaaatg caacgcgaga    13260
gcgctaattt ttcaaacaaa gaatctgagc tgcattttta cagaacagaa atgcaacgcg    13320
aaagcgctat tttaccaacg aagaatctgt gcttcatttt tgtaaaacaa aaatgcaacg    13380
cgacgagagc gctaattttt caaacaaaga atctgagctg catttttaca gaacagaaat    13440
gcaacgcgag agcgctattt taccaacaaa gaatctatac ttcttttttg ttctacaaaa    13500
atgcatcccg agagcgctat ttttctaaca aagcatctta gattactttt tttctccttt    13560
gtgcgctcta taatgcagtc tcttgataac ttttttgcact gtaggtccgt taaggttaga    13620
agaaggctac tttggtgtct attttctctt ccataaaaaa agcctgactc cacttcccgc    13680
gtttactgat tactagcgaa gctgcgggtg cattttttca agataaaggc atccccgatt    13740
```

-continued

```
atattctata ccgatgtgga ttgcgcatac tttgtgaaca gaaagtgata gcgttgatga   13800
ttcttcattg gtcagaaaat tatgaacggt ttcttctatt ttgtctctat atactacgta   13860
taggaaatgt ttacattttc gtattgtttt cgattcactc tatgaatagt tcttactaca   13920
atttttttgt ctaaagagta atactagaga taaacataaa aaatgtagag gtcgagttta   13980
gatgcaagtt caaggagcga aaggtggatg ggtaggttat atagggatat agcacagaga   14040
tatatagcaa agagatactt ttgagcaatg tttgtggaag cggtattcgc aatgggaagc   14100
tccaccccgg ttgataatca gaaaagcccc aaaaacagga agattgtata agcaaatatt   14160
taaattgtaa acgttaatat tttgttaaaa ttcgcgttaa attttttgtta aatcagctca   14220 tttttttaacg aatagcccga aatcggcaaa atcccttata aatcaaaaga atagaccgag   14280
atagggttga gtgttgttcc agtttccaac aagagtccac tattaaagaa cgtggactcc   14340
aacgtcaaag ggcgaaaaag ggtctatcag ggcgatggcc cactacgtga accatcaccc   14400
taatcaagtt ttttggggtc gaggtgccgt aaagcagtaa atcggaaggg taaacgatg    14460 cccccattta gagcttgacg gggaaagccg gcgaacgtgg cgaaaagga agggaagaaa    14520 gcgaaaggag cggggggctag ggcggtggga agtgtagggg tcacgctggg cgtaaccacc   14580
acacccgccg cgcttaatgg ggcgctacag ggcgcgtggg gatgatccac tagt          14634
```

<210> SEQ ID NO 6
<211> LENGTH: 1237
<212> TYPE: DNA
<213> ORGANISM: Micrococcus sp. HL-2003

<400> SEQUENCE: 6

```
ggatccggta ccatggtgtt tatcgtcaat cttttctcct gcaccttatc tgaaaccacg     60
gttagctcaa taaaatctga agctacggtt agctcaacat ttactgccgt cacggccctg    120
caattggtgg ctgagggtaa gttgcagtcg gcgaagggtt tcggtggtgg tacgattcac    180
tacccaaccc tcgcggccga agcaccctgg tggacgccgg gccaaggcca tggttacgag    240
gcgatcacct acggctggct ggtcggcgaa ctgctgcgcc gcgccgatgg gcgtgggcct    300
ggtctgttag gcgctattgc cgtggttcct ggttacgttt cttacgagaa ctctatcaag    360
tggtggggac cgcgtctggc ttcttggggc tttgtcgttg cacggccgtt gggcctggac    420
tttcatgtgg gcctggcgga tgaagagttt tatcgtgttg cccatatagc gcgcagcaaa    480
gccaatgcag cactagataa cattgctgat gacaccgtcg gcagtataga tcctaagcgg    540
ttgggcgcta ttggctggtc aggtggcggc ggcgcgctta aactggcaac ggagcgcagc    600
acagtacgag ccattttgac cagtactaat aaacctgaat ggcgacgctt cgataaattc    660
ttatgtgcct gcgaggatga ccggattgct gagactaaga aatatgccaa cgcgttttat    720
aaaaatgccg acatgctcga agagttgacc cgtgaacaca gtatcgggcc ggataaaaca    780
ttattgacac aaactcggtt tggcttgggg tgcttggatc aaccgcaagc aggggttaaa    840
attcattttg aagagtacct tgatcaaacc catggattta tcaatttgac gccagtttca    900
cataaggcga gagcaaatct gattcagatg cctaatgcca cattcggcct tggcccgcgt    960
gcttttgggc atcctggtgc aggtggatcg gtaggttttg ccgacccccga acacgatgta   1020 gcgtttggtt tcgtgactaa tacattgggg ccttatgtag ttgagtttaa aagccgtcat   1080
ccctcatttt atgcatataa agatggattg gtgctgactg gaaatgacgt cgactatgtg   1140
actgattact atgcaacaaa gcatgctgta catttagatg atccacgtgc acagaagtta   1200
gtcggaatat tggccggttg tctgtaagct tctcgag                             1237
```

<210> SEQ ID NO 7
<211> LENGTH: 16558
<212> TYPE: DNA
<213> ORGANISM: Artificial sequence
<220> FEATURE:
<223> OTHER INFORMATION: Synthetic construct

<400> SEQUENCE: 7

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttgcca ccatggtgtt tatcgtcaat cttttctcct     540
gcaccttatc tgaaaccacg gttagctcaa taaaatctga agctacggtt agctcaacat     600
ttactgccgt cacggccctg caattggtgg ctgagggtaa gttgcagtcg gcgaagggtt     660
tcggtggtgg tacgattcac tacccaaccc tcgcggccga agcaccctgg tggacgccgg     720
gccaaggcca tggttacgag gcgatcacct acggctggct ggtcggcgaa ctgctgcgcc     780
gcgccgatgg gcgtgggcct ggtctgttag gcgctattgc cgtggttcct ggttacgttt     840
cttacgagaa ctctatcaag tggtggggac cgcgtctggc ttcttggggc tttgtcgttg     900
cacggccgtt gggcctggac tttcatgtgg gcctggcgga tgaagagttt atcgtgttg      960
cccatatagc gcgcagcaaa gccaatgcag cactagataa cattgctgat gacaccgtcg    1020
gcagtataga tcctaagcgg ttgggcgcta ttggctggtc aggtggcggc ggcgcgctta    1080
aactggcaac ggagcgcagc acagtacgag ccattttgac cagtactaat aaacctgaat    1140
ggcgacgctt cgataaattc ttatgtgcct gcgaggatga ccggattgct gagactaaga    1200
aatatgccaa cgcgttttat aaaaatgccg acatgctcga agagttgacc cgtgaacaca    1260
gtatcgggcc ggataaaaca ttattgacac aaactcggtt tggcttgggg tgcttggatc    1320
aaccgcaagc aggggttaaa attcattttg aagagtacct tgatcaaacc catggattta    1380
tcaatttgac gccagtttca cataaggcga gcaaatct gattcagatg cctaatgcca      1440
cattcggcct tggcccgcgt gcttttgggc atcctggtgc aggtggatcg gtaggttttg    1500
ccgaccccga acacgatgta gcgtttggtt tcgtgactaa tacattgggg ccttatgtag    1560
ttgagtttaa aagccgtcat ccctcatttt atgcatataa agatggattg gtgctgactg    1620
gaaatgacgt cgactatgtg actgattact atgcaacaaa gcatgctgta catttagatg    1680
atccacgtgc acagaagttg gtcggaatat tggccggttg tctgtaaccc gggtaatcat    1740
gtaattagtt atgtcacgct tacattcacg ccctccccc catccgctc taaccgaaaa     1800
ggaaggagtt agacaacctg aagtctaggt ccctatttat tttttatag ttatgttagt    1860
attaagaacg ttatttatat ttcaaatttt tcttttttt ctgtacagac gcgtgtacgc     1920
atgtaacatt atactgaaaa ccttgcttga aaggttttg gacgctcga aggctttaat      1980
ttgccggatt agaagccgcc gagcgggtga cagccctccg aaggaagact ctcctccgtg    2040
```

```
cgtcctcgtc ttcaccggtc gcgttcctga aacgcagatg tgcctcgcgc cgcactgctc    2100
cgaacaataa agattctaca atactagctt ttatggttat gaagaggaaa aattggcagt    2160
aacctggccc cacaaacctt caaatgaacg aatcaaatta acaaccatag gatgataatg    2220
cgattagttt tttagcctta tttctggggt aattaatcag cgaagcgatg attttttgatc   2280 tattaacaga tatataaatg caaaaactgc ataaccactt taactaatac tttcaacatt    2340
ttcggtttgt attacttctt attcaaatgt aataaaaagta tcaacaaaaa attgttaata   2400
tacctctata ctttaacgtc aaggaggcgc gccaccatga gtgatcaaaa taatcgatcg    2460
agaaatgaat atcactcaaa ccggaagaat gaaccttcct atgaactcca aaatgcacat    2520
agcgggctat ttcactcttc taatgaagaa ttaacaaaca ggaaccaaag atataccaat    2580
caaaatgcca gcatgggttc attcactcca gtccaatctt tgcaatttcc agaacaatct    2640
cagcaaacaa atatgcttta taacggtgac gatggcaata ataatactat caatgataac    2700
gaacgagaca tatatggagg ttttgtcaac caccatcgcc agcgtccccc accagcaact    2760
gcagaataca atgacgtttt taatacgaat agtcaacagc taccgtcgga acatcaatac    2820
aataacgtac cttcatatcc acttccttcg ataaatgtga ttcaaaccac tccagaactc    2880
atacataacg gctcacagac tatggccacc cccatcgaaa ggcccttctt taacgaaaac    2940
gactactatt ataataacag gaactctagg acgtcaccga gtattgcttc tagtagcgat    3000
ggttatgcag atcaggaagc taggcccatt ttggagcaac ccaacaataa catgaatagc    3060
ggtaatattc ctcaatacca tgaccaacct tttggataca acaatggtta ccatggccta    3120
caggcaaaag attactatga cgatccggag ggtggttata ttgatcagag aggagatgac    3180
tatcagatta attcatattt gggtagaaac ggtgaaatgg ttgatcctta cgattatgaa    3240
aacagtttaa gacatatgac tcctatggag cgtagagaat atcttcatga tgatagcaga    3300
cccgtaaacg atggaaaaga agaattagac agtgtgaaaa gcggttactc tcatagagac    3360
ttgggggaat atgacaagga tgattttttca agggatgacg agtacgatga tctcaacact   3420
attgataaat tacagtttca agctaatggt gtacctgcat catcctcggt gtcttctatc    3480
ggatctaaag aatccgacat aatagtaagc aatgataact taaccgcaaa tagagcacta    3540
aagagaagcg gtactgaaat taggaaattc aaactttgga atggtaattt tgttttcgat    3600
tctccaatca gtaagacgct attggaccaa tacgctacta caacagaaaa tgcaaacact    3660
ttaccaaatg agtttaagtt tatgagatat caagcagtta cttgcgaacc taatcaactt    3720
gcagagaaga atttcacggt gaggcagttg aagtatttaa ctccaaggga acggaattg     3780 atgctagtag tcacaatgta taatgaagac catatcctgt taggaagaac tttgaaaggt    3840
attatggaca atgtcaaata tatggtgaaa aaaaaaaatt caagcacttg ggggccggat    3900
gcatggaaaa agattgtcgt ttgtatcatt tcagatggta gatccaaaat taatgaacgc    3960
tcgctagcat tactaagttc gttaggttgt taccaggacg ggtttgctaa ggatgaaatt    4020
aatgaaaaaa aagtggcaat gcatgtctac gaacatacga caatgatcaa catcacaaat    4080
atttcggaat cagaggtttc attagaatgc aatcaaggta ctgttccaat acaacttttg    4140
ttttgtttga agagcaaaaa tcagaaaaaa attaactcac atagatgggc atttgaaggc    4200
tttgcagaat tactgcgtcc caatatcgtt acattgttag atgctggtac tatgccaggt    4260
aaagattcta tttaccagtt atggagagag ttcaggaatc caaatgttgg tggcgcatgt    4320
ggtgaaataa gaactgattt gggtaagaga tttgtaaagt tgttgaatcc tttagttgca    4380
tcacagaatt tcgaatacaa aatgtccaat attttagaca aaacaaccga gtctaacttt    4440
```

```
ggatttatta ctgttctacc gggggcattc tctgcgtata ggtttgaagc tgtgagaggc    4500
caaccattac agaagtactt ttatggtgaa attatggaaa atgaaggttt tcattttttt    4560
tcttccaata tgtatcttgc tgaagatcgt attttatgct ttgaagtggt cacaaaaaaa    4620
aattgtaatt ggattttgaa atactgcaga agttcttatg cttcaacaga tgtaccggag    4680
agggtccctg aatttattct tcagaggagg cgttggttga atggttcatt ttttgctagt    4740
gtatattcct tttgtcattt ttacagagtc tggagcagtg gtcataatat tggtagaaaa    4800
ctccttttga cggttgaatt ttttacctt tcttcaata cattgatttc atggttttca    4860
ttgagttcat ttttcctagt ctttaggatt ctcactgttt ctattgcact ggcataccat    4920
tcagcattta atgtgttgtc cgtcatattc ctgtggcttt atgggatttg taccttatca    4980
acattcatac tgtcattggg taataaacct aaaagtactg agaaatttta tgttctaact    5040
tgcgtcattt ttgcggtgat gatgatttac atgatattct gcagtatatt catgagtgtc    5100
aaatccttcc aaaatatatt gaaaaacgat accatcagct ttgagggttt gattaccaca    5160
gaggctttca gggatattgt tatctctctg ggctccactt attgtttgta cctaatcagt    5220
tcaattatct atttgcagcc atggcatatg ttgacaagtt ttattcagta tatttattg    5280 agtccttctt acatcaatgt tttgaatatc tatgcatttt gtaatgtcca cgacttatca    5340
tggggtacaa agggtgcaat ggcaaatccg ctgggtaaga ttaatactac agaagatggt    5400
acgttcaaaa tggaagttct ggtctctagt tcagagattc aagcaaacta cgataaatat    5460
ttgaaagttt taaatgactt cgatccaaaa tcagaatctc ggcctactga gccatcttat    5520
gatgaaaaaa agactggcta tatgcaaac gttagatctc tcgtgattat cttttgggtc    5580
atcacaaatt tcatcatcgt tgctgttgtc ttagaaaccg gtgggattgc agattatatt    5640
gctatgaaat ccatatcaac tgatgacact ttagaaactg caaagaaggc ggaaattccc    5700
ttaatgacca gtaaggcctc aatttatttt aatgtaattt tatggttagt tgcattatcg    5760
gcattaataa ggttcattgg ttgctcaata tacatgatag taaggttttt taaaaaggtt    5820
acatttcgct aaggtacctc atgtaattag ttatgtcacg cttacattca cgccctcccc    5880
ccacatccgc tctaaccgaa aaggaaggag ttagacaacc tgaagtctag gtccctattt    5940
atttttttat agttatgtta gtattaagaa cgttatttat atttcaaatt tttcttttt    6000 ttctgtacag acgcgtgtac gcatgtaaca ttatactgaa aaccttgctt gagaaggttt    6060
tgggacgctc gaaggcttta atttgccgga ttagaagccg ccgagcgggt gacagccctc    6120
cgaaggaaga ctctcctccg tgcgtcctcg tcttcaccgg tcgcgttcct gaaacgcaga    6180
tgtgcctcgc gccgcactgc tccgaacaat aaagattcta caatactagc ttttatggtt    6240
atgaagagga aaaattggca gtaacctggc cccacaaacc ttcaaatgaa cgaatcaaat    6300
taacaaccat aggatgataa tgcgattagt ttttagcct tatttctggg gtaattaatc    6360
agcgaagcga tgattttga tctattaaca gatatataaa tgcaaaaact gcataaccac    6420
tttaactaat acttcaaca ttttcggttt gtattacttc ttattcaaat gtaataaaag    6480
tatcaacaaa aaattgttaa tatacctcta tactttaacg tcaaggaggg atccgccacc    6540
atgtcactcc tttacatcat tcttctattc acacaattct tactactgcc aaccgatgcc    6600
tttgataggt ctgctaacac aaatattgct gtttattggg gtcaaaactc agcaggaacg    6660
caagaatcct tagctactta ctgtgaatct tctgatgctg atatttcct attatctttc    6720 ttgaaccaat ttccaaccct tggtttgaac tttgccaacg catgctctga acttttttct    6780
```

```
gatggcttac ttcactgcac ccagattgct gaagatattg aaacttgcca gtccctagga    6840
aagaaagttc tattatcatt aggtggtgca tctggtagct acctcttttc agatgattct    6900
caagcggaaa cttttgcaca aactttatgg gatactttcg gtgaaggtac aggtgccagt    6960
gagagaccat ttgactcagc agtcgttgat ggttttgatt ttgatattga aaacaacaac    7020
gaagtaggct atagtgcgtt agctaccaag ttaagaactt tgtttgccga aggtacaaag    7080
caatattacc tttctgccgc accacaatgt ccatacccgg atgcttctgt tggtgacttg    7140
ttggaaaatg cagacattga ttttgcgttc atccaatttt acaataatta ctgcagtgtg    7200
agtggtcaat tcaattggga tacttggtta acctatgctc aaactgtatc cccaaataaa    7260
aatatcaaac tgttcttagg tttacctggt tctgcttctg ctgctggctc tggttatatt    7320
tctgacactt ctttattgga atcaactatt gcagatattg cctcttcaag ttctttggt     7380 ggtattgcgt tatgggatgc atctcaagcc ttttccaacg agctaaatgg tgaaccatat    7440
gttgagattt tgaagaattt gctaacaagt gctagccaga ccgccactac tacagttgcc    7500
acctcaaaaa cctcagcagc ctcaacttca tctgcttcaa cttcatctgc ttcaacttct    7560
cagaaaaaga ccacacaatc tacgacatct acacaaagta aaagcaaagt tactttatct    7620
ccaactgcaa gcagcgctat caaaacatca attactcaaa ctacaaaaac attgacgagt    7680
agcaccaaga caaaatctag tctaggtacc accacaacag agagcacttt aaattcagtt    7740
gctatcacaa gtatgaaaac tactctatct tcccaaataa ccgtgctgc cttggtgacc     7800 cctcaaacaa ctactactag catagtttct tcggccccaa ttcaaacagc tatcactagt    7860
actctttcgc cagcaacgaa gagttcttct gtcgtttccc tacagacagc tactactagt    7920
acgctttccc caacaacgac cagtacaagc tcaggtagta caagctcagg tagtacaagc    7980
tcagacagta cagctcgtac attggctaaa gaattgaatg ctcaatatgc ggctggtaaa    8040
ttgaacggta aatctacctg tactgaaggt gaaattgcat gctctgctga tgggaagttc    8100
gccgtttgtg atcatagcgc ttgggtttac atggaatgtg cttctggaac acatgttat    8160 gcttatgact ccggcgactc agtctatacc caatgtaatt tctcttattt ggaaagcaat    8220 tactttaat taatcatgta attagttatg tcacgcttac attcacgccc tccccccaca    8280
tccgctctaa ccgaaaagga aggagttaga caacctgaag tctaggtccc tatttatttt    8340
tttatagtta tgttagtatt aagaacgtta tttatatttc aaattttctt ttttttctg    8400 tacagacgcg tgtacgcatg taacattata ctgaaaacct tgcttgagaa ggttttggga    8460
cgctcgaagg ctttaatttg ccggattaga agccgccgag cgggtgacag ccctccgaag    8520
gaagactctc ctccgtgcgt cctcgtcttc accggtcgcg ttcctgaaac gcagatgtgc    8580
ctcgcgccgc actgctccga acaataaaga ttctacaata ctagctttta tggttatgaa    8640
gaggaaaaat tggcagtaac ctggccccac aaaccttcaa atgaacgaat caaattaaca    8700
accataggat gataatgcga ttagttttttt agccttattt ctggggtaat taatcagcga    8760
agcgatgatt tttgatctat taacagatat ataaatgcaa aaactgcata accactttaa    8820
ctaatacttt caacattttc ggtttgtatt acttcttatt caaatgtaat aaaagtatca    8880
acaaaaaatt gttaatatac ctctatactt taacgtcaag gagctcgaga tgagaataca    8940 actaaatacà attgatttgc aatgtattat tgcactttcc tgtctggggc aatttgttca    9000
cgcggaagct aatagggaag atttaaagca gatagacttt caattcctg tattggaaag    9060 ggcagctaca aaaacgcctt ttccggattg gcttagtgca tttaccgggt taaagaatg     9120 gcctgggtta gatccaccct tataccctt agatttcatt gatttcagtc aaattccaga     9180
```

```
ttataaggaa tatgatcaaa accattgcga cagtgttcca agggactcgt gctctttcga   9240
ttgccatcac tgcaccgaac acgatgatgt gtacacatgt tccaaacttt cccagacatt   9300
tgacgatggt ccttctgctt ccactactaa attattggac cggttgaagc ataattccac   9360
cttcttcaat ttaggtgtca atatagttca acatccagat atctatcaaa gaatgcaaaa   9420
ggagggacac ttaatcggct cacatacctg gtctcacgta tatttgccaa atgtatcgaa   9480 tgaaaaatt atagctcaaa ttgaatggtc catctgggcg atgaatgcta ctggcaacca    9540 taccccaaa tggttcagac ctccatatgg cggaatagat aatagagtaa gagcaataac    9600
aaggcaattt ggcttacaag ccgtcttatg ggatcacgat acttttgatt ggagcctcct   9660
tctcaatgat tctgtcataa ctgaacaaga aattcttcaa aatgtaataa actggaacaa   9720
gtcaggaacc ggattaatat tagaacacga ttcaacggaa aaaactgtcg atcttgccat   9780
taaaataaat aagttgatag gtgatgatca atcaacagtt tctcattgtg tcggcggaat   9840
tgattacata aaagaattct tgtcctaaga attctcatgt aattagttat gtcacgctta   9900
cattcacgcc ctcccccac atccgctcta accgaaaagg aaggagttag acaacctgaa    9960
gtctaggtcc ctatttattt ttttatagtt atgttagtat taagaacgtt atttatattt  10020 caaattttc ttttttttct gtacagacgc gtgtacgcat gtaacattat actgaaaacc   10080
ttgcttgaga aggttttggg acgctcgaag gctttaattt gccggattag aagccgccga  10140
gcgggtgaca gccctccgaa ggaagactct cctccgtgcg tcctcgtctt caccggtcgc  10200
gttcctgaaa cgcagatgtg cctcgcgccg cactgctccg aacaataaag attctacaat  10260
actagctttt atggttatga agaggaaaaa ttggcagtaa cctggcccca caaaccttca   10320
aatgaacgaa tcaaattaac aaccatagga tgataatgcg attagttttt tagccttatt   10380
tctggggtaa ttaatcagcg aagcgatgat ttttgatcta ttaacagata tataaatgca   10440
aaaactgcat aaccacttta actaatactt tcaacatttt cggtttgtat tacttcttat   10500
tcaaatgtaa taaaagtatc aacaaaaaat tgttaatata cctctatact ttaacgtcaa   10560
ggaggcggcc gccatggtga gcaagggcga ggagctgttc accggggtgg tgcccatcct  10620
ggtcgagctg gacggcgacg taaacggcca caagttcagc gtgtccggcg agggcgaggg  10680
cgatgccacc tacggcaagc tgaccctgaa gttcatctgc accaccggca agctgcccgt  10740
gccctggccc accctcgtga ccaccttcgg ctacggcctg caatgcttcg cccgctaccc  10800
cgaccacatg aagctgcacg acttcttcaa gtccgccatg cccgaaggct acgtccagga  10860
gcgcaccatc ttcttcaagg acgacggcaa ctacaagacc cgcgccgagg tgaagttcga  10920
gggcgacacc ctggtgaacc gcatcgagct gaagggcatc gacttcaagg aggacggcaa  10980
catcctgggg cacaagctgg agtacaacta acaacagcca acgtctata tcatggccga   11040 caagcagaag aacggcatca aggtgaactt caagatccgc cacaacatcg aggacggcag  11100
cgtgcagctc gccgaccact accagcagaa caccccatc ggcgacgcc ccgtgctgct    11160 gcccgacaac cactacctga gctaccagtc cgccctgagc aaagacccca acgagaagcg  11220
cgatcacatg gtcctgctgg agttcgtgac cgccgcgggg atcactctcg gcatggacga  11280
gctgtacaag taataatcta gagggccgca tcatgtaatt agttatgtca cgcttacatt  11340
cacgccctcc cccacatccc gctctaaccg aaaggaagg agttagacaa cctgaagtct   11400
aggtccctat ttatttttt atagttatgt tagtattaag aacgttattt atatttcaaa   11460
tttttctttt ttttctgtac agacgcgtgt acgcatgtaa cattatactg aaaaccttgc   11520
```

```
ttgagaaggt tttgggacgc tcgaaggctt taatttgcgg ccctgcatta atgaatcggc    11580
caacgcgcgg ggagaggcgg tttgcgtatt gggcgctctt ccgcttcctc gctcactgac    11640
tcgctgcgct cggtcgttcg gctgcggcga gcggtatcag ctcactcaaa ggcggtaata    11700
cggttatcca cagaatcagg ggataacgca ggaaagaaca tgtgagcaaa aggccagcaa    11760
aagcccagga accgtaaaaa ggccgcgttg ctggcgtttt tccataggct ccgcccccct    11820
gacgagcatc acaaaaatcg acgctcaagt cagaggtggc gaaacccgac aggactataa    11880
agataccagg cgtttccccc tggaagctcc ctcgtgcgct ctcctgttcc gaccctgccg    11940
cttaccggat acctgtccgc ctttctccct tcgggaagcg tggcgctttc tcatagctca    12000
cgctgtaggt atctcagttc ggtgtaggtc gttcgctcca agctgggctg tgtgcacgaa    12060
ccccccgttc agcccgaccg ctgcgcctta tccggtaact atcgtcttga gtccaacccg    12120
gtaagacacg acttatcgcc actggcagca gccactggta acaggattag cagagcgagg    12180
tatgtaggcg gtgctacaga gttcttgaag tggtggccta actacggcta cactagaagg    12240
acagtatttg gtatctgcgc tctgctgaag ccagttacct tcggaaaaag agttggtagc    12300
tcttgatccg gcaaacaaac caccgctggt agcggtggtt ttttttgtttg caagcagcag    12360 attacgcgca gaaaaaaagg atctcaagaa gatcctttga tcttttctac ggggtctgac    12420
gctcagtgga acgaaaactc acgttaaggg attttggtca tgagattatc aaaaaggatc    12480
ttcacctaga tccttttaaa ttaaaaatga agttttaaat caatctaaag tatatatgag    12540
taaacttggt ctgacagtta ccaatgctta atcagtgagg cacctatctc agcgatctgt    12600
ctatttcgtt catccatagt tgcctgactc cccgtcgtgt agataactac gatacgggag    12660
cgcttaccat ctggccccag tgctgcaatg ataccgcgag acccacgctc accggctcca    12720
gatttatcag caataaacca gccagccgga agggccgagc gcagaagtgg tcctgcaact    12780
ttatccgcct ccatccagtc tattaattgt tgccgggaag ctagagtaag tagttcgcca    12840
gttaatagtt tgcgcaacgt tgttggcatt gctacaggca tcgtggtgtc actctcgtcg    12900
tttggtatgg cttcattcag ctccggttcc caacgatcaa ggcgagttac atgatccccc    12960
atgttgtgca aaaaagcggt tagctccttc ggtcctccga tcgttgtcag aagtaagttg    13020
gccgcagtgt tatcactcat ggttatggca gcactgcata attctcttac tgtcatgcca    13080
tccgtaagat gcttttctgt gactggtgag tactcaacca agtcattctg agaatagtgt    13140
atgcggcgac cgagttgctc ttgcccggcg tcaatacggg ataatagtgt atcacatagc    13200
agaactttaa aagtgctcat cattggaaaa cgttcttcgg ggcgaaaact ctcaaggatc    13260
ttaccgctgt tgagatccag ttcgatgtaa cccactcgtg cacccaactg atcttcagca    13320
tcttttactt tcaccagcgt ttctgggtga gcaaaaacag gaaggcaaaa tgccgcaaaa    13380
aagggaataa gggcgacacg gaaatgttga atactcatac tcttcctttt tcaatgggta    13440
ataactgata taattaaatt gaagctctaa tttgtgagtt tagtatacat gcatttactt    13500
ataatacagt ttttagtttt tgctggccgc atcttctcaa atatgcttcc cagcctgctt    13560
ttctgtaacg ttcaccctct accttagcat cccttccctt tgcaaatagt cctcttccaa    13620
caataataat gtcagatcct gtagagacca catcatccac ggttctatac tgttgaccca    13680
atgcgtctcc cttgtcatct aaacccacac cgggtgtcat aatcaaccaa tcgtaacctt    13740
catctcttcc acccatgtct ctttgagcaa taaagccgat aacaaatctt tgtcgctct     13800 tcgcaatgtc aacagtaccc ttagtatatt ctccagtaga tagggagccc ttgcatgaca    13860
attctgctaa catcaaaagg cctctaggtt cctttgttac ttcttctgcc gcctgcttca    13920
```

```
aaccgctaac aatacctggg cccaccacac cgtgtgcatt cgtaatgtct gcccattctg   13980
ctattctgta tacacccgca gagtactgca atttgactgt attaccaatg tcagcaaatt   14040
ttctgtcttc gaagagtaaa aaattgtact tggcggataa tgcctttagc ggcttaactg   14100
tgccctccat ggaaaaatca gtcaagatat ccacatgtgt ttttagtaaa caaattttgg   14160
gacctaatgc ttcaactaac tccagtaatt ccttggtggt acgaacatcc aatgaagcac   14220
acaagtttgt ttgcttttcg tgcatgatat taaatagctt ggcagcaaca ggactaggat   14280
gagtagcagc acgttcctta tatgtagctt tcgacatgat ttatcttcgt ttcctgcagg   14340
tttttgttct gtgcagttgg gttaagaata ctgggcaatt tcatgtttct tcaacactac   14400
atatgcgtat atataccaat ctaagtctgt gctccttcct tcgttcttcc ttctgttcgg   14460
agattaccga atcaaaaaaa tttcaaagaa accgaaatca aaaaaagaa taaaaaaaa   14520 atgatgaatt gaattgaaaa gctagcttat cgatgataag ctgtcaaaga tgagaattaa   14580
ttccacggac tatagactat actagatact ccgtctactg tacgatacac ttccgctcag   14640
gtccttgtcc tttaacgagg ccttaccact cttttgttac tctattgatc cagctcagca   14700
aaggcagtgt gatctaagat tctatcttcg cgatgtagta aaactagcta gaccgagaaa   14760
gagactagaa atgcaaaagg cacttctaca atggctgcca tcattattat ccgatgtgac   14820
gctgcagctt ctcaatgata ttcgaatacg ctttgaggag atacagccta atatccgaca   14880
aactgtttta cagatttacg atcgtacttg ttacccatca ttgaattttg aacatccgaa   14940
cctgggagtt ttccctgaaa cagatagtat atttgaacct gtataataat atatagtcta   15000
gcgctttacg gaagacaatg tatgtatttc ggttcctgga gaaactattg catctattgc   15060
ataggtaatc ttgcacgtcg catccccggt tcattttctg cgtttccatc ttgcacttca   15120
atagcatatc tttgttaacg aagcatctgt gcttcatttt gtagaacaaa aatgcaacgc   15180
gagagcgcta attttcaaa caaagaatct gagctgcatt tttacagaac agaaatgcaa   15240
cgcgaaagcg ctattttacc aacgaagaat ctgtgcttca tttttgtaaa acaaaaatgc   15300
aacgcgacga gagcgctaat ttttcaaaca aagaatctga gctgcatttt tacagaacag   15360
aaatgcaacg cgagagcgct attttaccaa caaagaatct atacttcttt tttgttctac   15420
aaaaatgcat cccgagagcg ctattttct aacaaagcat cttagattac ttttttttctc   15480 ctttgtgcgc tctataatgc agtctcttga taactttttg cactgtaggt ccgttaaggt   15540
tagaagaagg ctactttggt gtctattttc tcttccataa aaaagcctg actccacttc   15600 ccgcgtttac tgattactag cgaagctgcg ggtgcatttt tcaagataa aggcatcccc   15660 gattatattc tataccgatg tggattgcgc atactttgtg aacagaaagt gatagcgttg   15720
atgattcttc attggtcaga aaattatgaa cggtttcttc tattttgtct ctatatacta   15780
cgtataggaa atgtttacat tttcgtattg ttttcgattc actctatgaa tagttcttac   15840
tacaattttt ttgtctaaag agtaatacta gagataaaca taaaaatgt agaggtcgag   15900 tttagatgca agttcaagga gcgaaaggtg gatgggtagg ttatataggg atatagcaca   15960
gagatatata gcaaagagat acttttgagc aatgtttgtg gaagcggtat tcgcaatggg   16020
aagctccacc ccggttgata atcagaaaag ccccaaaaac aggaagattg tataagcaaa   16080
tatttaaatt gtaaacgtta atattttgtt aaaattcgcg ttaaattttt gttaaatcag   16140 ctcattttt aacgaatagc ccgaaatcgg caaaatccct tataaatcaa agaatagac   16200 cgagatagggg ttgagtgttg ttccagtttc caacaagagt ccactattaa agaacgtgga   16260
```

| | | | |
|---|---|---|---|
| ctccaacgtc | aaagggcgaa | aaagggtcta tcagggcgat | ggcccactac gtgaaccatc | 16320 |
| accctaatca | agtttttttgg | ggtcgaggtg ccgtaaagca | gtaaatcgga agggtaaacg | 16380 |
| gatgcccca | tttagagctt | gacggggaaa gccggcgaac | gtggcgagaa aggaagggaa | 16440 |
| gaaagcgaaa | ggagcggggg | ctagggcggt gggaagtgta | ggggtcacgc tgggcgtaac | 16500 |
| caccacaccc | gccgcgctta | atggggcgct acagggcgcg | tggggatgat ccactagt | 16558 |

<210> SEQ ID NO 8
<211> LENGTH: 12544
<212> TYPE: DNA
<213> ORGANISM: Artificial sequence
<220> FEATURE:
<223> OTHER INFORMATION: Synthetic construct

<400> SEQUENCE: 8

| | | | |
|---|---|---|---|
| ggggaattgt | gagcggataa | caattcccct ctagaaataa | ttttgtttaa ctttaagaag | 60 |
| gagatatacc | atggtgttta | tcgtcaatct tttctcctgc | accttatctg aaaccacggt | 120 |
| tagctcaata | aaatctgaag | ctacggttag ctcaacattt | actgccgtca cggccctgca | 180 |
| attggtggct | gagggtaagt | tgcagtcggc gaagggtttc | gtggtggta cgattcacta | 240 |
| cccaaccctc | gcggccgaag | caccctggtg gacgccgggc | caaggccatg gttacgaggc | 300 |
| gatcacctac | ggctggctgg | tcggcgaact gctgcgccgc | gccgatgggc gtgggcctgg | 360 |
| tctgttaggc | gctattgccg | tggttcctgg ttacgtttct | tacgagaact ctatcaagtg | 420 |
| gtggggaccg | cgtctggctt | cttggggctt tgtcgttgca | cggccgttgg gcctggactt | 480 |
| tcatgtgggc | ctggcggatg | aagagtttta tcgtgttgcc | catatagcgc gcagcaaagc | 540 |
| caatgcagca | ctagataaca | ttgctgatga caccgtcggc | agtatagatc taagcggtt | 600 |
| gggcgctatt | ggctggtcag | gtggcggcgg cgcgcttaaa | ctggcaacgg agcgcagcac | 660 |
| agtacgagcc | attttgacca | gtactaataa acctgaatgg | cgacgcttcg ataaattctt | 720 |
| atgtgcctgc | gaggatgacc | ggattgctga gactaagaaa | tatgccaacg cgttttataa | 780 |
| aaatgccgac | atgctcgaag | agttgacccg tgaacacagt | atcgggccgg ataaaacatt | 840 |
| attgacacaa | actcggtttg | gcttggggtg cttggatcaa | ccgcaagcag gggttaaaat | 900 |
| tcattttgaa | gagtaccttg | atcaaaccca tggatttatc | aatttgacgc cagtttcaca | 960 |
| taaggcgaga | gcaaatctga | ttcagatgcc taatgccaca | ttcggccttg cccgcgtgc | 1020 |
| ttttgggcat | cctggtgcag | gtggatcggt aggttttgcc | gaccccgaac acgatgtagc | 1080 |
| gtttggtttc | gtgactaata | cattggggcc ttatgtagtt | gagtttaaaa gccgtcatcc | 1140 |
| ctcattttat | gcatataaag | atggattggt gctgactgga | aatgacgtcg actatgtgac | 1200 |
| tgattactat | gcaacaaagc | atgctgtaca tttagatgat | ccacgtgcac agaagttggt | 1260 |
| cggaatattg | gccggttgtc | tgtaaggatc cagaaataat | tttgtttaac tttaagaagg | 1320 |
| agagaattca | tgtcactcct | ttacatcatt cttctattca | cacaattctt actactgcca | 1380 |
| accgatgcct | tgataggtc | tgctaacaca aatattgctg | tttattgggg tcaaaactca | 1440 |
| gcaggaacgc | aagaatcctt | agctacttac tgtgaatctt | ctgatgctga tatttttccta | 1500 |
| ttatctttct | tgaaccaatt | tccacccctt ggtttgaact | tgccaacgc atgctctgat | 1560 |
| acttttctg | atggcttact | tcactgcacc cagattgctg | aagatattga aacttgccag | 1620 |
| tccctaggaa | agaaagttct | attatcatta ggtggtgcat | ctggtagcta cctctttttca | 1680 |
| gatgattctc | aagcggaaac | ttttgcacaa actttatggg | atacctttcgg tgaaggtaca | 1740 |
| ggtgccagtg | agagaccatt | tgactcagca gtcgttgatg | gttttgattt tgatattgaa | 1800 |

```
aacaacaacg aagtaggcta tagtgcgtta gctaccaagt taagaacttt gtttgccgaa    1860
ggtacaaagc aatattacct ttctgccgca ccacaatgtc catacccgga tgcttctgtt    1920
ggtgacttgt tggaaaatgc agacattgat tttgcgttca tccaatttta caataattac    1980
tgcagtgtga gtggtcaatt caattgggat acttggttaa cctatgctca aactgtatcc    2040
ccaaataaaa atatcaaact gttcttaggt ttacctggtt ctgcttctgc tgctggctct    2100
ggttatattt ctgacacttc tttattggaa tcaactattg cagatattgc ctcttcaagt    2160
tcttttggtg gtattgcgtt atgggatgca tctcaagcct tttccaacga gctaaatggt    2220
gaaccatatg ttgagatttt gaagaatttg ctaacaagtg ctagccagac cgccactact    2280
acagttgcca cctcaaaaac ctcagcagcc tcaacttcat ctgcttcaac ttcatctgct    2340
tcaacttctc agaaaaagac cacacaatct acgacatcta cacaaagtaa aagcaaagtt    2400
actttatctc caactgcaag cagcgctatc aaaacatcaa ttactcaaac tacaaaaaca    2460
ttgacgagta gcaccaagac aaaatctagt ctaggtacca ccacaacaga gagcacttta    2520
aattcagttg ctatcacaag tatgaaaact actctatctt cccaaataac cagtgctgcc    2580
ttggtgaccc ctcaaacaac tactactagc atagtttctt cggccccaat tcaaacagct    2640
atcactagta ctctttcgcc agcaacgaag agttcttctg tcgtttccct acagacagct    2700
actactagta cgctttcccc aacaacgacc agtacaagct caggtagtac aagctcaggt    2760
agtacaagct cagacagtac agctcgtaca ttggctaaag aattgaatgc tcaatatgcg    2820
gctggtaaat tgaacggtaa atctacctgt actgaaggtg aaattgcatg ctctgctgat    2880
gggaagttcg ccgtttgtga tcatagcgct tgggtttaca tggaatgtgc ttctggaacc    2940
acatgttatg cttatgactc cggcgactca gtctataccc aatgtaattt ctcttatttg    3000
gaaagcaatt acttttaagc ggccgcataa tgcttaagtc gaacagaaag taatcgtatt    3060
gtacacggcc gcataatcga aattaatacg actcactata ggggaattgt gagcggataa    3120
caattcccca tcttagtata ttagttaagt ataagaagga gatatacata tgagtgatca    3180
aaataatcga tcgagaaatg aatatcactc aaaccggaag aatgaacctt cctatgaact    3240
ccaaaatgca catagcgggc tatttcactc ttctaatgaa gaattaacaa acaggaacca    3300
aagatatacc aatcaaaatg ccagcatggg ttcattcact ccagtccaat ctttgcaatt    3360
tccagaacaa tctcagcaaa caaatatgct ttataacggt gacgatggca ataataatac    3420
tatcaatgat aacgaacgag acatatatgg aggttttgtc aaccaccatc gccagcgtcc    3480
cccaccagca actgcagaat acaatgacgt ttttaatacg aatagtcaac agctaccgtc    3540
ggaacatcaa tacaataacg taccttcata tccacttcct tcgataaatg tgattcaaac    3600
cactccagaa ctcatacata acggctcaca gactatggcc accccatcg aaaggccctt    3660 ctttaacgaa aacgactact attataataa caggaactct aggacgtcac cgagtattgc    3720
ttctagtagc gatggttatg cagatcagga agctaggccc attttggagc aacccaacaa    3780
taacatgaat agcggtaata ttcctcaata ccatgaccaa cctttggat acaacaatgg    3840 ttaccatggc ctacaggcaa aagattacta tgacgatccg gagggtggtt atattgatca    3900
gagaggagat gactatcaga ttaattcata tttgggtaga acggtgaaa tggttgatcc    3960 ttacgattat gaaaacagtt taagacatat gactcctatg gagcgtagag aatatcttca    4020
tgatgatagc agaccgtaa acgatggaaa agaagaatta gacagtgtga aaagcggtta    4080
ctctcataga gacttggggg aatatgacaa ggatgatttt tcaagggatg acgagtacga    4140
```

```
tgatctcaac actattgata aattacagtt tcaagctaat ggtgtacctg catcatcctc   4200
ggtgtcttct atcggatcta aagaatccga cataatagta agcaatgata acttaaccgc   4260
aaatagagca ctaaagagaa gcggtactga aattaggaaa ttcaaacttt ggaatggtaa   4320
ttttgttttc gattctccaa tcagtaagac gctattggac caatacgcta ctacaacaga   4380
aaatgcaaac actttaccaa atgagtttaa gtttatgaga tatcaagcag ttacttgcga   4440
acctaatcaa cttgcagaga agaatttcac ggtgaggcag ttgaagtatt taactccaag   4500
ggaaacggaa ttgatgctag tagtcacaat gtataatgaa gaccatatcc tgttaggaag   4560
aactttgaaa ggtattatgg acaatgtcaa atatatggtg aaaaaaaaaa attcaagcac   4620
ttgggggccg gatgcatgga aaaagattgt cgtttgtatc atttcagatg gtagatccaa   4680
aattaatgaa cgctcgctag cattactaag ttcgttaggt tgttaccagg acgggtttgc   4740
taaggatgaa attaatgaaa aaaaagtggc aatgcatgtc tacgaacata cgacaatgat   4800
caacatcaca aatatttcgg aatcagaggt ttcattagaa tgcaatcaag gtactgttcc   4860
aatacaactt ttgttttgtt tgaaagagca aaatcagaaa aaaattaact cacatagatg   4920
ggcatttgaa ggctttgcag aattactgcg tcccaatatc gttacattgt tagatgctgg   4980
tactatgcca ggtaaagatt ctatttacca gttatggaga gagttcagga atccaaatgt   5040
tggtggcgca tgtggtgaaa taagaactga tttgggtaag agatttgtaa agttgttgaa   5100
tcctttagtt gcatcacaga atttcgaata caaaatgtcc aatattttag acaaaacaac   5160
cgagtctaac tttggattta ttactgttct accgggggca ttctctgcgt ataggtttga   5220
agctgtgaga ggccaaccat tacagaagta cttttatggt gaaattatgg aaaatgaagg   5280
ttttcatttt ttttcttcca atatgtatct tgctgaagat cgtatttttat gctttgaagt   5340 ggtcacaaaa aaaaattgta attggatttt gaaatactgc agaagttctt atgcttcaac   5400
agatgtaccg gagagggtcc ctgaatttat tcttcagagg aggcgttggt tgaatggttc   5460 atttttttgct agtgtatatt cctttttgtca tttttacaga gtctggagca gtggtcataa   5520
tattggtaga aaactccttt tgacggttga attttttttac cttttcttca atacattgat   5580
ttcatggttt tcattgagtt catttttcct agtcttaggg attctcactg tttctattgc   5640
actggcatac cattcagcat ttaatgtgtt gtccgtcata ttcctgtggc tttatgggat   5700
ttgtaccttc tcaacattca tactgtcatt gggtaataaa cctaaaagta ctgagaaatt   5760
ttatgttcta acttgcgtca ttttttgcggt gatgatgatt tacatgatat tctgcagtat   5820
attcatgagt gtcaaatcct tccaaaatat attgaaaaac gataccatca gctttgaggg   5880
tttgattacc acagaggctt tcagggatat tgttatctct ctgggctcca cttattgttt   5940
gtacctaatc agttcaatta tctatttgca gccatggcat atgttgacaa gttttattca   6000 gtatattta ttgagtcctt cttacatcaa tgttttgaat atctatgcat tttgtaatgt   6060
ccacgactta tcatgggta caaagggtgc aatggcaaat ccgctgggta agattaatac   6120
tacagaagat ggtacgttca aaatggaagt tctggtctct agttcagaga ttcaagcaaa   6180
ctacgataaa tatttgaaag ttttaaatga cttcgatcca aaatcagaat ctcggcctac   6240
tgagccatct tatgatgaaa aaaagactgg ctattatgca aacgttagat ctctcgtgat   6300
tatcttttgg gtcatcacaa atttcatcat cgttgctgtt gtcttagaaa ccggtgggat   6360
tgcagattat attgctatga atccatatc aactgatgac actttagaaa ctgcaaagaa   6420
ggcggaaatt cccttaatga ccagtaaggc ctcaattat tttaatgtaa ttttatggtt   6480
agttgcatta tcggcattaa taaggttcat tggttgctca atatacatga tagtaaggtt   6540
```

```
ttttaaaaag gttacatttc gctaaggtac cagaaataat tttgtttaac tttaagaagg    6600
agactcgaga tgagaataca actaaataca attgatttgc aatgtattat tgcactttcc    6660
tgtctggggc aatttgttca cgcggaagct aatagggaag atttaaagca gatagacttt    6720
caatttcctg tattggaaag ggcagctaca aaaacgcctt ttccggattg gcttagtgca    6780
tttaccgggt taaaagaatg gcctgggtta gatccacctt atatacctttt agatttcatt    6840 gatttcagtc aaattccaga ttataaggaa tatgatcaaa accattgcga cagtgttcca    6900
agggactcgt gctctttcga ttgccatcac tgcaccgaac acgatgatgt gtacacatgt    6960
tccaaacttt cccagacatt tgacgatggt ccttctgctt ccactactaa attattggac    7020
cggttgaagc ataattccac cttcttcaat ttaggtgtca atatagttca acatccagat    7080
atctatcaaa gaatgcaaaa ggagggacac ttaatcggct cacatacctg gtctcacgta    7140
tatttgccaa atgtatcgaa tgaaaaaatt atagctcaaa ttgaatggtc catctgggcg    7200
atgaatgcta ctggcaacca tacccccaaa tggttcagac ctccatatgg cggaatagat    7260
aatagagtaa gagcaataac aaggcaattt ggcttacaag ccgtcttatg ggatcacgat    7320
acttttgatt ggagcctcct tctcaatgat tctgtcataa ctgaacaaga aattcttcaa    7380
aatgtaataa actggaacaa gtcaggaacc ggattaatat tagaacacga ttcaacggaa    7440
aaaactgtcg atcttgccat taaaataaat aagttgatag gtgatgatca atcaacagtt    7500
tctcattgtg tcggcggaat tgattacata aaagaattct tgtcctaatt aattaaccta    7560
ggctgctgcc accgctgagc aataactagc ataacccctt ggggcctcta acgggtctt    7620 gaggggtttt ttgctgaaag gaggaactat atccggattg gcgaatggga cgcgccctgt    7680
agcggcgcat taagcgcggc gggtgtggtg gttacgcgca gcgtgaccgc tacacttgcc    7740
agcgccctag cgcccgctcc tttcgctttc ttcccttcct ttctcgccac gttcgccggc    7800
tttccccgtc aagctctaaa tcgggggctc cctttagggt tccgatttag tgctttacgg    7860
cacctcgacc ccaaaaaact tgattagggt gatggttcac gtagtgggcc atcgccctga    7920
tagacggttt ttcgcccttt gacgttggag tccacgttct ttaatagtgg actcttgttc    7980
caaactggaa caacactcaa ccctatctcg gtctattctt ttgatttata agggattttg    8040
ccgatttcgg cctattggtt aaaaaatgag ctgatttaac aaaaatttaa cgcgaatttt    8100
aacaaaatat taacgtttac aatttctggc ggcacgatgg catgagatta tcaaaaagga    8160
tcttcaccta gatccttta aattaaaaat gaagttttaa atcaatctaa agtatatatg    8220
agtaaacttg gtctgacagt taccaatgct taatcagtga ggcacctatc tcagcgatct    8280
gtctatttcg ttcatccata gttgcctgac tccccgtcgt gtagataact acgatacggg    8340
agggcttacc atctggcccc agtgctgcaa tgataccgcg agaccacgc tcaccggctc    8400 cagatttatc agcaataaac cagccagccg gaagggccga gcgcagaagt ggtcctgcaa    8460
ctttatccgc ctccatccag tctattaatt gttgccggga agctagagta agtagttcgc    8520
cagttaatag tttgcgcaac gttgttgcca ttgctacagg catcgtggtg tcacgctcgt    8580
cgtttggtat ggcttcattc agctccggtt cccaacgatc aaggcgagtt acatgatccc    8640
ccatgttgtg caaaaaagcg gttagctcct tcggtcctcc gatcgttgtc agaagtaagt    8700
tggccgcagt gttatcactc atggttatgg cagcactgca taattctctt actgtcatgc    8760
catccgtaag atgcttttct gtgactggtg agtactcaac caagtcattc tgagaatagt    8820
gtatgcggcg accgagttgc tcttgcccgg cgtcaatacg ggataatacc gcgccacata    8880
```

```
gcagaacttt aaaagtgctc atcattggaa aacgttcttc ggggcgaaaa ctctcaagga    8940
tcttaccgct gttgagatcc agttcgatgt aacccactcg tgcacccaac tgatcttcag    9000
catcttttac tttcaccagc gtttctgggt gagcaaaaac aggaaggcaa aatgccgcaa    9060
aaaagggaat aagggcgaca cggaaatgtt gaatactcat actcttcctt tttcaatcat    9120
gattgaagca tttatcaggg ttattgtctc atgagcggat acatatttga atgtatttag    9180
aaaaataaac aaataggtca tgaccaaaat cccttaacgt gagttttcgt tccactgagc    9240
gtcagacccc gtagaaaaga tcaaaggatc ttcttgagat cctttttttc tgcgcgtaat    9300
ctgctgcttg caaacaaaaa aaccaccgct accagcggtg gtttgtttgc cggatcaaga    9360
gctaccaact ctttttccga aggtaactgg cttcagcaga gcgcagatac caaatactgt    9420
ccttctagtg tagccgtagt taggccacca cttcaagaac tctgtagcac cgcctacata    9480
cctcgctctg ctaatcctgt taccagtggc tgctgccagt ggcgataagt cgtgtcttac    9540
cgggttggac tcaagacgat agttaccgga taaggcgcag cggtcgggct gaacggggg    9600
ttcgtgcaca gcccagct tggagcgaac gacctacacc gaactgagat acctacagcg    9660
tgagctatga gaaagcgcca cgcttcccga agggagaaag gcggacaggt atccggtaag    9720
cggcagggtc ggaacaggag agcgcacgag ggagcttcca gggggaaacg cctggtatct    9780
ttatagtcct gtcgggtttc gccacctctg acttgagcgt cgatttttgt gatgctcgtc    9840
aggggggcg agcctatgga aaaacgccag caacgcggcc tttttacggt tcctggcctt    9900
ttgctggcct tttgctcaca tgttctttcc tgcgttatcc cctgattctg tggataaccg    9960
tattaccgcc tttgagtgag ctgataccgc tcgccgcagc cgaacgaccg agcgcagcga   10020
gtcagtgagc gaggaagcgg aagagcgcct gatgcggtat tttctcctta cgcatctgtg   10080
cggtatttca caccgcatat atggtgcact ctcagtacaa tctgctctga tgccgcatag   10140
ttaagccagt atacactccg ctatcgctac gtgactgggt catggctgcg ccccgacacc   10200
cgccaacacc cgctgacgcg ccctgacggg cttgtctgct cccggcatcc gcttacagac   10260
aagctgtgac cgtctccggg agctgcatgt gtcagaggtt ttcaccgtca tcaccgaaac   10320
gcgcgaggca gctgcggtaa agctcatcag cgtggtcgtg aagcgattca cagatgtctg   10380
cctgttcatc cgcgtccagc tcgttgagtt tctccagaag cgttaatgtc tggcttctga   10440
taaagcgggc catgttaagg gcggtttttt cctgtttggt cactgatgcc tccgtgtaag   10500
ggggatttct gttcatgggg gtaatgatac cgatgaaacg agagaggatg ctcacgatac   10560
gggttactga tgatgaacat gcccggttac tggaacgttg tgagggtaaa caactggcgg   10620
tatggatgcg gcgggaccag agaaaaatca ctcagggtca atgccagcgc ttcgttaata   10680
cagatgtagg tgttccacag ggtagccagc agcatcctgc gatgcagatc cggaacataa   10740
tggtgcaggg cgctgacttc cgcgtttcca gactttacga aacacggaaa ccgaagacca   10800
ttcatgttgt tgctcaggtc gcagacgttt gcagcagca gtcgcttcac gttcgctcgc   10860
gtatcggtga ttcattctgc taaccagtaa ggcaaccccg ccagcctagc cgggtcctca   10920
acgacaggag cacgatcatg ctagtcatgc cccgcgccca ccggaaggag ctgactgggt   10980
tgaaggctct caagggcatc ggtcgagatc ccggtgccta atgagtgagc taacttacat   11040
taattgcgtt gcgctcactg cccgctttcc agtcgggaaa cctgtcgtgc cagctgcatt   11100
aatgaatcgg ccaacgcgcg gggagaggcg gtttgcgtat tgggcgccag ggtggttttt   11160
cttttcacca gtgagacggg caacagctga ttgcccttca ccgcctggcc ctgagagagt   11220
tgcagcaagc ggtccacgct ggtttgcccc agcaggcgaa aatcctgttt gatggtggtt   11280
```

```
aacggcggga tataacatga gctgtcttcg gtatcgtcgt atcccactac cgagatgtcc    11340
gcaccaacgc gcagcccgga ctcggtaatg gcgcgcattg cgcccagcgc catctgatcg    11400
ttggcaacca gcatcgcagt gggaacgatg ccctcattca gcatttgcat ggtttgttga    11460
aaaccggaca tggcactcca gtcgccttcc cgttccgcta tcggctgaat ttgattgcga    11520
gtgagatatt tatgccagcc agccagacgc agacgcgccg agacagaact taatgggccc    11580
gctaacagcg cgatttgctg gtgacccaat gcgaccagat gctccacgcc cagtcgcgta    11640
ccgtcttcat gggagaaaat aatactgttg atgggtgtct ggtcagagac atcaagaaat    11700
aacgccggaa cattagtgca ggcagcttcc acagcaatgg catcctggtc atccagcgga    11760
tagttaatga tcagcccact gacgcgttgc gcgagaagat tgtgcaccgc cgctttacag    11820
gcttcgacgc cgcttcgttc taccatcgac accaccacgc tggcacccag ttgatcggcg    11880
cgagatttaa tcgccgcgac aatttgcgac ggcgcgtgca gggccagact ggaggtggca    11940
acgccaatca gcaacgactg tttgcccgcc agttgttgtg ccacgcggtt gggaatgtaa    12000
ttcagctccg ccatcgccgc ttccacttt tcccgcgttt tcgcagaaac gtggctggcc    12060
tggttcacca cgcgggaaac ggtctgataa gagacaccgg catactctgc gacatcgtat    12120
aacgttactg gtttcacatt caccaccctg aattgactct cttccgggcg ctatcatgcc    12180
ataccgcgaa aggttttgcg ccattcgatg gtgtccggga tctcgacgct ctcccttatg    12240
cgactcctgc attaggaagc agcccagtag taggttgagg ccgttgagca ccgccgccgc    12300
aaggaatggt gcatgcaagg agatggcgcc caacagtccc ccggccacgg ggcctgccac    12360
catacccacg ccgaaacaag cgctcatgag cccgaagtgg cgagcccgat cttccccatc    12420
ggtgatgtcg gcgatatagg cgccagcaac cgcacctgtg gcgccggtga tgccggccac    12480
gatgcgtccg gcgtagagga tcgagatcga tctcgatccc gcgaaattaa tacgactcac    12540
tata                                                                12544
```